United States Patent
Littmann

(10) Patent No.: US 12,246,998 B2
(45) Date of Patent: Mar. 11, 2025

(54) NUTRIENT COMPLEXING COMPOSITIONS

(71) Applicant: Woodford Group LLC, Metamora, IL (US)

(72) Inventor: Robert J. Littmann, Peoria, IL (US)

(73) Assignee: Woodford Group LLC, Metamora, IL (US)

( * ) Notice: Subject to any disclaimer, the term of this patent is extended or adjusted under 35 U.S.C. 154(b) by 1249 days.

(21) Appl. No.: 16/809,039

(22) Filed: Mar. 4, 2020

(65) Prior Publication Data

US 2020/0407284 A1    Dec. 31, 2020

Related U.S. Application Data

(63) Continuation of application No. 15/724,599, filed on Oct. 4, 2017, now Pat. No. 10,633,298, which is a continuation of application No. 15/092,079, filed on Apr. 6, 2016, now abandoned.

(60) Provisional application No. 62/145,871, filed on Apr. 10, 2015.

(51) Int. Cl.
| | |
|---|---|
| C05F 11/00 | (2006.01) |
| A01N 25/00 | (2006.01) |
| A01N 43/713 | (2006.01) |
| A01N 43/90 | (2006.01) |
| C05C 1/00 | (2006.01) |
| C05C 11/00 | (2006.01) |
| C05D 9/00 | (2006.01) |
| C07C 211/14 | (2006.01) |
| C07C 211/63 | (2006.01) |
| C07C 215/50 | (2006.01) |
| C07C 279/02 | (2006.01) |

(52) U.S. Cl.
CPC .............. *C05F 11/00* (2013.01); *A01N 25/00* (2013.01); *A01N 43/713* (2013.01); *A01N 43/90* (2013.01); *C05C 1/00* (2013.01); *C05C 11/00* (2013.01); *C05D 9/00* (2013.01); *C07C 211/14* (2013.01); *C07C 211/63* (2013.01); *C07C 215/50* (2013.01); *C07C 279/02* (2013.01)

(58) Field of Classification Search
None
See application file for complete search history.

(56) References Cited

U.S. PATENT DOCUMENTS

| | | | |
|---|---|---|---|
| 10,407,353 B2 | 9/2019 | Rohrer et al. | |
| 2004/0142822 A1 | 7/2004 | Suzuki et al. | |
| 2010/0248965 A1* | 9/2010 | Hacker ................. | A01N 47/36 504/133 |
| 2016/0044882 A1 | 2/2016 | Herr | |

FOREIGN PATENT DOCUMENTS

FR    1542058    * 10/1968

OTHER PUBLICATIONS

English abstract of FR 1542058 (Oct. 1968).*
Ross, E. et al., "The interaction of BMXD and its copper(II) complexes with glycine, aspartic acid, and histidine," Inorganica Chimica Acta, vol. 286(1), pp. 55-61 (1999).*

* cited by examiner

*Primary Examiner* — John Pak
(74) *Attorney, Agent, or Firm* — Barnes & Thornburg LLP

(57) ABSTRACT

The invention provides compositions, systems and methods for controlling loss of nutrients and other substances from planting sites.

13 Claims, 13 Drawing Sheets

TABLE 5: NITROGEN/NUTRIENT UTILIZATION EFFICIENCY SERIES A, B AND C VERSUS CONTROL BY VARYING APPLIED NITROGEN DOSAGES.

TABLE 6: NITROGEN/NUTRIENT UTILIZATION EFFICIENCY SERIES D, E AND F VERSUS CONTROL BY VARYING NITROGEN DOSAGES.

NUTRIENT COMPLEXING COMPOSITIONS

RELATED APPLICATIONS

The present application is a continuation of the U.S. patent application Ser. No. 15/724,599, filed Oct. 4, 2017, which is a continuation of U.S. patent application Ser. No. 15/092,079, filed on Apr. 6, 2016, which claims benefit under 35 U.S.C. § 119 (e) of the U.S. Provisional Application No. 62/145,871, filed Apr. 10, 2015, the contents of which are incorporated herein by reference in their entirety.

TECHNICAL FIELD

The present disclosure relates generally to compositions, systems and methods for controlling loss of nutrients and other substances from planting sites. Generally, the present invention relates to specific ion complexing agents and methods of use and manufacturing thereof. In particular, the present invention relates to incorporating complexing agents in planting media.

Background

Farmers strive for high crop yields. In the process of doing so, they may use excessive amounts of nutrient providing fertilizers. Most companies and individuals with lawns, gardens, golf courses, etc., want them to look green, fruitful and vibrant. In the process of doing so, they may use excessive amounts of fertilizers. Nutrient run-off and ground water contamination may be caused by excessive nutrient application to agricultural lands, golf courses, parks, nurseries, gardens, lawns, and other sites. The run-off of nutrients causes hypoxia may cause the death and growth inhibition of most aquatic life. Vivid examples are the dead zones in the Gulf of Mexico and Lake Erie. Surface water and ground water contamination with nutrients may cause increased potable water treatment costs, and expensive and complicated processes. The underlying issues are outlined in the report titled "Ceres Water Climate Risk Corn Report" dated June 2014 and "What is Hypoxia" dated Dec. 6, 2014 by Jennifer Iarino, Nola.com. Additional information can be found in the publication "COMING TOGETHER TO PROTECT MISSISSIPPI RIVER WATERSHEDS", published by the U.S. Water Alliance, August 2014.

For millennia, agriculturalists have demonstrated the effectiveness of natural (manures) and chemically synthesized fertilizers to increase farm crop yields. Increased farm yields depend on many factors. Fundamentally, farms are businesses. While yields for corn can range from 170 bushels/acre to 465 bushels/acre, the 50 percentile for yield is about 200 bushels/acre. In the final analysis, the farmer's basic objective is profit/return on investment. Value propositions are a way of life for farmers. High fertilizer addition rate equals improved profits for most farmers even though it causes nutrient runoff to waterways.

Plants require 16 nutrients to grow. Non-mineral nutrients include hydrogen, oxygen and carbon. These nutrients are found in the air and water. Plants use energy from the sun to change carbon dioxide and water into starches and sugars through photosynthesis. These starches are the plant's food. Since plants get carbon, hydrogen and oxygen from the air and water there is little farmers can do (other than locate plants in sunny areas/irrigate when rainfall is low) to control how much of these nutrients are available to the plants.

The 13 mineral nutrients, which come from the soil, are dissolved in water and absorbed through a plant's roots. There are not always enough of these nutrients in the soil for healthy plant growth. This is why many farmers use fertilizers to add the nutrients to the soil. The mineral nutrients are divided into two groups: macronutrients and micronutrients.

Macronutrients can be broken into two more groups: primary and secondary nutrients. The primary nutrients are nitrogen, phosphorus, and potassium. These major nutrients usually are lacking from the soil because plants use large amounts for their growth and survival. The secondary nutrients are calcium, magnesium, and sulfur. There are usually enough of these nutrients in the soil, so fertilization with secondary nutrients is not always needed.

The 7 micronutrients are those elements essential for plant growth which are needed in only very small quantities. These elements are boron, copper, iron, chloride, manganese, molybdenum and zinc. If required micronutrients are available in the soil, no supplemental addition is required.

Soils vary widely in composition, structure, and nutrient supply. Especially important from the nutritional perspective are inorganic and organic soil particles called colloids. Soil colloids retain nutrients for release into the soil solution where they are available for uptake by the roots. Soil colloids serve to maintain a reservoir of soluble nutrients.

The function of the colloidal soil fraction depends on two factors: (1) colloids present a large specific surface area, and (2) the colloidal surfaces carry a large number of charges. The charged surfaces in turn reversibly bind large numbers of ions, especially positively charged cations from the soil solution. This ability to retain and exchange cations on colloidal surfaces is the single most important property of soils, insofar as plant nutrition is concerned.

Colloidal clays supply predominately negative charges by virtue of the alumina and silica at the edges of the clay particle. Because colloidal carbon is derived largely from lignin and carbohydrates, it also carries negative charges arising from exposed carboxyl and hydroxyl groups.

Soil colloids are predominantly nonionic and anionically charged and, consequently, they do not tend to attract negatively-charged anions (in other words, the anion exchange capacity of soil colloids is relatively low). The result is that anions are not held in the soil but tend to be readily leached out by percolating ground water. This situation has important consequences for agricultural practice. Nutrients supplied in the form of anions must be provided in large quantities to ensure sufficient uptake by the plants. As a rule, farmers often find they must apply at least twice—sometimes more—the amount of nitrogen required for producing a crop.

Unfortunately much of the excess nitrate is leached into the ground water, and eventually finds it's way into wells or into streams and lakes, where it contributes to problems of eutrophication by stimulating the growth of algae. Similar issues relate to the inefficient uptake of negatively charged phosphorous ($PO_4^-$) and sulfur ($SO_4^-$) by plants, with subsequent problems resulting from nutrient runoff.

Plants vary on how much macronutrient (nitrogen, phosphorous, potassium) they require for robust growth. For example, corn requires high levels of nitrogen while legumes do not require any nitrogen as they are able to fix nitrogen requirements from the air.

There are three fundamental ways plants uptake nutrients through the root: 1) simple diffusion, occurs when a non-polar molecule, such as $O_2$, $CO_2$, and $NH_3$ follows a concentration gradient, moving passively through the cell lipid bilayer membrane without the use of transport proteins; 2) facilitated diffusion, is the rapid movement of solutes or ions following a concentration gradient, facilitated by transport proteins; 3) Active transport is the uptake by cells of ions or molecules against a concentration gradient. This requires an energy source, usually ATP, to power molecular pumps that move the ions or molecules through the membrane.

Three of the important macronutrients, nitrogen, phosphorous and sulfur enter the plant cell wall in the form of anions. If these macronutrients are not retained in the soil in proper concentration to facilitate their transport across the plant cell wall, excess fertilization will be required to obtain optimum crop yields.

Methods being considered to control nutrient run-off include collection of run-off water and removal of nutrients. This increases pollution abatement capital and operating costs, and does not address ground water contamination or optimization of crop yields.

Another method being considered is to grow scavenger plants around the perimeter of agricultural fields to capture the excess nutrients. This does not address the wastage of fertilizer usage nor does it address ground water contamination or the desirability of increased crop yield.

Increase of the soil Cation Exchange Capacity "CEC" by usage of humic acid is neither efficient nor effective at addressing the need for retaining anions. The theory of increasing CEC is that ammonia while being a cation readily nitrifys to nitrates which are anions and thus not retained in the solid. Nitrification blockers are an additional expense and only partially effective. Frequently nitrogen is applied in the form of ammonium nitrate. The nitrate form of nitrogen is negatively charged and not affected by CEC. Further, phosphates and sulfates are also anions and not effectively retained by CEC.

Clays, which are the main source of CEC, have low efficiency, being less than 10% as efficient in retaining cations, than the proposed compositions of matter. Many cations in the soil and needed by plants are actually anion complexes and thus are not retained by CEC. Moreover, clays are weakly charged. As such, there is minimal inhibition of hydraulic leaching of bound cations during irrigation or rains.

The present invention addresses these issues in part.

SUMMARY

Disclosed herein are compositions of matter, systems, and methods for minimizing nutrient run-off and surface/ground water contamination by retaining nutrients in proximity to plant roots until they are required by plants. Without wishing to be bound by a theory, the compositions, systems and methods disclosed herein can enable high crop yields, vibrant lawns, and fruitful gardens, without excessive application of nutrients. Nutrients can be retained in the soil until they are needed by plants. Nutrients can be resistant to being washed away by rain, or excessive irrigation. The nutrients can be immobilized until required by plants. Further, the compositions and methods disclosed herein abate agricultural runoff and related groundwater contamination. This abatement using the compositions and methods disclosed herein can reduce fertilizer usage and increase crop yield.

Without wishing to be bound by a theory, the compositions, systems and methods disclosed herein complex anions and cations. The method of complexing anions and cations may retain nutrients and essential minerals until required by plants. The mechanism of complexing can include surface adsorption.

In one aspect, then invention provides a method for retaining a desired compound or molecule at a planting site or reducing or inhibiting loss of a desired compound or molecule from a planting site. Generally, the method comprises incorporating a specific ion complexing agent in planting media at the planting site. Without limitations, any method for incorporating a composition in planting media can be used. Exemplary methods for incorporating a composition in planting media can include, but are not limited to, mixing, blending, reacting and the like.

In another aspect, the invention provides a composition capable of specifically and reversibly binding or complexing with an ion, molecule or compound. Generally, the composition comprises a component, e.g., a specific ion complexing agent (SICA) that reversibly and specifically complexes or binds with an ion, molecule or compound. In some embodiments, the SICA complexes anions or cations.

DETAILED DESCRIPTION

Figure 1:
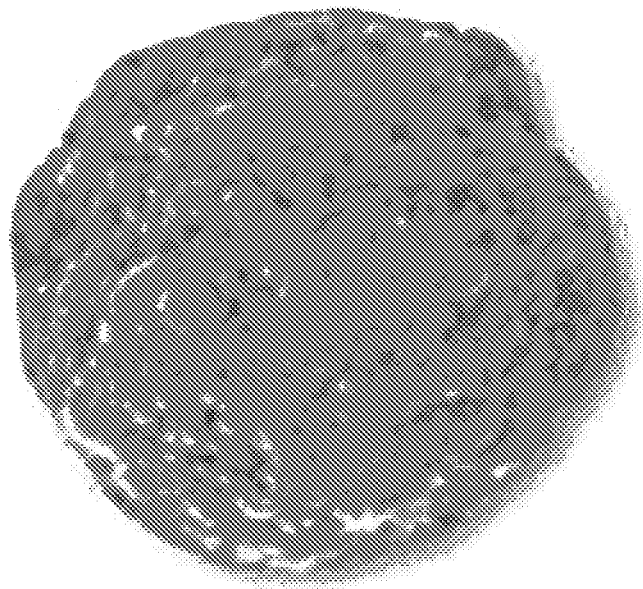
FIGS. 1-4 are illustrations of exemplary compositions according to exemplary embodiments of the invention.
Figure 2:
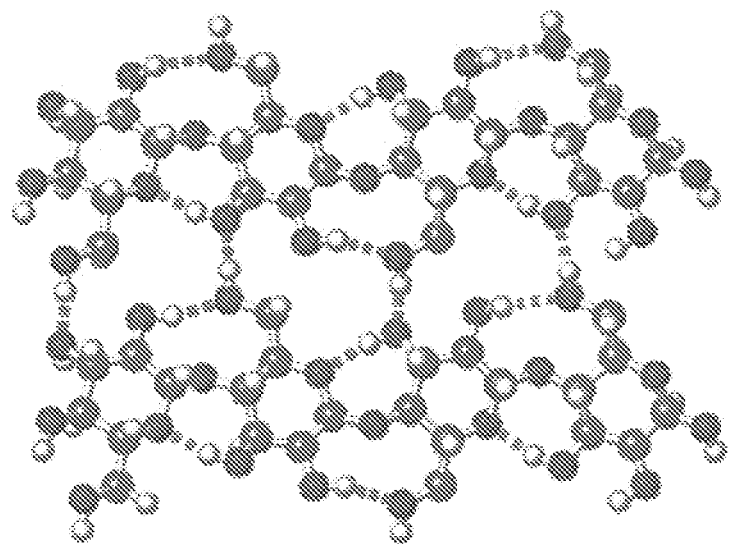
Figure 3:
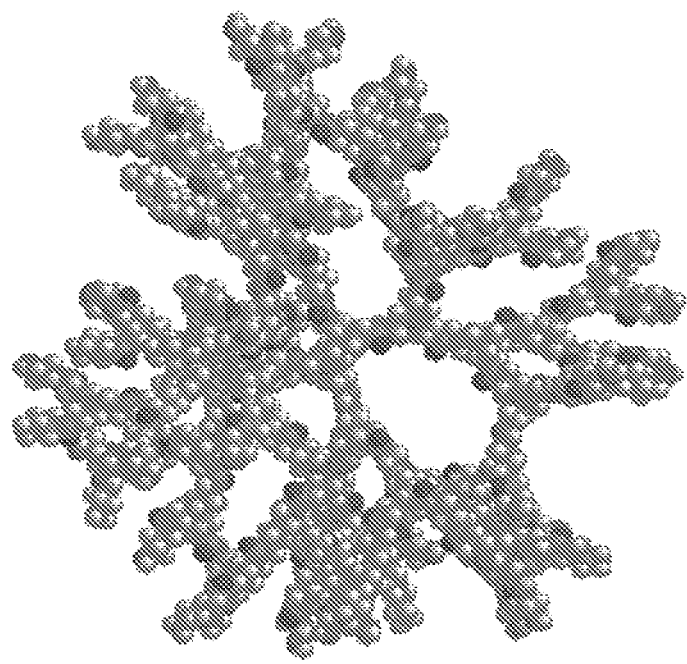
Figure 4:
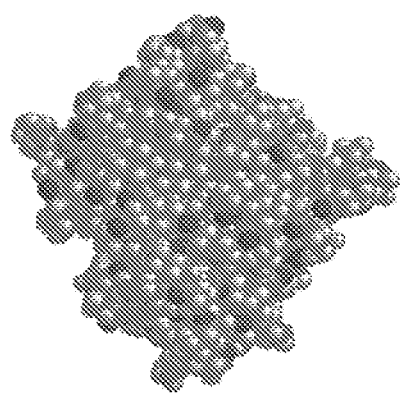

The compositions, systems, and methods disclosed herein can retain nutrients and essential minerals in plant growth media until they are required by plants. Thus, compositions, systems, and methods disclosed herein can enable proportional feed of nutrients and essential minerals to plants optimizing crop yields by utilizing plant proton pumps. Selective complexing of nutrients and essential minerals can enable efficient retention and dispensing of nutrients and essential minerals when desired by plants. Further, complexing sites in the compositions disclosed herein are not blocked by undesirable elements or compounds. Overfeed of nutrients and essential minerals is abated which abates nutrient and essential mineral loss to runoff and ground water thus controlling pollution of same.

The compositions, systems, and methods disclosed herein can combine with nutrients and retain concentrated nutrients in contact with or in the proximity of plant roots. Their use can promote optimum plant growth and crop yield while using less fertilizer. Their use can substantially reduce nutrient runoff from farms by reducing excess nutrients in the soil.

The compositions, systems, and methods disclosed herein can: 1) increase crop yields and/or optimize lawn appearance; 2) reduce fertilizer usage; 3) facilitate the usage of nutrients and essential mineral proportional to plant need; 4) rationalize municipal waste bio-solids; 5) improve water absorption for use during dry spells if and when desired.

The compositions, systems, and methods disclosed herein can be customized to specific crop or soil requirements, and can abate pollution of surface waters and ground waters.

In one aspect, the invention provides a method for reducing or inhibiting loss of a desired compound or molecule, such as ions, nutrients, essential minerals, pesticides, herbicides, growth stimulators, water and other substances from a planting site. Generally, the method comprises incorporating a specific ion complexing agent (SICA) at the planting site, wherein said composition retains the desired compounds or molecules, such as ions, nutrients, essential minerals, pesticides, herbicides, growth stimulators, water and other substances, minimizing their loss to run-off, loss to ground water, loss to evaporation or loss to windage.

Without wishing to be bound by a theory, the SICA functions by forming a complex with the desired compound or molecule. For example, the SICA comprises one or more functional groups that can bind to the desired compound or molecule to form a coordination complex. When the SICA comprises more than one functional group that can bind to the desired compound or molecule to form a coordination complex, the functional groups can all be the same or all different or any combinations of same and different. When the SICA comprises more than one functional group that can bind to the desired compound or molecule to form a coordination complex, the functional groups can be spatially arranged and/or organized to form multiple (e.g., two, three, four or more) points of contact between the SICA and the desired compound or molecule. Further, the functional groups can be spatially arranged and/or organized to form a three-dimensional shape complementary to the shape of a desired compound or molecule. The coordination complex can be neutral, cationic or anionic. It is noted the coordination complex, along with its counterions, if required, is referred to as a coordination compound herein.

The bonding between the desired compound and SICA generally involves formal donation of one or more of the SICA's electron pairs. Without limitations, the nature of the compound-SICA bonding can range from covalent to ionic. By way of example, when the desired compound or molecule is a cation, the SICA can form a coordination covalent bond with the desired compound or molecule. On the other hand, when the desired compound or molecule is an anion, the SICA can form a hydrogen bond with the desired compound or molecule. Furthermore, the compound-SICA bond order can range from one to four. In other words, there can be one, two, three or four bonds between the compound and the SICA. In many embodiments, there are three or four bonds between the compound and the SICA. It is noted that nutrients are generally viewed as Lewis bases but sometimes can involve Lewis acidic nutrients.

Without limitations, the desired compound or molecule can bind to the SICA in virtually all circumstances. SICA in a complex dictate the reactivity of the central atom, including SICA substitution rates, the reactivity of the SICA themselves, and redox. SICA selection is a critical consideration in forming specific or highly selective complexes with the desired compound or molecule. Generally the SICA are classified by the specific compound or molecule being complexed.

Generally, the specific ion complexing agent is an atom, molecule or ion which has one or more pairs of electrons which can be donated to the desired compound or molecule (such as nutrient atom, ion or molecule) to form a complex and/or coordination bonds with the desired compound or molecule. Without wishing to be bound by a theory, the binding affinity of the SICA with the desired compound depends upon the interaction force of attraction between the SICA and the binding sites in the desired compound or molecule. Strong intermolecular force of attraction results to show high bonding affinity SICA binding, while the SICA binding of low-affinity involves lower and weak intermolecular force between SICA and desired compound.

In many embodiments, SICA have a three-dimensional shape and the SICA and the desired compound are complementary to each other in their shape and geometry. Thus, for every SICA there is a specific desired compound or molecule (such as a nutrient/metal) and they are complementary to each other in their size and geometry. As such, if the particular desired compound or molecule does not have appropriate shape, the SICA will not bind with it or bind at a relatively low rate. For a strong binding between SICA and the desired compound or molecule their shapes/geometries need to be complementary to each other.

In some embodiments, SICA for a particular desired compound or molecule can be selected based on one or more of the following considerations. For example, if positively charged ammonium ions are to be retained, the functional group would necessarily be negatively charged.

Generally, SICA binding selectivity is defined with respect to the binding of SICA to the desired compound molecule to form a complex. The specificity of a SICA for a desired compound or molecule is determined by compound's spatial geometry and the way it binds to the SICA through non-covalent interactions, such as hydrogen bonding or van der Waals forces. A selectivity coefficient is the equilibrium constant for the reaction of displacement by one SICA of another SICA in a complex with a nutrient or metal.

For example, bonding of anionic molecule or compound with SICA involves interactions between molecular or ionic species in the absence of covalent bond formation. Binding affinities between anions and their SICA is attributed primarily to hydrogen-bonding which promotes selective binding through topological complementarity. Truly selective anion SICA involves some elements of a strategic design, including appropriately positioned hydrogen-bond coordination sites.

As described above, SICA binding with an anion comprises hydrogen-bonding. For binding with a cationic molecule or compound, SICA binding is defined as a Lewis base that donates a pair (or pairs) of electrons to the cation via a coordinate covalent bond Thus, where anion binding is invoked, the SICA is generally should be understood to refer to Lewis acid capability and the term "binding" refers to hydrogen bonds as opposed to coordinate covalent bonds.

A number of factors influence the strength, selectivity, and structures present in the binding between desired compound or molecule and SICA. Exemplary such factors include, but are not limited to, hydrogen bonding, topology, dimensionality, and charge (or electrostatic interactions). These exemplary factors are discussed herein below as they influence selection of a SICA for binding with an anionic molecule or compound.

A simple set of SICA based on similar carbon frameworks was prepared to explore the exemplary factors influencing SICA selection for anions. See FIG. 19.

Hydrogen Bonding: Hydrogen bonding is a major structure-defining aspect of the secondary valence in anion binding. The introduction of multiple hydrogen-bonding sites along with the resulting topological considerations in anion receptors leads to the concept of double valence for anions as well as for transition-metal ions. For anions, however, the primary valence is the negative charge on the anion and the secondary valence is provided by hydrogen bonds to the anion. The atoms coordinated via the secondary valence in transition metal complexes are arranged in symmetrical shapes around the central metal. After examining the structures of a number of anion complexes, it is observed that a similar symmetrical bonding pattern also occurs quite frequently for anions.

Figure 19:
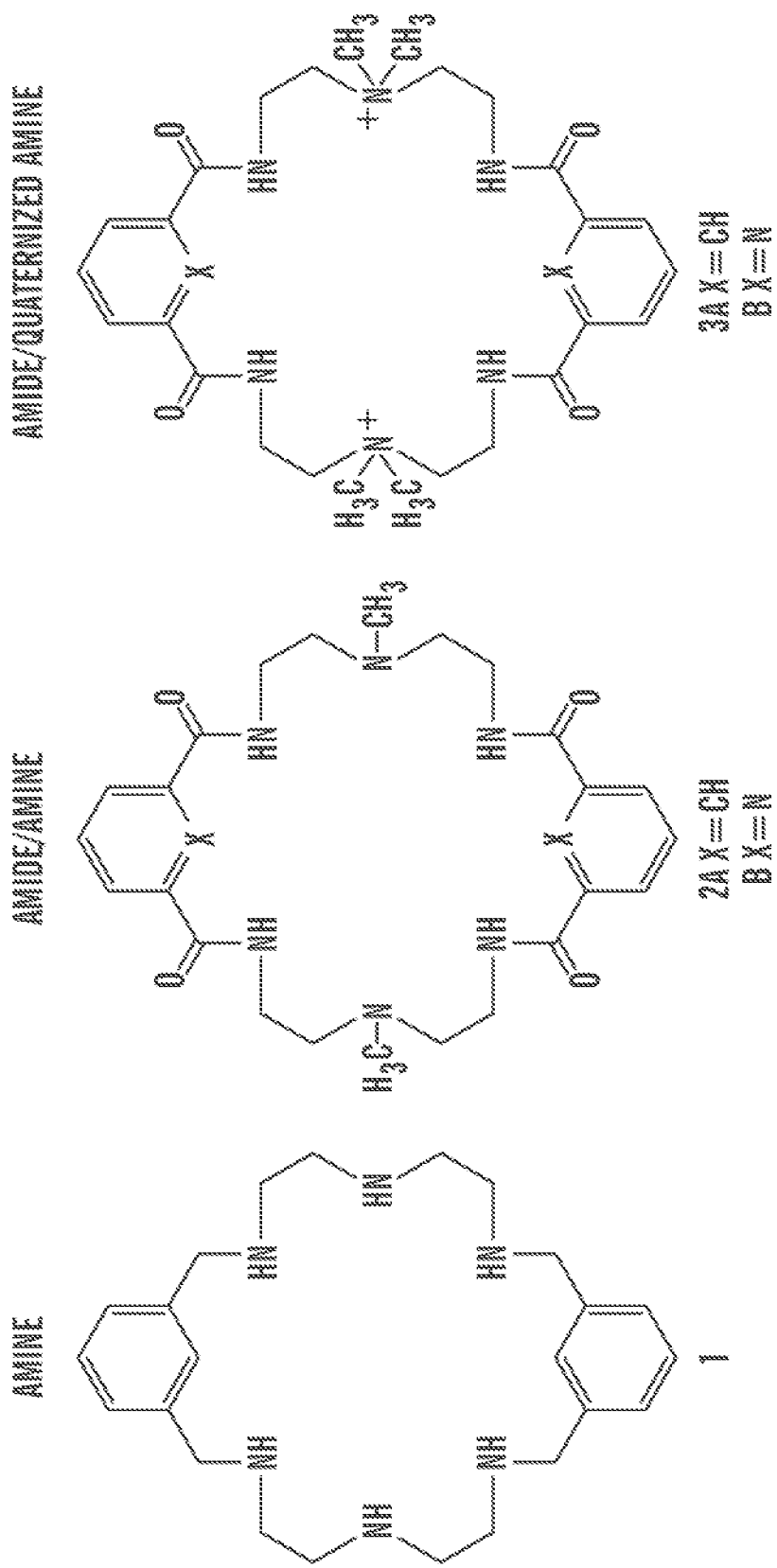
FIG. 19 shows exemplary SICA according to some embodiments of the invention.
Figure 19:
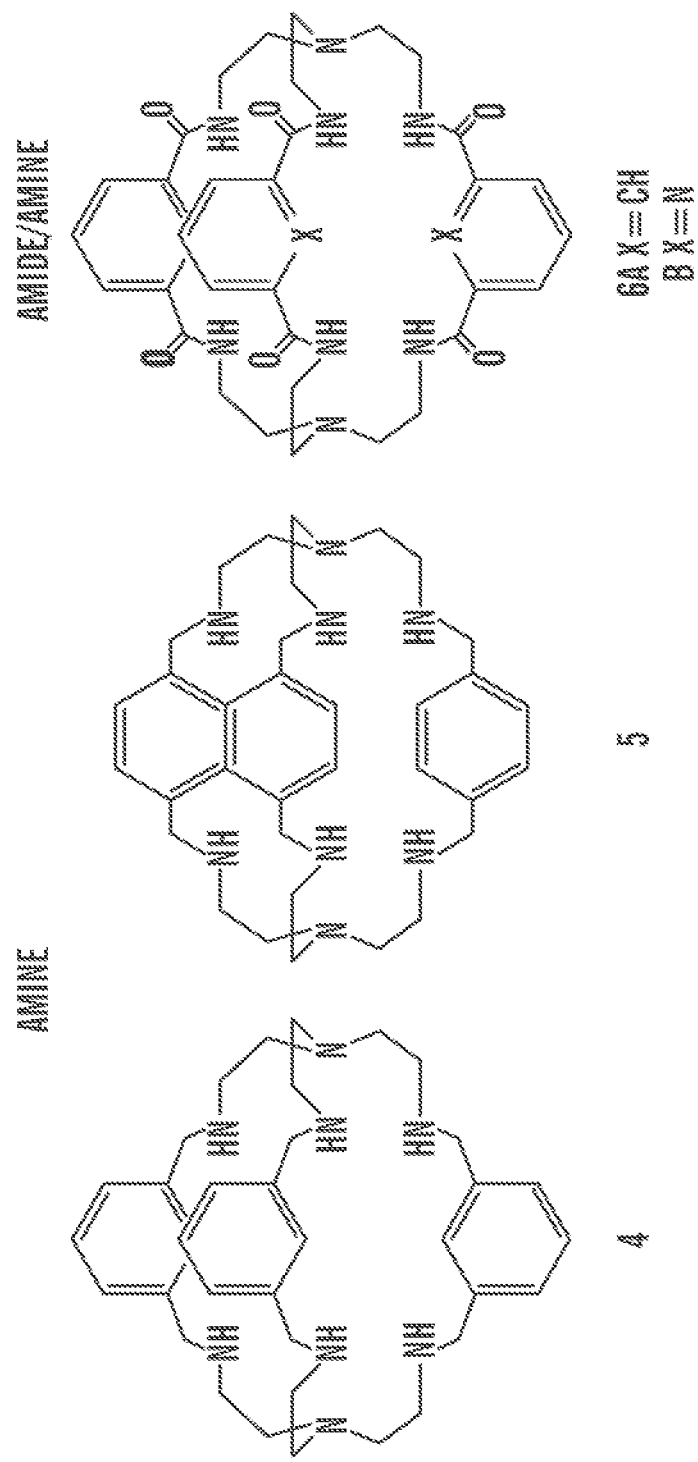

In the exemplary SICA depicted in FIG. 19, two types of hydrogen-bond donors are presented, amines and amides. The polyamine SICA, 1, 4, and 5, are readily obtained by simple Schiff base condensations of either 2,2'-diaminodiethylamine (dien) or 2,2',2''-triaminotriethylamine (tren) with aromatic or heterocyclic dialdehydes followed by borohydride reduction. These SICA simulate Nature as they often involve amide linkages as hydrogen-bond donors. The amide-based macrocycles, 2 and 6, are synthesized maintaining the same framework structure of the amines. These too are relatively straightforward synthetic procedures using N'-methyl-2,2'-diaminodiethylamine (Medien) or tren with the diacid chlorides of the aromatic spacers.

Charge: Electrostatic interactions between a negatively charged anion and a positively charged SICA can influence and enhance binding. Polyammonium SICA are polyprotonated when they bind anions, with significant binding usually commencing after several protons are added to the macrocycle. The two amine functionalities of the amide-based monocycle, 2, provide sites for charge addition via quaternization to yield the dicationic SICA 3. A direct evaluation of the effect of positive charge in the absence of additional hydrogen bonding can be evaluated by comparing the two closely related classes of SICA, 2 and 3.

Dimensionality: Comparing monocyclic versus bicyclic binding of anions in polyammonium systems utilizes dien and tren as SICA frameworks of monocycles such as 1 and bicycles such as 4 and 5, respectively. The same strategy is used to expand the tetraamido framework of 2 to the hexaamido SICA, 6.

Topology: It is important to consider topology in the placement of hydrogen-bond acceptors in the SICA, to overcome "bias" and achieve selective recognition. Exemplary topologies for anions include, but are not limited to, spherical (halides), trigonal planar (nitrate), and tetrahedral (ammonium, sulfate and phosphate). As a result of the strategic placement of hydrogen bonding sites on SICA, a number of common geometries and multiple hydrogen-bond interactions can be observed for SICA/anionic compound or molecule complexes. This points to the importance of design in anion recognition as discussed in more detail below.

Binding Numbers and Geometries: Examination of the structural results for anion complexes of the SICA depicted in FIG. 19 reveals analogies between anion binding and cation binding. These similarities include multi-bond binding, which refers to the number of donor groups in a single SICA that bind to a central atom or molecule, as well as structural motifs such as cascade and sandwich complexes. Coordination numbers from one coordinate to nine coordinate, with many of the multiple bound anions exhibiting the same regular geometries observed for cation complexes. Without wishing to be bound by a theory, the geometrical patterns can be explained as the result of simple charge repulsion phenomena. It is noted that these findings are merely structural observations. Structural aspects of the multifaceted influences of hydrogen bonding, charge, dimensionality, and topology in terms of coordination numbers and geometries are discussed below in more detail.

In the present disclosure, binding numbers of an atom in a molecule is determined by simply counting the other atoms to which it is bonded. For example, Nitrite with the formula $NO_2^{1-}$ is a nitrogen atom bonded to two oxygen atoms. It would have a SICA binding number of two. Accordingly, nitrate with the formula $NO_3^{1-}$ is a nitrogen atom bonded to three oxygen atoms. It would have a SICA binding number of three. Phosphate with the formula $PO_4^{3-}$ is a phosphorous atom bonded to four oxygen atoms. It would have a SICA binding number of four.

One Coordinate (Mono-bond): Many two-dimensional macrocycles (monocycles) form simple one-coordinate species with anions, particularly if their binding functionalities are not "preorganized" for multi-bond binding. As a result, these structures tend to crystallize with layers of alternating anions and cations.

Figure 20:
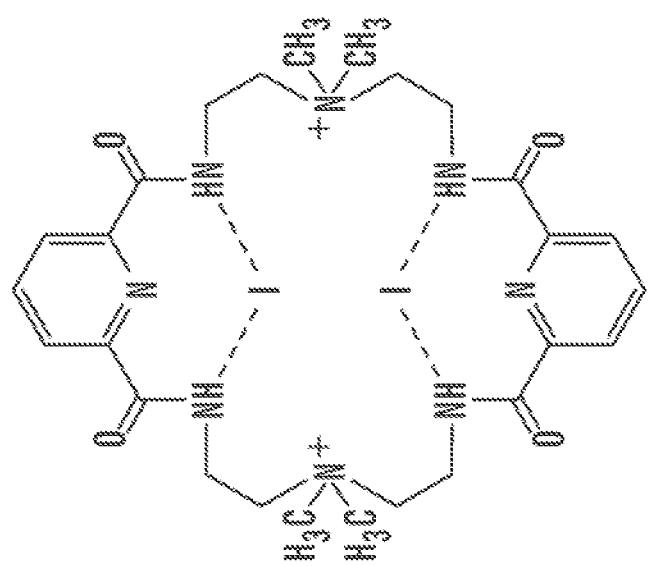
FIG. 20 is a schematic representation of bi-binding of iodide with an exemplary SICA (3B shown in FIG. 19).

Two Coordinate (Bi-bond): Two-coordinate complexes can result from bi-bond formation with donors in the same SICA. Such binding modes are prevalent in cation coordination chemistry and are responsible for the enhanced thermodynamic stabilities of complexes containing binding SICA compared with their mono-bind analogues. Crystallographic results for SICA containing pyridine spacers indicate internal hydrogen bonding between the pyridine and both adjacent amide hydrogens, while in the m-xylyl analogs, structures indicate a more random orientation of the hydrogens either in or outside of the cavity. These findings indicate a preorganization of the key binding moieties implemented by the pyridine lone pair. The result is a bi-binding effect as seen for SICA 3B with iodide (FIG. 20).

Binding studies also show enhanced binding of both 2B and 3B, containing pyridine spacers, over the m-xylyl analogues, 2A and 3A, indicating the favorable effect of preorganization on binding. Furthermore, the Tetra SICA 3 exhibit a higher affinity for almost all anions compared to their neutral counterparts. For example, for dihydrogen phosphate, the affinities determined by NMR are log K 2.92 (2A), 4.06 (3A), 4.04 (2B), and >5 (3B) in DMSO-d6. Thus, a comparison of these four SICA provides insights on the influence of both preorganization (resulting in multi-binding) as well as charge on anion binding.

Figure 21:
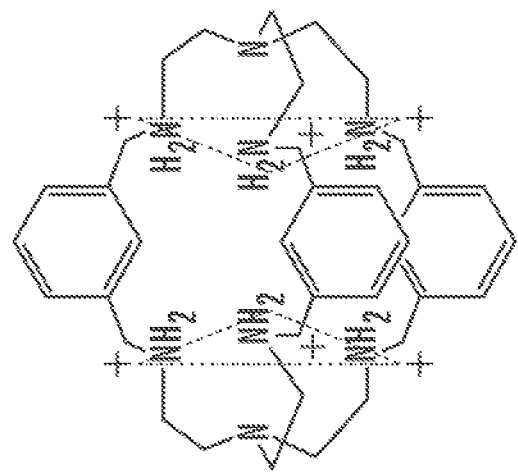
FIG. 21 is a schematic representation of dual binding tri-donor trigonal planar coordination of nitrate with SICA 4.

Three Coordinate (Tri-Bond): The 3-fold symmetry of the bicyclic SICA 4 provides a perfect framework for trigonal recognition, as seen in the structure of the dual binding nitrate complex (FIG. 21). The trigonally arrayed amines are ideally situated to accommodate the trigonal planar nitrates. Each of the nitrate oxygens is held by two hydrogen bonds with adjacent ammonium hydrogens, with one being normal (2.8-2.9 Å) and one slightly longer (3.0-3.1 Å).

The multiple binding observed for the nitrate oxygens is in agreement with the attractive electrostatic potential (ESP) for nitrate and sulfate oxygen atoms using DFT calculations.

Four Coordinate (Tetra-Bond): As in transition metals, tetra-bind is a very common coordination number for anions, especially for the halides. Four-coordinate tetrahedral geometries are observed in fluoride complexes with the two aza-SICA, 4 and 5. In 4, the complex is dual-bound, with one fluoride and water molecule encapsulated in the SICA. However, by just a slight expansion of the cavity with a p-xylyl spacer, a tritopic complex is obtained with two fluorides and a bridging water molecule in the SICA. The chloride complex of 5, however, contains only a single chloride and water molecule as seen in the fluoride complex of 4, indicating the influence of anion size as well as cavity size on topology.

In terms of binding affinities, encapsulation enhances binding for the Polyammonium SICA 4 and 5 compared to their monocyclic counterparts. For example, the monoanionic nitrate and fluoride ions show only very weak binding with hexaprotonated $H_6 1^{6+}$ (log K≤2), while log K of the dianionic sulfate is >4. The hexaprotonated SICA corollary, $H_6 4^{6+}$ however, binds strongly with all three anions: log K) 3.11, 3.56, and 4.36 for nitrate, fluoride, and sulfate, respectively. These studies were all performed using potentiometric techniques in aqueous solution with potassium tosylate as the electrolyte.

Five Coordinate (Penta-Bond): Penta-coordination is observed for a complex between sulfate and the aza-SICA 4. In this structure, all eight of the SICA amines are protonated and the sulfate is encapsulated in the cavity. However, none of the secondary amines on the left side of the macrocycle as pictured is hydrogen bonded with the internal sulfate, which bonds only to the two axial tertiary amines and the three secondary amines on the right side of the macrocycle. In terms of coordination geometry, in transition-metal chemistry, the two commonly occurring five-coordinate geometries are square pyramidal and trigonal bi-pyramidal. In the sulfate structure with octaprotonated SICA 4 (H848+), the coordination can best be described as a distorted trigonal bi-pyramid. The coordination assignment is based on the topology of the nitrogen atoms associated with the sulfate via hydrogen bonds. The three secondary amines form the trigonal plane, while the protonated bridgehead amines provide the axial sites, making 4 a penta-bond SICA.

Higher order complexes, such as Six Coordinate, Seven Coordinate, eight Coordinate and Nine Coordinate generally are effective in retaining very high molecular weight molecules including ATP, DTP and MTP, amino acids, RNA and DNA. As such, they find limited applications complexing and retaining nutrients, micro and trace metals in soil.

The functional groups that binds with the desired compound or molecule to form the coordination complex are also referred to herein as "complexing functional groups." As used herein, the term "complexing functional group" refers to a functional group or moiety that is capable of forming a complex with a desired ion, molecule or compound. Complexing functional groups are also referred to as exchange functional groups herein. Some exemplary complexing functional groups include, but are not limited to, sulfonic, carboxylic, carboxylate, hydroxyl, halogen, carbonyl, haloformyl, carbonate, alkoxy, acetal, hemiacetal, ketal, hemiketal, amide, amine, primary amine, secondary amine, tertiary amine, quaternary amine, primary ketamine, secondary ketamine, primary aldimine, secondary aldimine, imide, azide, azo, nitrate, nitrile, isonitrile, cyanate, isocyanate, nitro, nitroso, sulfhydryl, sulfide, disulfide, sulfinyl, sulfonyl, sulfino, sulfo, isothiocyanate, carbonothioyl, phosphino, phosphono, phosphate, borono, boronate, borino, borinate, and the like.

In some embodiments, the complexing functional group can be selected from the group consisting of acetamidine, benzamidine, ethylamine, diethylamine, tri-butylamine, triethylamine, sulfonic, carboxylic, alkanes, alkenes, alkynes, arenes, alkyl halides, aryl halides, alcohols, phenols, ethers, aldehydes, ketones, carboxylic acids, esters, amides, amines, nitriles, nitros, and any combinations thereof.

Table 1 lists exemplary functional groups that can be employed and converted to a desired complexing functional group depending upon the chemical, such as the nutrient to be complexed. Without limitations, the functional groups can be reacted or formed on a substrate or monomer comprising the functional group can be crosslinked to create a fine particle or resin of itself. As discussed herein, the complexing functional group, imparted to a substrate or to itself, is customized to the ion or compound to be retained and released as previously described. Examples of the type of functionalization can include, but are not limited to sulfonation, carboxylation, methylation, alkylation, amination, phosphorolation, and the like.

Generally, any organic compound that can complex anion nitrate molecules when protonated can be used as nitrate complexing functional group. These protonated compounds can be organized into SICA to form three points of contact between the SICA and the nitrate oxygen-hydrogen bonds. Exemplary nitrate complexing functional groups include, but are not limited to, amidine, guanidine, imine and amides Similarly, any organic compound that can complex anion phosphate/sulfate when protonated can be used as a phosphate/sulfate complexing functional group. These protonated compounds can be organized into SICA to form four points of contact between the SICA and the phosphate or sulfate oxygen-hydrogen bonds. Exemplary phosphate or sulfate complexing functional groups include, but are not limited to ethylamine, diethylamine, tri-butylamine and triethylamine based functional groups. Exemplary cation complexing functional groups include, but are not limited to sulfonic and carboxyl groups. The desired compound or molecule can be retained, or by mixing complexing functional groups a broad range of anion or cation complexes can be retained and dispensed when the plant requires them.

TABLE 1

| Class | General Formula | Example | Common Name (Systematic Name) | Common Suffix/Prefix (Systematic) |
|---|---|---|---|---|
| Hydrocarbons | | | | |
| Alkanes | RH | CH$_3$CH$_3$ | ethane | -ane |
| Alkenes | RR'C=CR"R''' | H$_2$C=CH$_2$ | ethylene (ethene) | -ene |
| Alkynes | RC≡CR' | HC≡CH | acetylene (ethyne) | (-yne) |
| Arenes | ArH[b] |  | benzene | -ene |
| Halogen-Containing Compounds | | | | |
| Alkyl halides | RX | CH$_3$CH$_2$Cl | ethyl chloride (chloroethane) | halide (halo-) |
| Aryl halides | ArX[a] | 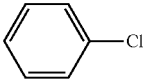 | chlorobenzene | halo- |
| Oxygen-Containing Compounds | | | | |
| Alcohols | ROH[a] | CH$_3$CH$_2$OH | ethyl alcohol (ethanol) | -ol |
| Phenols | ArOH[b] | 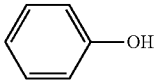 | phenol | -ol |
| Ethers | ROR' | H$_3$CH$_2$COCH$_2$CH$_3$ | diethyl ether | ether |
| Aldehydes | RCHO |  | acetaldehyde (ethanal) | -aldehyde (-al) |
| Ketones | RR'C=O |  | acetone (2-propanone) | -one |
| Carboxylic acids | RCO$_2$H |  | acetic acid (ethanoic acid) | -ic acid (-oic acid) |
| Carboxylic Acid Derivatives | | | | |
| Esters | RCO$_2$R' |  | methyl acetate (methyl ethanoate) | -ate (-oate) |
| Amides | RCONHR' |  | N-methylacetamide | -amide |
| Nitrogen-Containing Compounds | | | | |
| Amines | RNH$_2$, RNHR', RNR'R" | CH$_3$CH$_2$NH$_2$ | ethylamine | -amine |
| Nitriles | RC≡N | H$_3$CC≡N | acetonitrile | -nitrile |
| Nitro compounds | ArNO$_2$[a] | 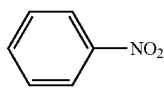 | nitrobenzene | nitro- |

[a] R indicates an alkyl group
[b] Ar indicates an aryl group.

For example, if nitrate is the nutrient to be complexed, an amidine can be used as the complexing functional group. Amidines can be derived from an oxoacid, a carboxylic acid derivative, resulting in a carboxamidine or carboximidamide with the following general structure:

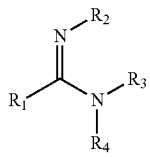

Amidines are much more basic than amides and are among the strongest bases. Protonation occurs on to the $sp^2$ hybridized nitrogen. This occurs because the positive charge can be delocalized onto both nitrogen atoms:

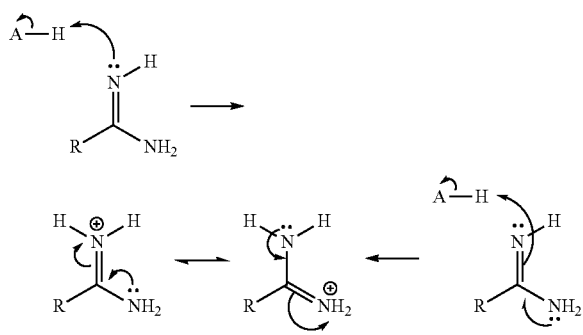

Another nitrate complexing functional group is guanidine, a compound with the formula $HNC(NH_2)_2$. Guanidine is found in urine as a normal product of protein metabolism. Guanidine is the functional group on the side chain of arginine. Guanidine is a nitrogenous analogue of carbonic acid functional group. That is, the C=O group in carbonic acid is replaced by a C=NH group, and each OH is replaced by a $NH_2$ group.

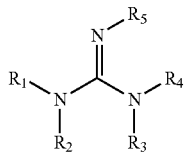

Some canonical forms of guanidine include:

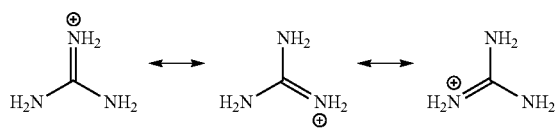

Another nitrate complexing functional group is imine. Imines contain a a carbon-nitrogen double bond, with the nitrogen atom attached to a hydrogen atom (H) or an organic group. The general structure of an imine:

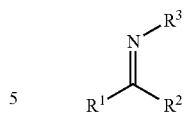

Imines are related to ketones and aldehydes by replacement of the oxygen with an NR group. When R=H, the compound is a primary imine, when R is hydrocarbyl, the compound is a secondary imine. Imines exhibit diverse reactivity and are commonly encountered throughout chemistry. When $R^3$ is OH, the imine is an oxime, and when $R^3$ is NH2 the imine is a hydrazone.

A primary imine in which C is attached to both a hydrocarbyl and an H is called a primary aldimine; a secondary imine with such groups is called a secondary aldimine. A primary imine in which C is attached to two hydrocarbyls is a primary ketimine; a secondary imine with such groups is a secondary ketamine.

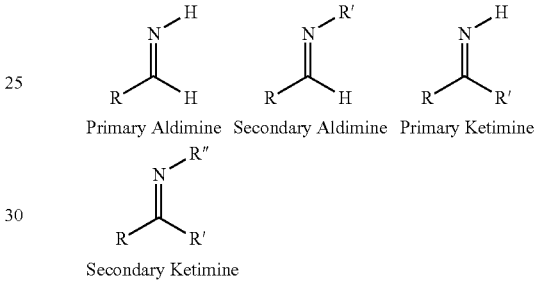

Primary Aldimine  Secondary Aldimine  Primary Ketimine

Secondary Ketimine

Imines are typically prepared by the condensation of primary amines and aldehydes or ketones.

Amide, an ammonium complexant, is a compound with the functional group $RnE(O)_xNR's2$ (R and R' refer to H or organic groups). Most common are "organic amides" (n=1, E=C, X=1), but many other important types of amides are known including phosphor amides (n=2, E=P, x=1 and many related formulas and sulfonamides (E=S, x=2). The term amide refers both to classes of compounds and to the functional group $(R_nE(O)_xNR'2)$ within those compounds. The structure of three kinds of amides:

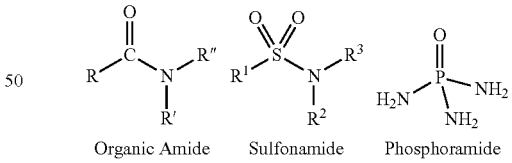

Organic Amide  Sulfonamide  Phosphoramide

The simplest amides are derivatives of ammonia wherein one hydrogen atom has been replaced by an acyl group. The ensemble is generally represented as RC(O)NH2. Closely related and even more numerous are amides derived from primary amines (R'NH2) with the formula RC(O)NHR' Amides are commonly derived from derived from secondary amines (R'R"NH) with the formula RC(O)NR'R". Amide are derivatives of carboxylic acids in which the hydroxyl group has been replaced by an amine or ammonia.

Amides are commonly formed via reactions of a carboxylic acid with an amine.

$RCO_2+R'R''NH \leftrightarrow RC(O)NR'R''+H_2O$

These reactions involve "activating" the carboxylic acid, the Schotten-Baumann reaction, which involves conversion of the acid to the acid chlorides.

Without wishing to be bound by a theory, SICA binds to the desired compound or molecule through multiple sites since the SICA can bind pairs on more than one atom. In some embodiments, SICA forms a bond to one or more central nutrient or metal atoms or ions. In some embodiments, SICA are macrocycles with three or more donor atoms that can bind to an ion or molecule center.

SICA can be prepared by linking together the complexing functional groups via a linker. The linker between a first pair of complexing functional groups can be the same or different than the linker between a second pair of complexing functional groups in the SICA. In some embodiments, the linker between each pair of the complexing functional groups in the SICA is the same. Exemplary linkers are described herein below.

In some embodiments, SICA can be prepared by forming the complexing functional group on a solid support. Exemplary solid supports are described herein below.

Without limitations, the SICA can be formulated in any desired shape or form. For example, the SICA can be in the form of a solid, liquid or gas. In some embodiments, the SICA can be in the form of solutions, long chain fibrous polymers, powders or granules.

In some embodiments, the SICA is in form of a solid. In some embodiments, the SICA is in form of a particle.

Without limitations, a particle of the invention can be a microparticle or a nanoparticle. Generally, the particle can be of any desired size. For example, the particle size can range from nanometers to millimeters. In some embodiments, the particle is about 0.0001 μm to about 100,000 μm, about 0.005 μm to about 50 μm, about 0.01 μm to about 25 μm, about 0.05 μm to about 10 μm, or about 0.05 μm to about 5 μm. In some embodiments, the particle is less than about 0.1 mm in size. In some embodiments, the particle is about 0.05 μm to about 5 μm in size. In some embodiments, the particle is about 2 μm in size.

It will be understood by one of ordinary skill in the art that particles usually exhibit a distribution of particle sizes around the indicated "size." Unless otherwise stated, the term "size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5.

Without limitations, the particle can be of any shape. Thus, the particle can be, but is not limited to, spherical, rod, elliptical, cylindrical, disc, and the like. In some embodiments, the particles have a substantially spherical shape. A substantially spherical particle is a particle with a difference between the smallest radii and the largest radii generally not greater than about 40% of the smaller radii, and more typically less than about 30%, or less than 20%.

The compositions of prior art, wherein cation complexing agents are mentions, have very low complexing capacity. In contrast, the specific ion complexing agents of the invention have high exchange capacity and selectivity. For example, the SICA of the invention can have two to more than ten times the complexing capacity of prior art cation complexing agents.

The exchange capacity of the SICA is enhanced by reacting the exchange site functional group with one which has preference for the desired compounds or molecule to be retained. In this manner, the exchange sites are selective for desired compound or molecules and exchange capacity is not taken by undesired compounds or molecules. For example selective retention of nitrate over sulfate, chloride or bicarbonate is achieved by employing an amidine complex such as acetamidine or benzamidine. If phosphate or sulfate radicals are the target for retention, ethylamine, diethylamine, tri-butylamine and triethylamine based functional groups can be used. Similarly cations are selectively complexed and released by incorporating sulfonic or carboxyl groups onto a substrate or to create a fine particle or resin of itself. Thus, specific nutrient complexes can be retained, or by mixing complexing functional groups a broad range of anion or cation complexes can be retained and dispensed when the plant requires them.

Generally, the specific ion complexing agents can have ion exchange capacity of at least 150 meq/100 grams. In some embodiments, the specific ion complexing agents of the invention have an ion exchange capacity of 200 meq/100 grams, 250 meq/100 grams, 300 meq/100 grams, 350 meq/100 grams, 400 meq/100 grams, 450 meq/100 grams, 500 meq/100 grams, 550 meq/100 grams, 600 meq/100 grams, 650 meq/100 grams or higher.

It is noted that the exact ion exchange capacity employed on an agricultural site needs to be balanced with the specific objective to be accomplished on that site. For example if a nutrient as nitrogen is to be applied to a site, at a dosage of 200 pounds per acre, the required nutrient dosage would be 0.357 meq/100 grams of soil. To complex and retain the nitrate until required by plants would require 0.357 meq/100 grams of soil. To retain nitrogen mobilized from decay of organic and other sources of nitrogen, the SICA dosage would be doubled to 0.714 meq/100 grams or 10 mg per 100 grams of soil. For clarification, SICA dosage can be calculated as follows. For example, if the N dosage is 200 pounds of N per acre$^3$, one acre$^3$ equals 4,000,000 pounds. 200 lbs N divided by 4 million pounds of soil equals 50 mg/Kg. 100 grams equals 0.1 Kg, therefore the dosage equals 5 mg/100 grams. Doubling of the dosage calculates to 10 mg/100 grams.

In some embodiments, the SICA are coupled via a coupling agent to an appropriate substrate to form a Nutrient Complexing Composition ("NCC") to enable the SICA to be uniformly distributed throughout the soil within contact with the rhizosphere (plant root zone) and be retained within the rhizosphere. If the coupling agent and the substrate equal 50% of the Nutrient Complexing Composition, then the preferred SICA/NCC dosage is 20 mg per 100 grams of soil. If the coupling agent and the substrate equal 75% of the NCR, then the preferred SICA/NCC dosage is 40 mg per 100 grams of soil.

Methods of determining exchange capacity are well known in the art and available to one of ordinary skill in the art. Methods of measuring Cation and Anion Exchange Capacity of soils is described, for example, in A. Mehlich, Determination of Cation and Anion Exchange properties of Soils, Soil Science: December 1948, Volume 66, Issue 6, pp. 429-446, content of which is incorporated herein by reference in its entirety. An exemplary method for evaluating the exchange capacity or selectivity of the SICA is the "total loading-total elution" technique as described in the Examples section.

In some embodiments, the specific ion complexing agent selectively and reversibly binds a cation. It is noted that commercial resins used for cation ion-exchange comprises a styrene divinylbenzene copolymer as a substrate and have a particle size of about 0.62 mm to about 0.83 mm. The functional group is sulfonic acid with a total cation exchange capacity (CEC) of 1.8 eq/1 or 225 meq/100 grams. Typical CEC in soils from naturally occurring clays are in the range of 30-100 meq/100 grams. Humus has cation exchange capacity ranging from 100-300 meq/100 grams. In contrast, the specific ion complexing agents of the invention can have high cation exchange capacity.

In some embodiments, the specific ion complexing agent selectively and reversibly binds a cation. Such specific ion complexing agents can have cation exchange capacity (CEC) of at least 100 meq/100 grams. In some embodiments, the specific ion complexing agents disclosed herein have cation exchange capacity of 175 meq/100 grams, 200 meq/100 grams, 250 meq/100 grams, 300 meq/100 grams, 350 meq/100 grams, 400 meq/100 grams, 450 meq/100 grams, 500 meq/100 grams, 550 meq/100 grams, 600 meq/100 grams, 650 meq/100 grams or higher.

It is noted that the exact CEC employed on an agricultural site needs to be balanced with the specific objective to be accomplished on that site. For example, if ammonium, as N, is to be applied and retained at a dosage of 200 pound per acre, the SICA dosage would be 0.714 meq/100 grams of soil, including a 50% excess to retain ammonium mobilized from decay or organic and other sources of nitrogen. In some embodiments, the SICA are coupled via a coupling agent to an appropriate substrate to form a Nutrient Complexing Composition to enable the SICA to be uniformly distributed throughout the soil within contact with the rhizosphere (plant root zone) and be retained within the rhizosphere. If the coupling agent and the substrate equal 50% of the NCR, then the preferred SICA/NCC dosage is 20 mg per 100 grams of soil. If the coupling agent and the substrate equal 75% of the NCC, then the preferred SICA/NCC dosage is 40 mg per 100 grams of soil.

In some embodiments, the specific ion complexing agent selectively and reversibly binds an anion. Such specific ion complexing agents can have anion exchange capacity (AEC) of at least 100 meq/100 grams. In some embodiments, the specific ion complexing agents disclosed herein have anion exchange capacity of 150 meq/100 grams, 200 meq/100 grams, 250 meq/100 grams, 300 meq/100 grams, 350 meq/100 grams, 400 meq/100 grams, 450 meq/100 grams, 500 meq/100 grams, 550 meq/100 grams, 600 meq/100 grams, 650 meq/100 grams or higher.

It is noted that the exact AEC employed on an agricultural site needs to be balanced with the specific objective to be accomplished on that site. For example, if nitrate is to be applied and retained at a dosage of 200 pound per acre, as N, the SICA dosage would be 0.714 meq/100 grams of soil, including a 50% excess to retain nitrate mobilized from decay or organic and other sources of nitrogen. In some embodiments, the complexing functional groups are coupled via a coupling agent to an appropriate substrate to form a Nutrient Complexing Composition to enable the SICA to be uniformly distributed throughout the soil within contact with the rhizosphere (plant root zone) and be retained within the rhizosphere. If the coupling agent and the substrate equal 50% of the NCC, then the preferred SICA/NCC dosage is 20 mg per 100 grams of soil. If the coupling agent and the substrate equal 75% of the NCR, then the preferred SICA/NCR dosage is 40 mg per 100 grams of soil.

It is critical to understand the amount of exchange capacity required for an acre of plant media. By way of an example, if high yield corn is desired, the typical fertilizer application is 200 pounds of nitrogen per acre. This anticipates a yield of 200 bushels of corn per acre. 200 pounds of nitrogen per acre equals 90,800 grams of nitrogen per acre. At Nitrogen molecular weight of 14.01 grams/equivalent 6,486 equivalents are required per growing season. Table 2 compares the exchange capacities of the art known materials and an exemplary SICA of the invention.

TABLE 2

| Material | CEC/ meq/100 grams | CEC/Eq/ kilogram | Amount of material per acre | Notes |
| --- | --- | --- | --- | --- |
| Clay | 30-100 | 0.3-1 | 21,620 Kg to 6,486 Kg | High level of clay impeded infiltration rate |
| Humus | 100-300 | 1.0-3.0 | 6,486 Kg to 2162 Kg | Biodegradable thus it has a limited life |
| Rohm & Haas IR 120H | 225 | 2.25 | 2,883 Kg | Long life, reusable year after year, not resistant to fouling, expensive |
| Invention | 550 | 5.50 | 1,179.3 Kg | Long life, reusable year after year, resistant to fouling, inexpensive |

Typical plant media known in the art have a CEC in the 20 meq/100 gram range. Since this is well below the required amount of CEC required to effectively retain the cations, the un-complexed cations are subject to run-off, groundwater leaching and airborne loss. Farmers try to compensate for low CEC by multiple nutrient additions. Many cations are not effectively retained by clays and humus. Further, typical plant media has little or no ability to selectively retain cations.

Moreover, there is no discussion of anion and anion complex retention in plant media in the art. The present invention is the first to address the issue of anion and anion complex in plant media.

Prior applications of anionic polyacrylamides focused on soil erosion and not on increasing the anion or cation exchange capacity of the planting medium. The major focus was to flocculate clay particles to improve infiltration rate and drainage. Polyacrylamides are not green. Under UV light they hydrolyze to acrylamides and enter the plant roots and ultimately the food chain. This is highly undesirable due to the toxic and hazardous nature of acrylamides.

U.S. Pat. No. 4,797,145 describes improvement in the physical properties of by the application of aqueous mixtures of agricultural polyelectrolytes and polysaccharides to the soil. The combination of agricultural polyelectrolytes and polysaccharides results in greatly improving the physical properties of the soil while significantly reducing the quantity of agricultural polymers as compared to methods of the prior art.

Many plant media contain anionic charged organics. Where these anionic organics are present in high concentration they foul or block catatonically charged complexing sites which are designed to complex and retain anions. Surprisingly, the compositions, systems and methods disclosed herein can block fouling by organics, so that complexing sites are available even in high organic environments.

Many forms of nutrients and essential minerals are not cations or anions as they may For example, lead and cadmium act as anions in dilute acid chloride solutions such as exist in many plant media Similar anion complexes form in plant media with bisulfates, bicarbonate and organic acids.

Without limitations, the specific ion complexing agents can be natural or synthetic. Further, the specific ion complexing agents can be inorganic or organic. Moreover, the specific ion complexing agents can be neutral or charged. For example, the specific ion complexing agents can have a negative charge (e.g. electronegative) or a positive charge (e.g., electropositive). In some embodiments, the specific ion complexing agent is neutral.

Surprisingly, the complexing agents of different charges and different charge intensities perform more efficiently together than individually. Further, complexing agents of lower charge intensities are more effective at complexing and retaining nutrients, minerals, pesticides, herbicides, growth stimulators, hormones, water, nitrification blockers than chemical agents with higher charge intensities.

Without wishing to be bound by a theory, the reason that complexing agents of different charges and different charge intensities perform more efficiently together than individually relates to the fact that cations with some counterions act as negatively charged ions rather than positively charged ions. Conversely, anions with some counterions act as negatively charged ions. Therefore, a blend of SICA to retain both specific cations and anions perform more efficiently at selectively or specifically complexing targeted ions.

Ion strength can also be described by the electronegativity or electropositivity of ions. Electronegativity, symbol x, is a chemical property that describes the tendency of an atom or a functional group to attract electrons (or electron density) towards itself. An atom's electronegativity is affected by both its atomic number and the distance at which its valence electrons reside from the charged nucleus. The higher the associated electronegativity number, the more an element or compound attracts electrons towards it. Due to the unique specific ion complexing nature of the SICA of the invention, electronegativity/electropositivity is only one factor in selectively complexing and retaining specific ions. In application of ion exchange sorption to soils it is the predominate factor controlling which ions are exchanged over others.

Additional exemplary, factors involved in selectively complexing and retaining a desired compound or molecule include, but are not limited to, size match between desired compound and the SICA cavity, complementarity (topological and shape selectivity), desired compound and SICA charge and ion polarisability, solvent (polarity, hydrogen bonding and coordination ability, free energies of solvation of the desired compound and the SICA, compound basicity and SICA acidity or compound acidity and SICA basicity, and other kinetic, enthalpic and entropic contributions to the compound-SICA interactions.

In some embodiments, the specific ion complexing agent has a high exchange capacity. Utilization of the high specific ion complexing capacity is more effectively applied by distributing the high nutrient exchange capacity across a large area, so as plants grow and roots search for nutrients, there is increased proximity of the retained nutrients available to the plants.

Exemplary SICA include, but are not limited to small organic compounds that are able to dock into binding sites; inorganic metals that form coordinated complexes with certain substrate functionalities; and hydrophobic molecules that can bind nonpolar pockets in biomolecules. Examples of naturally occurring anion and/or cation exchange complexing agents include, but are not limited to, inorganic compounds (such as iron compounds, aluminum compounds, combinations of iron and aluminum compounds, metal compounds having anion or cation exchanging capacity (such as clays), crystalline silica and related compounds, and clinoptilolite), organic compounds (such as humic acid and humus oil), and inorganic/organic mixtures (such as digested sludge from anaerobic or aerobic waste digestion).

It is noted that, for prior art compounds to be selective and effective in binding the target nutrients and metals which are the subject of this invention, the prior art compounds would need to be reacted to their respective Lewis acid or Lewis base and assembled into the geometry and structure necessary to form single or multiple complexes which form multiple chemical bonds with SICA.

It is noted that prior art compounds can act as intermediary or temporary carriers of nutrients or metals until they are bound to SICA. Even though prior art compounds are only physical carriers of nutrients and metals they can slow down the rate of loss to runoff or groundwater until they can be chemically bound to SICA. At various times during a growth or dormant plant cycle nutrients and metals can be mineralized or released to the soil solution due to chemical or microbiological influences. Prior art compounds can be an intermediary link to and facilitating binding by SICA. Binding facilitation occurs by reduction of the binding energy or Gibbs free energy required by the SICA to chemically bond with nutrients or metals.

Examples of synthetic anion and/or cation exchange complexing agents include, but are not limited to, inorganic compounds (such as iron compounds, aluminum compounds, silica compounds, and combinations thereof), organic compounds (such as oxoacid derivatives, guanidines, ureas, amidines amino acids, creatine, saxitoxin, amides and their derivatives, amines or imines, polynuclear methylol-forming phenols, esters of acrylic and methacrylic acids, mannich reaction products, nuclear sulfonic acid radicals, aminotriazine-aldehydes, tributyl amines and their derivatives, activated carbon, charcoal, coal and carbo activatus, trimethylammonium or trialkylphosphonium molecules, carboxylic acids or carboxylates or their derivatives, nucleophilic and electrophilic alkylation derivatives and carbine alkylating derivatives, azetidinium compounds and derivatives, pyridines and derivatives.

Typical plant media known in the art has low selectivity (i.e., low selectivity coefficient) for a specific ion, molecule or compound. In other words, typical plant media known in the art non-discriminately binds cations or anions. This results in supplementing the planting media at frequent intervals and high costs. Moreover, plan media with low selectivity coefficient are environmentally unfriendly since higher amounts are needed. In contrast, SICA of the invention can complex/bind reversibly and selectively with a desired compound or molecule, such as a nutrient, micronutrient, essential mineral, pesticide, herbicide, growth simulator, growth hormone, nitrification blocker, or any combinations thereof.

As used herein, the terms "reversibly complexes", "reversibly complexes with", "reversibly binds", "reversibly binds to" or "reversibly binds with" are used interchangeably herein and mean that the two parts are linked by non-covalent bonding only. Generally such non-covalent bonding comprises one or more of hydrogen bonding, Van der Waals forces, electrostatic forces, hydrophobic forces, and the like. As such, reversible complexing does not require breaking of a covalent bond to remove or separate the SICA from the ion, molecule or compound.

In some embodiments, the SICA forms a reversible covalent bond with the compound of interest. A reversible covalent bond is chemical bond where the free energy difference separating the noncovalently-bonded reactants from bonded product is near equilibrium and the activation barrier is relatively low such that the reverse reaction which cleaves the chemical bond easily occurs.

In contrast, ion exchange bonds are ionic or non-covalent. Generally, no chemical bonds are formed between the two interacting molecules. Hence, the association is fully reversible.

The terms "selectively complexes", "selectively complexes with", "selectively binds", or "specifically binds to" or "specifically binds with" refers to the binding of a SICA to a ion, molecule or compound, and means a binding that is measurably different from a non-specific interaction. Specific binding can be measured, for example, by determining binding of SICA to a desired target ion, molecule or compound compared to binding of the SICA to a control or reference ion, molecule or compound. For example, specific binding can be determined by competition with a control or reference ion, molecule or compound that is similar to the target ion, molecule or compound. Specific binding can be exhibited, for example, by a SICA having a Kd for the target of at least about 200 nM. In some embodiments, the SICA has a Kd for the target of at least about 150 M, at least about 100 nM, at least about 60 nM, at least about 50 nM, at least about 40 nM, at least about 30 nM, at least about 20 nM, at least about 10 nM, at least about 8 nM, at least about 6 nM, at least about 4 nM, at least about 2 nM, at least about 1 nM, or greater.

Methods for determining exchange capacity are well known in the art. An example to explain the binding affinity is the binding of nitrate and chloride on SICA. Out of these two ions; nitrate has high binding affinity towards SICA and is preferentially retained over chloride (or other anions).

When nitrate is diffused towards receptor site SICA, the association constant is termed as K1 and the rate constant for backwards reaction is K−1. The binding of nitrate to the receptor R can be represented as, at equilibrium state, the concentration of product that will be equal to the concentration of reactant. Hence, $$[N][SICA]k1 = [NSICA]k-1$$

$$k1k-1k1k-1 = [NSICA][N][SICA][NSICA][N][SICA]$$

$$\text{Binding Affinity} = k1k-1k1k-1$$

$$Kd = k-1k1k-1k1$$

Here Kd is called as binding affinity constant or Kd binding affinity. Each nutrient or mineral has a unique binding affinity constant for a certain SICA system which can be used to identify distinct receptors. The high magnitude of binding affinity (large magnitude of K1) shows good binding capacity of the nutrient (or mineral) to bond with SICA. Kd, that is the equilibrium dissociation constant or binding affinity constant, is the reciprocal of the affinity. It is used to explain the binding of nutrients or minerals to a SICA receptor. The units of the SICA dissociation constant are usually millimolar. In general, SICA dissociation constants range from 0.65 mM to 0.9 mM.

Generally, the SICA has a high selectivity coefficient. As used herein, the term "selectivity coefficient" is a numerical value designating the preference of SICA forming or binding with a compound or molecule of interest versus a different compound or molecule, such as a reference compound or molecule. Generally speaking, the selectivity coefficient for the SICA of this invention can be at least 25. For example, the SICA can have a selectivity coefficient of at least 1.5, at least 2.5, at least 5, at least 10, at least 15, at least 20, at least 25, at least 30, at least 35, at least 40, at least 45, at least 50, at least 75, at least 100 or more. In some embodiments, the selectivity coefficient for the SICA is 2.5 or more. In some embodiments, a high selectivity coefficient is a selectivity coefficient of 4.0 or more.

The concept of selectivity as used in this presentation is to quantify the extent to which a given SICA A binds a co-ion, B (e.g., Cl) and nutrient C (e.g., $NO_3$). In the selectivity tests of the invention the complexes formed have 1:1 stoichiometry. Thus, the two interactions may be characterized by equilibrium constants $K_{AB}$ and $K_{AC}$ $$A + B \rightleftharpoons AB; K_{AB} = \frac{[AB]}{[A][B]}$$

$$A + C \rightleftharpoons AC; K_{AC} = \frac{[AC]}{[A][C]}$$

where [..] represents a concentration. The selectivity coefficient is defined as the ratio of the two equilibrium constants.

$$K_{B,C} = \frac{K_{AC}}{K_{AB}}$$

The selectivity coefficient is in fact the equilibrium constant for the displacement reaction $$AB + C \rightleftharpoons AC + B; K_{B,C} = \frac{[AC][B]}{[AB][C]} = \frac{K_{AC}[A][B][C]}{K_{AB}[A][B][C]} = \frac{K_{AC}}{K_{AB}}$$

The greater the selectivity coefficient, the more the nutrient C will displace the coion B from the complex formed with the SICA A. An alternative interpretation is that the greater the selectivity coefficient, the lower the concentration of C that is needed to displace B from AB. Selectivity coefficients are determined experimentally by measuring the two equilibrium constants $K_{AB}$ and $K_{AC}$.

It is noted that methods for determining selectivity coefficient are well known in the art and readily available. The usual procedures to measure selectivity factors are the separate solution method (SSM) and the fixed interference method (FIM) according to the recommendations of the International Union of Pure and Applied Chemistry. See for example, Guilbault, G. G.; Durst, R. A.; Frant, M. S.; Freiser, H.; Hansen, E. H.; Light, T. S.; E. Pungor, Rechnitz, G.; Rice, N. M.; Rohm, T. J.; Simon, W.; Thomas, J. D. R. Pure Appl. Chem. 1976, 48, 127-132, content of which is incorporated herein by reference in its entirety. With SSM the potentials measured in pure solution of the primary and of the interfering ion are compared and with FIM the primary ion activity is varied at a fixed level of interfering ion activities. Additional methods for determining selectivity coefficient are described, for example, in Bakker, E. Determination of unbiased selectivity coefficients of neutral carrier based cation-selective electrodes, Anal. Chem. 1997, 69, 1061-1069 and Sokalski, T.; Maj-Zurawska, M.; Hulanicki, A. Determination of true selectivity coefficients of neutral carrier calcium selective electrode, Mikrochim. Acta 1991, 1, 285-29, content of both of which is incorporated herein by reference in its entirety.

In some embodiments, the SICA specifically and reversibly forms a complex or binds with nutrient, micronutrient, essential mineral, pesticide, herbicide, growth simulator, growth hormone, nitrification blocker, or any combinations thereof. In some embodiments, the SICA specifically and reversibly forms a complex or binds with a nutrient, micronutrient, essential mineral, growth simulator, or growth hormone required for plant growth. In some embodiments, the SICA specifically and reversibly forms a complex or binds with nitrate, nitrite, phosphate, ammonia, ammonium, sulphates, nitrogen, phosphorous, potassium, boron, copper, iron, chloride, manganese, molybdenum, zinc, or any combinations thereof. In some embodiments, the SICA specifically and reversibly forms a complex or binds with nitrate, nitrite, phosphate, ammonia, ammonium, sulphates, nitrogen, phosphorous, or any combinations thereof. In some embodiments, the desired compound or molecule with which the SICA specifically and reversibly forms a complex or binds with is not a metal ion.

In embodiments of the various aspects disclosed herein, the SICA comprises water of hydration.

In some embodiments, the specific ion complexing agents can be in the form of a polymer. For example, monomers comprising complexing functional groups can be polymerized to form a homopolymer. In another example, monomers comprising different complexing functional groups can be polymerized to form a copolymer or blockpolymer. In some embodiments, monomers comprising functional groups, which functional groups can be converted to complexing functional groups, can be polymerized to form a homopolymer, copolymer or blockpolymer.

In some embodiments, specific ion complexing agent monomers can be polymerized to form a homopolymer. In some embodiments, the specific ion complexing agent monomers can be polymerized with a second monomer to form a copolymer, blockpolymer, or any combinations thereof. Without limitations, the second monomer can be a second specific ion complexing agent monomer disclosed herein.

The SICA disclosed herein can be very concentrated. Further, the SICA can be produced as solids including granuals, dusts, powders, fibers, liquids or in a gaseous form. The SICA can be used as concentrates or they can be formed upon a substrate which allows the actives to be effectively distributed across large surface areas. This reduces the amount of actives required to efficiently retain a specific amount or type of nutrients or essential minerals.

To address the need for broad distribution of the complexing sites in the SICA, the SICA can be manufactured as solids including fine powders, granuals and spheres, liquids and gases. Many times in order to maximize actives distribution to the location where needed by plant roots, it is beneficial to link the complexing functional group or SICA to a carrier or a substrate. Accordingly, in some embodiments, the complexing functional group or the SICA can be linked with a substrate. SICA linked with a substrate are also referred to as Nutrient Complexing Composition ("NCC") herein. Without wishing to be bound by a theory, coupling to a substrate enable the SICA to be uniformly distributed throughout the soil within contact with the rhizosphere (plant root zone) and be retained within the rhizosphere.

Without limitations, the NCR can be formulated in any desired shape or form. For example, the NCR can be in the form of a solid, liquid or gas. In some embodiments, the NCR can be in the form of solutions, long chain fibrous polymers, powders or granules. In some embodiments, the NCR is in form of a solid. In some embodiments, the NCR is in form of a particle. Without limitations, the particle can be a microparticle or a nanoparticle.

Without limitations, the SICA can be linked covalently or non-covalently with the substrate. The non-covalent interactions between SICA and the can be based on ionic interactions, van der Waals interactions, dipole-dipole interactions, hydrogen bonds, electrostatic interactions, hydrophobic interactions, shape recognition interactions, or any combinations thereof.

In some embodiments, the complexing functional group or the SICA comprising same is covalently linked with a surface of the substrate via a linker. The term "linker" means a moiety that connects together two parts, e.g., SICA and substrate. Linkers typically comprise a direct bond or an atom such as oxygen or sulfur, a unit such as $NR^1$, $C(O)$, $C(O)O$, $C(O)NR^1$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, N(R¹)₂, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

Without limitations, the linker can be of any desired length. For example, the linker can range in length from a few Angstroms (e.g., bond length) to micrometers. In some embodiments, the linker is about 200 Angstroms in length. In some embodiments, the linker is a linker formed by N-β-maleimidopropionic acid hydrazide (BMPH) or 1-ethyl-3-[3-dimethylaminopropyl]carbodiimide hydrochloride. In some embodiments, the linker is formed in situ by sodium meta-periodate or a cyanoborohydride solution (e.g., 5M $NaCNBH_3$) in 1M NaOH, Without limitations, the substrate can be natural or synthetic. Further, the substrate can be inorganic or organic. In some embodiments, the substrate comprises a reactive functional group for coupling with the specific ion complexing agent or conversion into a complexing functional group. The term "reactive functional group" refers to a functional group that is capable of reacting with another functional group or being converted into another functional group, such as a complexing functional group. Exemplary reactive functional groups include, but are not limited to, hydroxyls, amines, thiols, thials, sulfinos, carboxylic acids, amides, and the like. In some embodiments, the reactive functional group is selected from the group consisting of carboxyl-to-amine reactive groups, amine-reactive groups, sulfhydryl-reactive groups, aldehyde-reactive groups, photoreactive groups, hydroxyl-reactive groups and any combinations thereof.

Exemplary substrates include but are not limited to clay, silica, aluminum silicates, metal oxides, carbohydrates, cellulose, starches, bio-solids, proteins, single cell protein (Procell), amino acids, fats, oils, greases, plant biomass, fibrous waste from pulp and paper mills, and the like.

As used herein, the term "bio-solid" generally means sewage sledge. Wastewater treatment processes produce residuals, also called sewage sludge, as a by-product of the treatment processes. Biosolids are the nutrient-rich organic materials resulting from the treatment and processing of these residuals. The term bio-solid includes all forms of treated sewage sludge that is intended for agricultural use as a soil conditioner. Bio-solids from anaerobic digestion of municipal waste contain proteins and cellulose. The SICA can be reacted with the bio-solids to increase the distribution of the required charges across a broad area. Further, bio-solids generated from the anaerobic digestion of municipal waste contain heavy metals. These heavy metals cause the amount of bio-solids to be restricted to prevent excessive application of heavy metals to agricultural sites. The SICA can bind heavy metals thus allowing increased application of wastewater solids to agricultural sites.

Municipal wastewater bio-solids have negative value. Wastewater plants have to pay for delivery and application of the bio-solids to agricultural sites, or pay to dispose of the waste bio-solids in a landfill. Using the bio-solids as the substrate for linking with the SICA turns the municipal waste bio-solids into a safe, valuable resource, which when properly applied, can help control pollution of water ways and ground water.

In some embodiments, the substrate is oxidized bio-solid, cellulose, or Procell.

In some embodiments, the substrates is a waste product of industrial processes including sludges and dusts, municipal water and wastewater treatment sludges, including primary, secondary and tertiary treatment process solids, especially solids from aerobic and anaerobic digestion. In some embodiments, the substrate is used as is, treated before, during their waste treatment processing or after their waste treatment processing thus enhancing their suitability as complexing and retention capabilities.

Without wishing to be bound by a theory, linking a SICA to a substrate based on or derived from waste products can increase the value of the waste product. In some embodiments, linking a SICA to a substrate based on or derived from waste products reduces or inhibits leaching of toxic or hazardous substances to run-off, to ground water, evaporation or windage. Surprisingly, inventor has discovered inter alia that the SICA linked with the substrate have increased complexing and retention capacity when dilutive effect of the substrate is taken into account.

In some embodiments, the SICA is comprised in a composition wherein the composition further comprises an ion, micronutrient, nutrient, essential mineral, pesticide, herbicide, growth simulator, growth hormone, nitrification blocker, or any combinations thereof. Without limitations, the nutrient, micronutrient, essential mineral, pesticide, herbicide, growth simulator, growth hormone, nitrification blocker can be complexed or bound with the SICA or not.

In some embodiments, the SICA is comprised in a composition wherein the composition comprises two or more different SICA. For example, the two or more different specific ion complexing agents can complex with cations, anions or any combinations thereof. For example, one of the SICA can complex with cations and the other SICA can complex with anions.

In some embodiments, the SICA is comprised in a composition wherein the composition further comprises planting media. The terms "planting media" or "media" or "growth media" as used herein refer to any media that can support plant growth. The term includes soil, as well as media such as rock, wool, vermiculite, etc. The terms "soil" or "plant environment" for plants in the practice of the method of the present invention mean a support for use in culture of a plant and especially a support in which roots are to be grown. The terms are not limited in material quality, but include any material that may be used so far as a plant can be grown therein. For instance, so-called various soils, seedling mat, tapes, water or hydroponic solutions and the like can also be used. Specific examples of the material constituting the soil or cultivation carrier include, without limitation, sand, peat moss, perlite, vermiculite, cotton, paper, diatomaceous earth, agar, gelatinous materials, polymeric materials, rock wool, glass wool, wood chips, bark, pumice and the like.

In some embodiments, the method comprises incorporating two or more two or more different SICA at the planting site. Without imitations, the two or more different SICA can be applied concurrently or at separate times. For example, the two or more different SICA can be mixed together and applied together. Or, the two or more different SICA are not mixed together but applied at the same time. Alternatively, the two or more different SICA are applied at different times.

The amount of SICA or a composition comprising same in the planting media can be any desired amount. For example, the amount of SICA or a composition comprising same in the planting media can range from about 1 milligram to about 1000 metric tons per acre of planting media. In some embodiments, the amount of SICA or a composition comprising same in the planting media ranges from about 1 gram to about 1 metric tons per acre of planting media.

The compositions and methods disclosed herein can be useful on primed and unprimed seeds. Priming is a water-based process known in the art that is performed on seeds to increase uniformity of germination and emergence from a growing medium or soil, thus enhancing plant stand establishment. Without wishing to be bound by a theory, by incorporating the composition of the present invention into the priming process, the benefits of optimum seed germination, optimum growth and development, synchronized time to flower, uniform flowering, uniformity in maturity of the crop, improved yields and improved quality of the harvested crop (fruit or other plant parts) are obtained.

Surprisingly, the methods and SICA (or compositions comprising SICA) disclosed herein can release complexed and retained nutrients in response to a chemical or biochemical signal from the plant. As such, the SICA are in chemical communication with plants and release complexed and retained substances when required by plants. When a plant requires an anionic or cationic nutrient or essential mineral it emits a proton. See, for example, Campbell, N., & Reece, J. (2004). Transport in Plants. In *Biology AP Edition* (7th Edition ed., pp. 764-784). Boston: Pearson Education. Complexing sites are activated when a plant requires anions such as nitrate or neutral solutes such as sucrose.

Emitted protons indirectly displace anions from positively charged sites by reacting with carbonate, bicarbonate or carbon dioxide in the planting medium. The bicarbonate ($HCO3$) formed has greater preference for the cationically charged site thus displacing the anion making it available for diffusion into the plant through the root membrane.

The required carbon dioxide/carbonate/bicarbonate complex can be provided by plant root respiration, soil breakdown of organic, plant media or fertilizer component, or by hydrolysis by-product from urea as follows:

$$CO(NH_2)_2 + H^+ + 2H_2O \rightarrow 2NH_4^+ + HCO_3^-$$

$$HCO_3^- + H^+ \rightarrow CO_2 + H_2O; \text{ pH 6.5 to 8.0}$$

$$CO(NH_2)_2 + 2H^+ + 2H_2O \rightarrow 2NH^4 + H_2CO_3; \text{ pH} < 6.3$$

The efficiency of regulating nutrient release proportional to plant need is improved by maintaining a neutral to acid soil pH whereby there are no hydroxyl ions and limited carbonate ions present (pH less than 8.0 and alkalinity is predominately bicarbonate in equilibrium with carbon dioxide.

When a plant requires a cation such as potassium, membrane potential shifts and the cation diffuses into the cell via transport proteins. Thus, the negative charge complexing cations must enable release into the plant extracellular fluid so it is available for diffusion into the cytoplasm via the transport protein. Most essential elements and other nutrients are co-transported by hydrogen ion initiation. In these instances, the extracellular hydrogen directly displaces the cation from the exchange site. Transport of the hydrogen ion to the complexing exchange site occurs through reaction of the hydrogen ion with anions such as chloride and sulfate which forms HCl or $NaHSO_4$ (sodium bisulfate) or an organic acid when an organic salt reacts with the free hydrogen ion.

Without wishing to be bound by a theory, the method for reducing or inhibiting loss of a desired compound or molecule from a planting site reduces the loss of said compound or molecule form the planting site by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and up to 99% relative to planting site or media lacking the SICA. In some embodiments, the method for reducing or inhibiting loss from a planting site completely inhibits the loss of a desired compound or molecule from the planting site.

Surprisingly, inventor has discovered inter alia that the method of using the SICA or compositions comprising the same as disclosed herein can increase crop yield while minimizing or reducing use of nutrients, micronutrients, essential minerals, pesticides, herbicides, growth simulators, growth hormones, or nitrification blockers. Thus, also provided herein is a method for increasing crop yield. Generally, the method comprises incorporating a SICA or composition comprising same in planting media at the planting site. Without wishing to be bound by a theory, the method can increase crop yield by at least 0.01%, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.5 folds, at least 2-folds or more relative to planting site or media lacking the SICA.

Surprisingly, inventor has discovered inter alia that soil containing the SICA is capable of fixing nitrogen (nitrogen fixation) from the air and converting it to usable nitrate or ammonia. Thus, the invention also provides a method for fixing nitrogen. Generally, the method comprises contacting a SICA with a nitrogen source and thereby forming a nitrogen product. The formed nitrogen product can be removed from the SICA.

The nitrogen source includes, but is not limited to, air, air with an enhanced nitrogen content, panting media, planting media with an enhanced nitrogen content a pure nitrogen source mixed with oxygen. In some examples, the nitrogen products include nitrates and/or nitrites. The reaction conditions, such as the concentration or type of SICA used, the temperature or duration of reaction, can be selected to provide a desired result, such as to increase reaction rates, favor a particular nitrogen product, etc. . . . .

Depending upon the crop being treated, the SICA are designed to retain and release the blend of nutrients and essential minerals appropriate for the crop to be grown. The SICA or compositions comprising same can be placed in proximity to the root system anticipated throughout the growing season. One of skill in the art is well aware of the target zones for different crops. For example, corn has a target zone of approximately 24 inches. Thus, the SICA would be applied in the fall to approximately the 12-24 inch zone. Most of soybean growth occurs in the upper 12 inches of soil, if adequate soil moisture is available. Some roots surface. By Soybean Growth/Reproductive Stage R6, under favorable conditions, soybean roots can reach depths greater than 6 feet and have spread 10 to 20 inches laterally. In deep soils, the active rooting depth for spring wheat is 35 inches with a maximum of 47.2 to 59 inches; winter wheat root depth can be twice spring wheat.

Without wishing to be bound by a theory, if fall application of SICA or a composition comprising same is not feasible, spring application as side-dressing with incorporation into the soil between 4-6 inches can be acceptable. Otherwise, the SICA or a composition comprising same can be applied as top dressing.

In some embodiments, detailed soil analyses and crop biomass analyses before and after the growing season direct where supplemental retention is required. Detailed monitoring and control of the biomass during critical growth periods identifies anticipates nutrient, essential mineral deficiencies and water stress before they interfere with plant growth.

Generally, detailed soil analyses can be performed before and after growth cycles and can include all forms of nutrients and metals in the soil including free available ions and molecules as well as organically bound nutrients. The purpose is to have a detailed beginning and ending inventory of nutrients and metals available for plant growth reproduction. This beginning and ending inventory allows part of the data to enable calculation of a mass balance of nutrients and metals used in a growth/reproduction cycle.

Similar to the soil analyses, crop biomass analyses can be performed during and after growth and reproduction stages of plants and can include all forms of nutrients and metals which are essential for optimum growth and reproduction. Particular attention should be directed to crop mass which is removed from a growth site as it is a critical part of the site mass balance calculation. Stalks, leaves, roots, husks, hulls and cobs are less important analyses if they are returned to the farm land. If they are removed, they are a critical part of the mass balance analysis.

Without wishing to be bound by a theory, analysis of various plant elements including leaves and stalks/stems during the plant growth and reproduction stages can be very informative. It can identify problems which are affecting healthy plant growth. Laboratory methods to characterize biomass health include analysis for enzymes, ATP, DTP, MDP, and amino acids.

Exemplary parameters for the soil and/or crop biomass analyses include, but are not limited to, organic matter, phosphorous, potassium, magnesium and calcium, sodium, soil pH, buffer index, cation exchange capacity, percent base saturation, nitrate-nitrogen (e.g., Total Kjeldahl Nitrogen and ammonium), sulfur, zinc, manganese, iron, copper, boron, excess lime rate, soluble salts, and anion exchange capacity. It is noted that composite sampling and analysis of the finished crop can be, but is not necessarily, essential to performing a complete mass balance of the exemplary parameters listed above. While nutrient and metal concentrations will be different than that required/desired in the soil the methods for analysis of organic forms can be critical and directly applicable.

The method of implementation differs whether a substrate is employed or the SICA are to be applied in discrete solid, liquid or gaseous forms. Post season soil analyses can be used to determine how much of SICA remains and how much needs to be replaced. Without wishing to be bound by a theory, the life of the nutrient complexing compositions can exceed four years. Thus, an initial charge for a site can be implemented followed by supplemental additions based on analysis of the site, its fertilization schedule and its nutrient retention requirements.

Based on soil and plant analyses, nutrients, including macro and micro minerals, can be added as appropriate to compensate for nutrient deficiencies in the soil or plants.

In some embodiments, the exchange capacity of the soil is determined prior to a growing season. Exchange capacity can be measured by laboratory analysis for Cation and Anion Exchange Capacity according to Mehlich. Results are related to milliequivalents ("meq") per 100 grams of soil. For example, one meq/100 grams of soil of ammonium with a molecular weight of 18 would be recorded as 18 milligrams of ammonium per 100 grams. If reported as $NH_4$—N, meaning that ammonium is reported as nitrogen equivalent, as is convention in agriculture, one meq of $NH_4$—N would equate to 14 milligrams of N per 100 grams of soil.

One meq of nitrate per 100 grams of soil equals 62 mg of $NO_3$ per 100 grams of soil. One meq of $NO_3$—N would equate to 14 milligrams of N per 100 grams of soil. Since nitrate is an anion, one meq of nitrate would necessarily relate to Anion Exchange Capacity, meaning the soil has the capacity to retain one meq of nitrate.

One meq of Anion Exchange Capacity does not distinguish one anion from another. The positively charged site would have competition from all inorganic anions, e.g. chlorides, nitrates, sulfates, phosphates, bicarbonates, and carbonates. The positively charged site would also have competition from all organic negatively charged molecules and compounds.

Exchange Capacity, whether as Anion (AEC) or Cation (CEC), does not indicate selectivity for one ion or polar molecule over another. Until Exchange Capacity is further qualified as being selective for one ion or polar molecule over another it is a highly misleading term.

Soil scientists typically recommend that Cation Exchange Capacity be 10, meaning 10 meq of cations per 100 grams of soil. As nitrogen equivalent, 10 meq equals 140 mg of N per 100 grams of soil.

A highly desired cation is ammonium. If it is desired that 100 pounds of ammonium as nitrogen per acre of soil is applied and desired to be retained, 2.5 mg of ammonium-N per 100 grams of soil is desired to be retained in the soil. 2.5 mg of $NH_4$—N per 100 grams equals 0.18 Cation Exchange Capacity.

Conversely, if it is desired that 100 pounds of nitrate as nitrogen per acre of soil is applied and desired to be retained, 2.5 mg of nitrate-N per 100 grams of soil is desired to be retained in the soil. 2.5 mg of $NO_3$—N per 100 grams equals 0.18 Anion Exchange Capacity.

Farmers typically apply 100-120 pounds of ammonium-N(equal to 129-154 pounds of ammonium) per acre and 100-120 pounds of nitrate-N(equal to 443-531 pounds of nitrate) per acre to maximize corn crop yields. If the soil Cation Exchange Capacity was selective for ammonium, the CEC required would be 0.54, a far cry from the recommended 10 CEC. If the soil Anion Exchange Capacity were selective for Nitrate, AEC required would be 0.54.

Generally, the SICA or a composition comprising same will be applied to the rhizosphere or root zone of the crop or crops to be grown. Plants typically take up nutrients through their roots; thus, ideally, the complexing agents are located in the rhizosphere. Crops vary on the depth and radius of their root zone. Corn and soybeans typically have roots up to four feet in depth and a root ball 7 inches in diameter. Potatoes and edible beans typically have root depths of two feet, alfalfa root depth up to five feet. Uniform mixing of the reservoirs throughout the target root zone is practiced in the fall during plowing under of prior season's reclaimed vegetation.

Topdressing is a mix applied to the surface of the farmland. The term topdressing also is used for the process of applying the material. Topdressing nutrient complexing compositions are evenly applied in a thin layer, typically ¼ inch (6.35 mm) or less, for a variety of purposes. Topdressing can be practiced before, during and after growth and reproductive stages of the plant life cycle.

Side dressing is the application of fertilizers in a shallow furrow or band along the side of vegetable row crops or in a circle around individual plants. Side dressing gives extra nutrients to vegetable crops so that they can produce to their full potential. Side dressing of nutrient complexing compositions can be practiced before, during and after the growth and reproductive stages of plant life cycle.

In various embodiments, the SICA, when placed in and around planting media, retains ions, nutrients, essential minerals, pesticides, herbicides, growth stimulators, water and other substances, minimizing their loss to run-off, loss to ground water, loss to evaporation or loss to windage.

Without wishing to be bound by a theory, nutrients, metals and other substances on agricultural sites are water soluble; being water soluble, they are readily dissolved in rain or irrigation water. When excess water leaves a growth site either through runoff, tile drain or percolation through the ground, the substances dissolved in it are also lost from the site. The SICA which complexes and retains in plant root zone, are linked to a substrate on the agricultural site; in this manner control of loss through runoff, tile drainage or ground water percolation is achieved. Accordingly, in various embodiments, the SICA retains ions, nutrients, essential minerals, pesticides, herbicides, growth stimulators, water and other substances, minimizing their loss to run-off, loss to ground water, loss to evaporation or loss to windage.

Soil contains minimal, if any, anion exchange capacity (AEC). Limited AEC subjects nutrients and essential minerals to losses to run-off, ground water or windage. Incorporation of the SICA into plant root zones makes nutrients and essential minerals readily available when needed by plants. Since nutrients and essential minerals are available when need by plants, plants do not go into stress or cannibalize other parts of the plant to support crop production. Reduced plant stress increases plant growth. Accordingly, in various embodiments, the SICA facilitates increases or enhances transport of nutrients and essential minerals into plants. Without wishing to be bound by a theory, this can stimulate plant growth while reducing nutrient and essential mineral losses to run-off, ground water, evaporation or windage.

Some essential minerals, when present in micro-quantities catalyze important biochemical reactions within plants. The important biochemical reactions requiring trace minerals include photosynthesis, phosphorylation, Calvin Cycle, respiration, plant nutrition, plant hormone functions, tropisms, nastic movements, photomorphogenesis, circadian rhythms, environmental stress physiology, seed germination, dormancy and stomata function and transportation, and both parts of plant water relations. In various embodiments, the SICA retains nutrients and essential minerals minimizing their loss to run-off, loss to ground water, loss to evaporation or loss to windage, when present in concentrations ranging from about 1 milligram to about 1000 metric tons per acre of planting media. Without wishing to be bound by a theory, a half cubic acre of soil, containing 1000 metric tons of sand can be converted into highly fertile soil with the addition of 1000 metric tons of SICA.

In some cases, soils merely require trimming of their AEC and CEC with selective and specific ion complexing capabilities to convert it into highly fertile soil with high yields. Thus, the concentration of SICA required is directly related to the specific requirements of a given agricultural site and the need of the site to be enhanced with critical nutrients and minerals. In various embodiments, the SICA retains nutrients and essential minerals minimizing their loss to run-off, loss to ground water, loss to evaporation or loss to windage, when present in concentrations ranging from about 1 gram to about 1 metric ton per acre of planting media.

In various embodiments, the SICA facilitate transport of nutrients and essential minerals into plants, whereby crop yield is increased by at least 0.01% while nutrient and essential mineral losses to run-off, ground water, evaporation or windage is reduced.

Without wishing to be bound by a theory, supplying critical nutrients and minerals to plant root zones when they are required reduces plant stress. Reduction of plant stress can be directly related to increased crop yield In various embodiments, the SICA facilitates transport of nutrients and essential minerals into plants, whereby plant growth or crop yield is increased by at least 0.01%, nutrient, essential mineral and other supplemental chemical losses to run-off, ground water, evaporation or windage is minimized and usage of fertilizer and other supplemental chemical agents is reduced as compared to usage of fertilizer and other supplemental chemical agents without the composition of the invention. As noted-above, supplying critical nutrients and minerals to plant root zones when they are required reduces plant stress. Since fertilizer and other supplemental chemical agents are retained in the plant root zones, there is less loss to runoff, tile drain or percolation to ground water, evaporation or windage. As such, higher yields are achieved with lower reagent consumption since the optimum reagent concentration is consistently maintained and losses are reduced.

In various embodiments, the SICA complexes and retains herbicides, pesticides, growth hormones, nitrification blockers and other natural or synthetic agents in and around planting site or media while their loss to runoff, loss to ground water, loss to evaporation and loss to windage minimized, thereby reducing, inhibiting or abating pollution of waterways and ground water. Without wishing to be bound by a theory, by effectively complexing and retaining herbicides, pesticides, growth hormones, nitrification blockers and other natural or synthetic agents in the soil, pollution of waterways and ground water can be prevented thus abating pollution.

In various embodiments, the compositions disclosed herein complex with and retain water, whereby the retained water is available for usage by plants when required, and thereby minimizing water loss to runoff, ground water, evaporation and windage. Without wishing to be bound by a theory, this can reduce or abate plant stress due to insufficient water. It is noted that by increasing and retaining nutrients in their hydrated state, the available moisture for use by plants can be increased proportionately. In some embodiments, SICA, nutrients and essential minerals form coordination compounds containing from 1 to 9 molecules of water. These waters of hydration make moisture available without water logging soils. This reservoir of moisture can reduce or abate plant stress due to insufficient water In various embodiments, the SICA complexes with and retains nutrients and essential minerals in a manner which makes the nutrients and essential minerals available to plants, whereby plants receive nutrients and minerals when required. High concentrations of undissociated or freely available fertilizers and minerals cause plant roots to be damaged and plant tissues to be "burnt". These high chemical concentrations cause osmotic conditions which reverse the flow of nutrients, minerals and water from entering plants to leaving plants. In various embodiments, SICA forms association complexes with nutrients and minerals so that they do not burn or harm roots even in high concentrations. In this manner large concentrations of nutrients and minerals can be applied to agricultural sites without damage to plants yet keep the nutrients and minerals in place until needed by the plant.

In various embodiments, the SICA releases any complexed nutrients or essential nutrients in response to a plant produced stimuli, thereby making nutrients or essential minerals available to plants when nutrient or mineral is desired or needed by plant.

In various embodiments, nutrients or essential minerals are released from SICA by plant initiation of protons, which protons react with carbonates, bicarbonates or free carbon dioxide and other elements, forming chemical complexes which displace nutrients and essential minerals from complexing and retention sites making the released nutrients and minerals available in an ionic form facilitating nutrient and mineral transport into plants.

In various embodiments, the SICA is selective for specific ionic elements and compounds such that the complexing and retention capacity for same are not consumed with non-target ions or compounds which can result in loss of complexing and retention capacity for target ions or compounds.

In various embodiments, SICA is selective for specific ionic elements and compounds such that the complexing and retention capacity for same are not consumed with organics or other agents in the planting media which can result in loss of complexing and retention capacity for target ions or compounds.

In various embodiments, SICA is selective for specific ionic elements and compounds whereby the complexing and retention capacity for same are reusable for a plurality of years.

In various embodiments, complexing and retention sites, charge density and complexing filed strength in the SICA are not in competition with plant nutrient and mineral transport mechanism but rather are synergies the same.

It is noted that the SICA of the invention differ from ion exchange. To summarize, some exemplary differences between ion exchange and SICA are as follow:
  A. In ion exchange, no chemical bonds are formed between nutrients and ion exchange sites are fully reversible. In contrast, SICA form chemical bonds between nutrients and binding sites.
  B. In ion exchange, the binding forces between nutrients and ion exchange sites primarily ionic and electrostatic in nature. The binding forces between nutrients and SICA are coordinate covalent bonds for cations and hydrogen bonds for anions (chemical)
  C. In ion exchange, the selectivity or specificity of which atoms or molecules are joined to the ion exchange site depends upon its Activity Coefficient (Ion Exchange Selectivity. With SICA, binding specificity for anionic nutrients depends on hydrogen bonding, charge, dimensionality and topology; and binding specificity for cationic nutrients and metals depends on coordinate covalent bonds, charge, dimensionality and topology.
  D. (i) Ion exchange Selectivity:
    a. The selectivity coefficient KB and the separation factor $a_B$ are directly proportional to the preference of a given ion exchange resin toward different types of ions.
    b. For the same concentration of different ions the relative preference of an ion exchanger depends primarily on two factors, i.e.:
      i. ionic charge
      ii. ionic size
    c. Ions with higher valence are typically preferred by the ion exchange resin. For example a typical cationic resin has the following preference:

$Th^{4+}>Al^{3+}>Ca^{2+}>Na^+$

Similarly, an anionic resin typically has the following preference:

$PO_4^{3-}\rightarrow SO_4^{2-}\rightarrow Cl^-$— d. Exceptions are also possible as in the following case:

$SO_4^{2-}\rightarrow I^-\rightarrow NO_3^-\rightarrow CrO_4^{2-}\rightarrow Br^-$ e. Among ions having the same charge, the ions having the smallest hydrated diameter are preferred by the ion exchange media. Ions with larger hydrated diameter and are therefore preferred.
    f. The ion exchange site preference for one ion over another is also affected by the exchange media pore size.
  (ii) SICA Selectivity:
    a. The SICA selectivity coefficient is the equilibrium constant for the reaction of displacement by one SICA of another SICA in a complex with a nutrient or metal.
    b. For the same concentration of different ions the relative preference of an SICA depends primarily on four factors:
      i. Coordinate covalent or hydrogen bonding
      ii. Charge
      iii. Dimensionality
      iv. Topology
    c. Ions with higher valence do not have particular preference over lower valence ions.
    d. There are no known exceptions
    e. For every SICA there is a specific nutrient or metal and they are complementary to each other in their size and geometry. It is just like lock and key, as there is always a certain key for a lock, no other key can be fitted in a lock; in the same way each nutrient or metal has a specific shape which is complementary to a certain SICA.
    f. In SICA binding, there is no preference for one nutrient or metal based on pore size, rather strong binding occurs based on the appropriate shape of both SICA and nutrient or metal.
  E. Typical Order of Ion Exchange Preference by Cationic Ion Exchangers
    a. Monovalent cations:

$Ag^+>Cu^+>K^+>NH_4^+>Na^+>H^+>Li^+$ b. Divalent cations:

$Pb^{2+}>Hg^{2+}>Ca^{2+}>Ni^{2+}>Cd^{2+}>Cu^{2+}>Zn^{2+}>Fe^{2+}>Mg^{2+}>Mn^{2+}$ c. Trivalent cations:

$Fe^{3+}>Al^{3+}$

In contrast, SICA have no typical order of binding preference for one cation over another. It is a chemical process involving four or more factors including coordinate covalent or hydrogen bonding, charge, dimensionality and topology.
  F. Typical Order of Ion Exchange Preference by Anionic Ion Exchangers $CNS\rightarrow ClO_4\rightarrow I\rightarrow NO_3\rightarrow Br\rightarrow CN\rightarrow HSO_4\rightarrow$ $NO_2\rightarrow Cl\rightarrow HCO_3\rightarrow CH_3COO\rightarrow OH\rightarrow F$ SICA have no typical order of binding preference for one anion over another. As previously noted, it is a chemical process involving four or more factors including coordinate covalent or hydrogen bonding, charge, dimensionality and topology.
  G. An activity coefficient is a factor used in thermodynamics to account for deviations from ideal behavior in a mixture of chemical substances. Individual activity coefficients of 130 inorganic and organic ions in water at concentrations up to Γ (Gamma), 0.2 have been computed and tabulated; parameters al were calculated by various methods. Kielland, Jacob. "Individual Activity Coefficients of Ions in Aqueous Solutions" J. Am. Chem. Soc., 1937, 59 (9), pp 1675-1678.

It is noted that traditional thermodynamic activity coefficients are not applicable to SICA nutrient or metal binding. The association constant ($K_1$) also known as the binding constant (KA) between the components of complex is the ratio of the concentration of the complex divided by the product of the concentrations of the isolated components at equilibrium:

$$A + B \rightleftharpoons AB: \log K_I = \log \frac{[AB]}{[A][B]} = pK_I$$

See, for example, Smith et al., "Beyond picomolar affinities: quantitative aspects of noncovalent and covalent binding of drugs to proteins", Journal of Medicinal Chemistry 52 (2): 225-33.

H. Soils contain not only significant inorganic molecules but also significant organic molecules. Jeffrey L. Czeisler, Schrier, E. "Activity Coefficients in Aqueous Carboxylic Acid-Sodium Carboxylate Solutions." Journal of Chemical and Engineering DataVol. 14, No. 1, January 1969. Inorganic and organic molecules contained in the soil have no impact on displacing SICA bound nutrients or metals unless they have the same bonding, charge, dimensionality and topology as the bound nutrient or metal. Even then no displacement of ions occurs, only filling of unoccupied SICA bonding sites.

I. In ion exchange, activity coefficients are determined from the chemical hydration number by the entropy deficiency method of Ulich, and calculate al from this and the effective radius of the ion. SICA binding with nutrients and metals are independent of the effective radius of ions (which is the foundation for activity coefficients).

J. In ion exchange, molecules with larger activity coefficients will displace molecules with smaller activity coefficients. In contrast, inorganic and organic molecules contained in the soil have no impact on displacing SICA bound nutrients or metals unless they have the same bonding, charge, dimensionality and topology as the bound nutrient or metal. Even then no displacement of ions occurs, only filling of unoccupied SICA bonding sites. As such, SICA binding is independent of traditional activity coefficients.

K. Disadvantages of Ion Exchange in soil environment:
  a. Lack of selectivity to complex and retain specific target ions.
  b. Most ions in the soil solution will preferentially displace ammonia, potassium and nitrate causing them to be lost to runoff or leach to groundwater.
  c. Susceptibility to fouling by organic substances in the soil.
  d. Difficult to regenerate the ion exchange sites due to the typical 25% efficiency of same.
  e. Operating capacity is 50% or less of theoretical capacity due to inability to elute competitive co-ions.

K. Advantages of SICA in soil environment:
  a. High electivity to complex and retain specific target ions
  b. Few ions in the soil, if any, will preferentially displace ammonia, and nitrate causing them to be lost to runoff or leach to groundwater.
  c. There is low susceptibility to fouling by organic substances in the soil
  d. Regeneration efficiency is 90% or better due to high affinity of SICA for specific nutrients or metals.
  e. Operating capacity of SICA is 90% or better due to lack of competitive co-ions in SICA binding sites.

Further, ion exchange resins are not technically and/or economically feasible for use in large applications such as farms. The ion exchange resins of the prior art require 8 to 49 time's normal nutrient dosage as compared the methods and compositions of the invention to obtain plant growth improvements. In addition, the amount of ion exchange resin required to combine with recommended level of nitrogen ranges from a low of 1,716 and 10,296 cubic feet per cubic acre. This compares to the nitrogen complexing dosage of 250 cubic feet per cubic acre according to an embodiment of the invention.

Further, soils contain numerous natural ion exchangers including clays, metal oxides, layered double hydroxides, and polar organics. Almost all are anionically charged with the effect of binding cations. Universally, natural and synthetic ion exchange media have poor selectivity for ions especially ammonia, nitrate and phosphorous. Natural ion exchange media overcomes poor selectivity high large quantities of non-selective capacity. Moreover, there is no control of nutrient runoff, reduction in fertilizer usage, controlled release of nutrients upon biochemical signal from plants or increase in crop yield due to retention of nutrients and essential minerals in root rhizosphere with ion exchange resins. As such, use of ion exchange resins in large scale agricultural applications is not technically efficacious nor an economical means of controlling nutrient runoff while increasing crop yield and reducing fertilizer.

In contrast to ion exchange, the methods and compositions of the invention do not employ ion exchange processes or technology to bind nutrients within the soil. Rather, the methods and compositions of the invention use specific ion complexing agents (SICA). SICA use coordination chemistry. SICA comprises functional group that binds to a nutrient to form a coordination complex. The bonding between nutrients and SICA generally involves formal donation of one or more of the SICA's electron pairs. The nature of the nutrient-SICA bonding ranges from covalent to ionic. Furthermore, the nutrient-SICA bond order can range from one to three. Nutrients are generally viewed as Lewis bases but sometimes can involve Lewis acidic nutrients. Nutrients are bound to SICA in virtually all circumstances. SICA in a complex dictate the reactivity of the central atom, including SICA substitution rates, the reactivity of the SICA themselves, and redox. SICA selection is a critical consideration in forming nutrient specific or highly selective complexes. SICA are classified by the specific nutrient ion being complexed. SICA bind nutrients through multiples sites, usually because the SICA binds pairs on more than one atom. Complexing SICA can be formed by linking donor groups via organic linkers.

Table 3 presents a comparison of ion exchange resin combination of nutrients versus the methods and compositions of the invention.

TABLE 3

Comparison of IX Resin Combination of Nutrients Approach versus Specific Ion Complexing Technology of the invention

| Feature/Benefit | Ion Exchange Resin | ASI Specific Ion Complex | Comments |
|---|---|---|---|
| Areas of application | Applicable for plants grown indoors or greenhouses | Applicable for all application including farming | Designed to reduce labor related to fertilizer applications |
| Salt leaching from growth site | Salt related anion or cation is removed prior to application of resin/nutrient complex | Salt related anion or cation is not applied unless desired | In farming applications salt concentration is not an issue |
| Nutrient Leaching from growth site | Resin combined nutrients are displaced from exchange sites and lost through runoff | Nutrients remain complexed until required by plants; thus, loss through runoff is controlled | IX Resin selectivity is broad; ASI Specific Ion complex is narrow |
| Plant Growth Improvement | 30 to 90% Improvement | 30 to 90% Improvement | IX Resin growth improvement is compared to poor soil; ASI is compared to average soil |
| Fertilizer Usage | 8 to 49 times normal as applied; 16 to 98 times normal including regeneration losses | Same as normal; there are not regeneration losses | This is not cost effective |
| Exchange Media Usage | 1,716 to 10,296 $ft^3$ per $Acre^3$ | 250 $ft^3$ per $acre^3$ | Just for nitrogen |
| Pre-reaction of exchange media with fertilizer prior to application | Yes | Optional either before or after application to farmland | Pre-reaction is more labor intensive and costly for farmers |
| Release of nutrient from exchange media | Indiscriminate, causing nutrient contamination of runoff | Based on biochemical signal from plant | Precise targeted release of nutrients |
| Reusability of exchange media | No | Yes, able to complex nutrients mobilized by microbe activity and airborne fixation of nitrogen | Without ability to complex microbe induced nutrients nutrient loss to runoff causes pollution and loss of value |
| Exchange media and nutrient usage cost effectiveness | IX Resin is cost prohibitive | ASI cost results in net savings | |

Table 4 presents a comparison of ion exchange versus SICA.

TABLE 4

Comparison of ion exchange versus SICA

| Characteristic | Ion Exchange | SICA |
|---|---|---|
| Specificity | Depending on the nutrient and soil composition, specificity ranges from 25-33% | Generally 90% or better. |
| Affinity | Depending on the nutrient and the soil composition affinity weak affinity is formed with ion exchange media and nutrients | SICA from strong affinity bonds with nutrient under soil solution conditions |
| Stoichiometry | The operating capacity of ion exchange sites are bound with multiples molecules which reduce effective exchange capacity to less than 50% | Generally 90% or better |
| Cooperativity | Non-cooperative to negative | Positive |
| Reversible vs. Irreversible Binding | Ion exchange sites can become bound with non-exchangeable molecules in soil conditions | Reversible in soil conditions |
| Kinetics | Physical equilibrium | Generally, Chemical First Order Rate of reaction |
| Bonding Mechanism | Physical—electrostatic | Covalent |
| Toxicity | Divinylbenzene styrene polymers are toxic | All green and totally biodegradable except when inorganic SICA are used. |

TABLE 4-continued

Comparison of ion exchange versus SICA

| Characteristic | Ion Exchange | SICA |
|---|---|---|
| Particle Size | 1-10 millimeters | 1-10 micrometers |
| Life | Short due to fouling | 5 years |
| Cost Effectiveness | Not cost effective see patent examination and analysis | When amortized over 5 years, SICA payback in 6 months. |
| Ease of Application | Poor | In process development |

In addition to the above, exemplary differences between ion-exchange and SICA can be summarized as follows:
1. Ion Exchange ("IX") is a physical process; SICA is a chemical process
2. IX follows a monotonic trend; SICA follows peak preference
3. IX has little geometrical preference; SICA is geometry sensitive
4. In IX solvation is important; SICA is shielded from solvent
5. In IX there is no encapsulation of nutrients; SICA encapsulates nutrients
6. IX employs simple bonding between functional group and nutrient; SICA employs multifunctional bonding and binding with nutrients.

In some embodiments, SICA can be characterized as follows:

Outer-Sphere SICA: SICA that are directly bonded to the nutrient (that is, share electrons), form part of the first coordinating sphere and could be called "inner-sphere SICA. "Outer sphere" SICA are not directly attached to the nutrient, but are bonded, generally weakly, to the first coordination shell, affecting the inner sphere in subtle ways. The complex of the nutrient with the inner sphere SICA is then called a coordination complex, which can be neutral, cationic, or anionic. The complex, along with its counterions, if required, is a coordination compound.

Trans-Spanning SICA: Trans-spanning SICA are dual bonding SICA that span coordination positions on opposite sides of a coordination complex.

Ambi-Bonding SICA: SICA such as those comprising SCN—, that can bond to a nutrient central atom through either of two or more donor atoms.

Poly-Functional SICA: Poly-functional SICA can bond to a nutrient through different SICA atoms to form various isomers.

Bridging SICA: A bridging SICA links two or more nutrient ion centers.

Nutrient-SICA Multiple Bond: Some SICA can bond to a nutrient ion center through the same atom but with a different number of lone pairs. The bond order of the nutrient-SICA bond can be in part distinguished through the nutrient-SICA bond angle. This bond angle is often referred to as being linear of bent with further discussion concerning the degree to which the angle is bent. For example, an imido SICA, in the ionic form has three lone pairs. One lone pair is used as a sigma X donor; the other two lone pairs are available as L type pi donors. If both lone pairs are used in pi bonds then the Nutrient-SICA bond geometry is linear. However, if one or both these lone pairs is nonbonding then the nutrient-SICA bond angle is bent and the entent of the indicates how much pi bonding there may be. $\eta^1$ nitric oxide can coordinate to a nutrient ion center in linear or bent manner.

Passive-SICA: Passive-SICA is a tightly coordinating multiple bonding SICA that does not participate in chemical reactions but removes actives sites on a nutrient. Passive-SICA influence the reactivity of the nutrient center to which they are bound.

In another aspect, the invention provides a composition comprising a specific ion complexing agent.

In some embodiments, the composition disclosed herein, when placed in and around planting media, retains nutrients, essential minerals, pesticides, herbicides, growth stimulators, water and other substances, minimizing their loss to run-off, loss to ground water, loss to evaporation or loss to windage.

In some embodiments, the composition disclosed herein, retains nutrients, essential minerals, pesticides, herbicides, growth stimulators, water and other substances, minimizing their loss to run-off, loss to ground water, loss to evaporation or loss to windage.

In some embodiments, the composition disclosed herein facilitates, increases or enhances transport of nutrients and essential minerals into plants. Without wishing to be bound by a theory, this can stimulate plant growth while reducing nutrient and essential mineral losses to run-off, ground water, evaporation or windage.

The composition can be formulated in any desired shape or form. For example, the composition can be in the form of a solid, liquid or gas. In some embodiments, the composition can be in the form of solutions, long chain fibrous polymers, powders or granules.

In some embodiments, the composition is in form of a solid. In some embodiments, the composition is in form of a particle. Without limitations, the particle can be a microparticle or a nanoparticle.

In some embodiments, the composition further comprises an ion, nutrient, micronutrient, essential mineral, pesticide, herbicide, growth simulator, growth hormone, nitrification blocker, or any combinations thereof. Without limitations, the ion, nutrient, micronutrient, essential mineral, pesticide, herbicide, growth simulator, growth hormone, nitrification blocker can be complexed or bound with the SICA or not.

In some embodiments, the composition further comprises planting media.

In some embodiments, the composition comprises two or more different specific ion complexing agents. For example, the two or more different specific ion complexing agents can complex with cations, anions or any combinations thereof. For example, one of the SICA can complex with cations and the other SICA can complex with anions.

Without wishing to be bound by a theory, the composition disclosed herein, when placed in and around planting media, retains nutrients, essential minerals, pesticides, herbicides, growth stimulators, water and other substances, minimizing their loss to run-off, loss to ground water, loss to evaporation or loss to windage. Thus, in another aspect, the invention provides a method for reducing or inhibiting loss of chemicals from a planting site. Generally, the method comprises incorporating a SICA or composition comprising same in planting media at the planting site. Exemplary chemicals can include, but are not limited to, nutrients, micronutrients, essential minerals, pesticides, herbicides, growth simulators, growth hormones, nitrification blockers, and the like.

In various embodiments, the compositions disclosed herein, when placed in and around planting media, retain nutrients, essential minerals, pesticides, herbicides, growth stimulators, water and other substances, minimizing their loss to run-off, loss to ground water, loss to evaporation or loss to windage.

In various embodiments, the compositions disclosed herein retain nutrients and essential minerals minimizing their loss to run-off, loss to ground water, loss to evaporation or loss to windage.

In various embodiments, the compositions disclosed herein retain nutrients and essential minerals minimizing their loss to run-off, loss to ground water, loss to evaporation or loss to windage, when present in concentrations ranging from about 1 milligram to about 1000 metric tons per acre of planting media.

In various embodiments, the compositions disclosed herein retain nutrients and essential minerals minimizing their loss to run-off, loss to ground water, loss to evaporation or loss to windage, when present in concentrations ranging from about 1 gram to about 1 metric ton per acre of planting media.

In various embodiments, the compositions disclosed herein facilitate transport of nutrients and essential minerals into plants, whereby crop yield is increased by at least 0.01% while nutrient and essential mineral losses to run-off, ground water, evaporation or windage is reduced.

In various embodiments, the compositions disclosed herein facilitate transport of nutrients and essential minerals into plants, whereby plant growth or crop yield is increased by at least 0.01%, nutrient, essential mineral and other supplemental chemical losses to run-off, ground water, evaporation or windage is minimized and usage of fertilizer and other supplemental chemical agents is reduced as compared to usage of fertilizer and other supplemental chemical agents without the composition of the invention.

In various embodiments, the compositions disclosed herein complexes and retains herbicides, pesticides, growth hormones, nitrification blockers and other natural or synthetic agents in and around planting site or media while their loss to runoff, loss to ground water, loss to evaporation and loss to windage minimized, thereby reducing, inhibiting or abating pollution of waterways and ground water.

In various embodiments, the compositions disclosed herein complex with and retain water, whereby the retained water is available for usage by plants when required, and thereby minimizing water loss to runoff, ground water, evaporation and windage. Without wishing to be bound by a theory, this can reduce or abate plant stress due to insufficient water is abated.

In various embodiments, the compositions disclosed herein complex with and retain nutrients and essential minerals in a manner which makes the nutrients and essential minerals available to plants, whereby plants receive nutrients and minerals when required.

In various embodiments, the compositions disclosed herein release any complexed nutrients or essential nutrients in response to a plant produced stimuli, thereby making nutrients or essential minerals available to plants when nutrient or mineral is desired or needed by plant.

In various embodiments, nutrients or essential minerals are released from complexing sites in the compositions disclosed herein by plant initiation of protons, which protons react with carbonates, bicarbonates or free carbon dioxide and other elements, forming chemical complexes which displace nutrients and essential minerals from complexing and retention sites making the released nutrients and minerals available in an ionic form facilitating nutrient and mineral transport into plants.

In various embodiments, complexing and retention sites in the compositions disclosed herein are selective for specific ionic elements and compounds such that the complexing and retention capacity for same are not consumed with non-target ions or compounds which can result in loss of complexing and retention capacity for target ions or compounds.

In various embodiments, complexing and retention sites in the compositions disclosed herein are selective for specific ionic elements and compounds such that the complexing and retention capacity for same are not consumed with organics or other agents in the planting media which can result in loss of complexing and retention capacity for target ions or compounds.

In various embodiments, complexing and retention sites in the compositions disclosed herein are selective for specific ionic elements and compounds whereby the complexing and retention capacity for same are reusable for a plurality of years.

In various embodiments, complexing and retention sites, charge density and complexing filed strength in the compositions disclosed herein are not in competition with plant nutrient and mineral transport mechanism but rather are synergies the same.

Without wishing to be bound by a theory, the following features of the compositions, methods and systems disclosed herein are beneficial over prior art.

1. Nutrient complexing including essential minerals and particularly anions and anion complexes: Many nutrients and their complexes are anions; there are no anion complexing agents employed at this time.
2. Metering of nutrients and essential minerals proportional to plant demand: Availability is under plant's control.
3. Increased crop yields
4. Able to retain water for use by plants during dry spells
5. Potential to reduce nutrient and essential mineral losses through run-off, ground water and evaporation.
6. The technology fits with precision agriculture; chemical additions and requirements are predicted before, during and after the growing season. Thus, yield and cost performance for a given season is more predictable.
7. Able to monitor and control nutrient, essential mineral and water sufficiency during the growing season so corrective action can be taken before growth inhibition occurs.

In various embodiments, the compositions disclosed herein, when placed in and around planting media, retain nutrients, essential minerals, pesticides, herbicides, growth stimulators, water and other substances, minimizing their loss to run-off, loss to ground water, loss to evaporation or loss to windage.

Exemplary embodiments of the various aspects disclosed herein can be described by one or more of the following numbered paragraphs:

1. A method for reducing or inhibiting Joss of a desired compound or molecule from a planting site comprising incorporating a specific ion complexing agent (SICA) at the planting site, wherein said specific ion complexing agent forms a coordination complex with the desired compound or molecule and specifically and reversibly retains the desired compound or molecule thereby minimizing the loss of said compound or molecule to run-off, ground water, evaporation or windage.
2. A method of increasing crop yield, the method comprising incorporating a specific ion complexing agent in planting media used for growing a crop, wherein said specific ion complexing agent forms a coordination complex with a desired compound or molecule and specifically and reversibly retains the desired compound or molecule.
3. The method of paragraph 1 or 2, wherein the said specific ion complexing agent is applied in a range of about 1 milligram to about 1000 metric tons per acre of planting media.
4. The method of any one of paragraphs 1-3, wherein the said specific ion complexing agent is applied in a range of about 1 gram to about 1 metric tons per acre of planting media.
5. The method of any one of paragraphs 1-4, wherein said specific ion complexing agent releases the desired compound or molecule in response to a biochemical signal from a plant.
6. The method of paragraph 5, wherein said biochemical signal is a proton.
7. The method of any one of paragraphs 1-6, wherein said desired compound or molecule is an ion, nutrient, micronutrient, essential mineral, pesticide, herbicide, growth simulator, growth hormone, nitrification blocker, or any combinations thereof.
8. The method of paragraph 7, wherein said desired compound or molecule is nitrate, nitrite, ammonium, phosphate, sulfate, or any combinations thereof.
9. The method of any one of paragraphs 1-8, wherein the specifk ion complexing agent has water of hydration.
10. The method of any one of paragraphs 1-9, wherein the specific ion complexing agent is polymeric.
11. The method of any one of paragraphs 1-10, wherein specific ion complexing agent is linked with a substrate.
12. The method of paragraph 11, wherein the specific ion complexing agent is covalently linked with the substrate via a linker.
13. The method of paragraph 11, wherein the specific ion complexing agent is non-covalently with the solid-substrate.
14. The method of any one of paragraphs 11-13, wherein the solid-substrate comprises at least one functional group for coupling with the specific ion complexing agent.
15. The method of any one of paragraphs 11-14, wherein the substrate is selected from the group consisting day, silica, aluminum silicates, metal oxides, carbohydrates, cellulose, starches, bio-solids, proteins, single cell protein (Procell), amino acids, fats, oils, greases, plant biomass, fibrous waste from pulp and paper mills, and any combinations thereof.
17. The method of any one of paragraphs 1-15, wherein the specific ion complexing agent is applied as a liquid, solid or gas.
18. The method of paragraph 17, wherein the solid is in form of a particle.
19. The method of paragraph 18, wherein the particle is: spherical, rod, elliptical, cylindrical, or disc.
20. The method of paragraph 19, wherein the particle has a size in range from about 1 nm to about 100,000 micrometers.
21. The method of any one of paragraphs 1-20, wherein the specific ion complexing agent is selected from the group consisting of small organic molecules, inorganic metals, hydrophobic molecules that bind nonpolar pockets in biomolecules.
22. The method of any one of paragraph 1-21, wherein the specific ion complexing agent comprises a functional group selected from the group consisting of sulfonic, carboxylic, carboxylate, hydroxyl, halogen, carbonyl, haloformyl, carbonate, alkoxy, acetal, hemiacetal, ketal, hemiketal, amide, amine, primary amine, secondary amine, tertiary amine, quaternary amine, primary ketamine, secondary ketamine, primary aldimine, secondary aldimine, imide, azide, azo, nitrate, nitlile, isonitrile, cyanate, isocyanate, nitro, nitroso, sultbydryl, sulfide, disulfide, sulfinyl, sulfonyl, sulfino, sulfo, isothiocyanate, carbonothioyl, phosphino, phosphono, phosphate, borono, boronate, borino, borinate, and any combinations thereof
23. The method of any one of paragraphs 1-22, wherein the specific ion complexing agent comprises a functional group selected from the group consisting of amidine, acetamidine, benzamidine, guanidine, imine, amides, sulfonic and carboxylic group.
24. The method of any one of paragraphs 1-23, wherein the specific ion complexing agent is formulated in a composition, wherein the composition further comprises a nutrient, micronutrient, essential mineral, pesticide, herbicide, growth simulator, or any combinations thereof
25. The method of paragraph 24, wherein the specific ion complexing agent is complexed with said nutrient, micronutrient, essential mineral, pesticide, herbicide or growth simulator.
26. The method of any one of paragraphs 1-25, wherein the specific ion complexing agent is formulated in a composition, wherein the composition further comprises planting media.
27. The method of any one of paragraphs 1-26, wherein the specific ion complexing agent has an ion exchange capacity of at least 100 meq/100 grams.
28. The method of any one of paragraphs 1-27, wherein the specific ion complexing agent has an anion exchange capacity of at least 150 meq/100 grams.
29. The method of any one of paragraphs 1-27, wherein the specific ion complexing agent has a cation exchange capacity of at least 150 meq/100 grams.
30. The method of any one of paragraphs 1-29, wherein the specific ion complexing agent has a selectivity coefficient of at least 1.5 for the desired compound or molecule.
31. A composition comprising a specific ion complexing agent, wherein the specific ion complexing agent binds specifically and reversibly with a compound or molecule of interest to form a coordination complex.
32. The composition of paragraph 31, wherein said desired compound or molecule is an ion, nutrient, micronutrient, essential mineral, pesticide, herbicide, growth simulator, growth hormone, nitrification blocker, or any combinations thereof
33. The composition of paragraph 32, wherein said desired compound or molecule is nitrate, nitrite, ammonium, phosphate, sulfate, or any combinations thereof.
34. The composition of any one of paragraphs: 31-33, wherein the specific ion complexing agent has an ion exchange capacity of at least 100 meq/100 grams.
35. The composition of any one of paragraphs 31-34, wherein the specific ion complexing agent has an anion exchange capacity of at least 150 meq/100 grams.
36. The composition of any one of paragraphs 31-34, wherein the specific ion complexing agent has a cation exchange capacity of at least 150/100 grams.

37. The composition of any one of paragraphs 31-36, wherein the specific ion complexing agent has a selectivity coefficient of at least 1.5 for said desired compound or molecule.
38. The composition of any one of paragraphs 31-37, wherein the specific ion complexing agent is polymeric.
39. The composition of any one of paragraphs 31-38, wherein specific ion complexing agent is linked with a substrate.
40. The composition of paragraph 39, wherein the specific ion complexing agent is covalently linked with the substrate via a linker.
41. The composition of paragraph 39 or 40, wherein the specific ion complexing agent is non-covalently with the solid-substrate.
42. The composition of any one of paragraphs: 39-41, wherein the solid-substrate comprises at least one functional group for coupling with the specific ion complexing agent.
43. The composition of any one of paragraphs: 39-42, wherein the substrate is selected from the group consisting clay, silica, aluminum silicates, metal oxides, carbohydrates, cellulose, starches, bio-solids, proteins, single cell protein (Procell), amino acids, fats, oils, greases, plant biomass, fibrous waste from pulp and paper mills, and any combinations thereof.
44. The composition of any one of paragraphs 31-43, wherein the composition is in form of a liquid, solid or gas.
45. The composition of paragraph 44, wherein the composition is in form of a particle.
46. The composition of paragraph 45, wherein the particle is spherical, rod, elliptical, cylindrical, or disc.
47. The composition of paragraph 46, wherein the particle has a size in range from about 1 nm to about 100,000 micrometers.
48. The composition of any one of paragraphs 31-48, wherein the specific ion complexing agent is selected from the group consisting of small organic molecules, inorganic metals, hydrophobic molecules that bind nonpolar pockets in biomolecules.
49. The composition of any one of paragraphs 31-49, wherein the specific ion complexing agent comprises a functional group selected from the group consisting of sulfonic, carboxylic, carboxylate, hydroxyl, halogen, carbonyl, haloformyl, carbonate, alkoxy, acetal, hemiacetal, ketal, hemiketal, amide, amine, primary amine, secondary amine, tertiary amine, quaternary amine, primary ketamine, secondary ketamine, primary aldimine, secondary aldimine, imide, azide, azo, nitrate, nitrile, isonitrile, cyanate, isocyanate, nitro, nitroso, sulfllydryl, sulfide, disulfide, sulfinyl, sulfonyl, sulfino, sulfo, isothiocyanate, carbonothioyl, phosphino, phosphono, phosphate, borono, boronate, borino, borinate, and any combinations thereof.
51. The composition of any one of paragraphs 31-50, wherein the specific ion complexing agent comprises a functional group selected from the group consisting of amidine, acetarnidine, benzarnidine, guanidine, irnine, amides, sulfonic and carboxylic group.
52. The composition of any one of paragraphs 31-51, wherein the specific ion complexing agent has water of hydration.
53. The composition of any one of paragraphs 31-52, wherein the composition further comprises a nutrient, micronutrient, essential mineral, pesticide, herbicide, growth simulator, or any combinations thereof
54. The composition of any one of paragraphs 31-53, wherein the composition further comprises planting media.
55. The composition of paragraph 54, wherein the composition comprises the specific ion complexing agent in a range from about 1 milligram to about 1000 metric tons per acre of planting media.
56. The composition of paragraph 55, wherein the composition comprises the specific ion complexing agent in a range from 1 gram to 1 metric tons per acre of planting media.
57. A planting media comprising a composition of any one of paragraphs 31-56.
58. The planting media of paragraphs 57, wherein the composition of any one of is present in an amount from about 1 milligram to about 1000 metric tons per acre of planting media.
59. The planting media of paragraph 58, wherein the composition is present in an amount from about 1 gram to about 1 metric ton per acre of planting media.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Synthesis of Exemplary SICA Composition Material

One thousand pounds of anaerobically digested bio-solids were charged in a stainless steel mixing tank equipped with an agitator drive. A monomer solution prepared from 500 lbs of a 63% solids aqueous solution of N,N-diallyl-N,N-dimethyl-ammonium chloride, 90 lbs of a 35% solids aqueous solution of cocoamidopropyl betaine, and 10 lbs sodium persulfate was sprayed on to the bio-solids in the tank and the resulting mixture agitated to thoroughly impregnate the bio-solids.

The tank was then purged with nitrogen for 1 hour and the reaction mass heated to 70° C. and held for 6 hours until the residual monomer concentration was less than 3%. Then 13 lbs of dry sodium phosphate was added and mixed for 30 minutes to a pH of 6.5-7.5. The cake was then transferred to a fluid bed drier and dried at 120° F. for 2 hours to a moisture level of less than 7%. The product was screened through a 30 mesh screen, overs ground and rescreened.

On analysis, the treated bio-solids had percent nitrogen of 1.8 to 2.4, and a percent monomer conversion of 84 to 88%. Cation Exchange Capacity of the treated bio-solids was found to exceed 2.0 EQ/Kg of bio-solids. Cation Exchange Capacity of cross-linked actives without the bio-solids was 5.7 EQ/Kg.

Example 2: Synthesis of Exemplary SICA Composition Material

At room temperature, a mixture consisting of: 250 ml of dimethyl acetamide, 79.5 g of 2,4,6, tri-dimethyl aminomethyl phenol, and 16.5 g of sodium methalate was mixed and held for 30 minutes. Thereafter, the mixture was stirred at 80° C. for 20 hours. After the mixture was cooled, the liquid portion was removed by siphon and the remaining solid portion was washed with water several times, treated with 4% HCL and 55 NaOH, washed and neutralized. The polymer product was 95 ml.

Nitrate Exchange Capacity of the finished polymer was 5.5 EQ/Kg.

Example 3: Synthesis of Exemplary SICA Composition Material

One hundred grams of biosolids was oxidized by slurrying the biosolids with 2000 milliliters of 0.05M sodium metaperiodate solution at ambient temperature for 1 to 6 hours. (The reaction time with the oxidizing agent was varied from 1 to 6 hours to alter the sulfonic content and degree of substitution.) At the end of the oxidation reaction, the bio-solids were washed with distilled water to free it from unreacted reagents and byproducts. For this washing step, water having a pH of 8 or greater should be avoided because dialdehyde oxycellulose degrades at alkaline pH.

The resulting oxidized bio-solids was then treated with 2000 milliliters of a 5 percent aqueous solution of sodium bisulfite at 60° C. for 3 hours. This amount of sodium bisulfite is far in excess of the stoichiometric amount required for sulfonation. The pH of the reaction solution was approximately 4.5. The sulfonated biosolids was thoroughly washed with distilled water to remove unreacted bisulfite.

Table 5 illustrates changes in level of sulfonation with changes in oxidant reaction time. The sulfur content of the treated pulps was determined by elemental sulfur analysis and is expressed as a weight percent of the biosolids. The sulfonic content (percent) is 2.5 times the percent sulfur content, while the DS is 0.05 times the percent sulfur content. In addition to elemental sulfur analysis, energy dispersive x-ray (EDX) analysis was used to confirm the presence of sulfur in the sulfonated pulps.

Ammonia Exchange Capacity of the sulfonated Biosolids was 1.7 EQ/Kg.

TABLE 5

| Sample No. | Time of Oxidation | Time of Sulfonation | Sulfur Content (Percent) | Sulfonic Content % | Degree of Substitution (DS) |
|---|---|---|---|---|---|
| 1 | 1 hour | 3 hours | 0.4 | 1.0 | 0.2 |
| 2 | 3 hours | 3 hours | 0.56 | 1.4 | 0.3 |
| 3 | 6 hours | 3 hours | 1.25 | 3.1 | 0.6 |

Example 4: Synthesis of Exemplary SICA Composition Material

One part of tetra-allyl ammonium bromide, 0.094 part of formamide and 0.022 part of 60% t-butyl hydroperoxide were mixed and placed in an oven at 75° C. The mixture became dark brown and glassy within ten minutes. The temperature was held at 75° C. for twenty hours. The polymer was washed with hot water, a granular water insoluble being obtained. A yield of 76% was obtained. It was transformed into the hydroxide form with 1% sodium hydroxide. Similar results were obtained using water as a solvent.

Nitrate Exchange Capacity of the polymerized unsaturated quaternary ammonium salt as produced above was 2.2 EQ/Kg. When the particle size of the polymer was reduced to 0.1 mm the Nitrate Exchange Capacity for the mass was increased to 5.6 EQ/Kg.

Example 5: Synthesis of Exemplary SICA Composition Material 122 parts of Guanidine Nitrate and 324 parts of 37% formaldehyde in water is mixed while adjusting the pH to 9-10 with 30.5 parts of soda ash. The solution is refluxed for 1-2 hours and then acidified at 80° C. with 30 parts of concentrated hydrochloric acid (37% HCl in water). The syrup gels almost immediately to a white opaque mass. This is ground to pea size, air-dried about 24 hours and then dried overnight at about 60-65° C. It is cured at a slightly higher temperature, e.g. about 100° C. The product formed is again ground to <0.1 mm and washed with caustic solution. The resin is extremely insoluble and highly anion-active.

Nitrate Exchange Capacity of the aminotriazine-aldehyde condensation product was 5.4 EQ/Kg.

Example 6: Synthesis of Exemplary SICA Composition Material 1890 parts of tetraethylene pentamine (30 mols) is charged into a suitable reaction vessel provided with agitator and a means for cooling the vessel. 4,500 parts of water are added to the tetraethylene pentamine and the resulting solution is cooled to about 3° C. 2,776 parts of epichlorohydrin is added slowly over a period of 30-70 minutes or more while the reacting mixture is being continuously agitated. After all the epichlorohydrin has been added the resulting syrup is maintained at a temperature below 10° C. for 1½ hours or more. The syrup is then permitted to warm up to about room temperature over a period of 45 minutes or more, and 200 parts of sodium hydroxide dissolved in 1000 parts of water is added. The resulting solution is heated for example by passing steam into a jacket surrounding the reaction vessel for 5 minutes thereby causing the syrup to gel. The gel is broken up in small pieces and cured in trays placed in an oven at a temperature between 95-105° C. for 17-18 hours. The cured resin is ground and screened and the 200-400 mesh is placed in a suitable bed through which 0.004 N, sulfuric acid and 0.002 N. HCl is passed.

The Anion Exchange Capacity of the finely divided particles is 5.6 EQ/Kg.

Example 7: Crop Yield Improvement with Some Exemplary Nutrient Complexing Compositions The major ion causing dead zones in lakes and oceans is nitrate. For this reason, the major nutrient studied in this example is nitrate. Nitrate comes directly from nitrate in fertilizers, oxidation of ammonia or mineralization of organic nitrogen in plant matter. All nitrogen containing fertilizers dosages are compared on the amount of elemental nitrogen contributed by it. This example uses N (nitrogen) equivalent as is conventional within the fertilizer industry when referring to multiple sources of nitrogen contribution.

In the spring of 2015, the inventors implemented a pilot plant in western Peoria County, Illinois. The purpose of the pilot plant was to demonstrate the technical efficacy of ASI's specific ion complexing agents in retaining nutrients on agricultural sites and increasing corn crop yields while controlling nutrient pollution of waterways and reducing fertilizer usage Background The pilot plant contained 168 rows of corn 45 feet long. Spacing between rows was 30 inches; spacing between each seed planted was approximately 7 inches. Seeds were planted at a density of 31,000 seeds/acre. The total experimental area was 0.37 acres. The total control area was 0.06 acre. The experimental area was divided into six sections. Each control and experimental section was divided into four subsections. Each subsection was divided into six rows 45 feet in length.

The subsections within each section were divided into applied fertilizer nitrogen equivalent dosages of 120 pounds/acre, 160 pound/acre, 200 pound/acre and 240 pound/acre.

Fertilization Schedule

Twenty-One pounds of nitrogen equivalent fertilizer, as ammonium sulfate, was applied to both the experimental and control sections in October 2014. Soil analyses of all subsections confirmed this to be the starting point for the 2015 corn crop season, with reasonable variation of same.

Sixty pounds of nitrogen equivalent fertilizer, as urea, ammonium and nitrate, was applied to both the experimental and control sections at the end of April 2015 when the seeds were planted. Due to unusually heavy rains experienced in the spring of 2015, it is unclear how much of this applied fertilizer was retained for crop adsorption during the 2015 crop season (See Extraordinary 2015 Rainfall, below).

Forty pounds to one hundred and sixty pounds of nitrogen equivalent fertilizer as ammonium nitrate was applied to both the experimental and control sections as required to achieve four distinct subsections in each section with total applied nitrogen equivalent in pounds per acre of 120, 160, 200 and 240. Final fertilizer application was made in May/June, when the corn vegetation was two feet tall.

Exemplary compositions comprising the specific ion complexing agents were applied to the experimental sections but not to the control section. A total of four specific ion complexing agents were applied to the experimental sections. Two of the complexing agents were specific to ammonium ions and two were specific to nitrate ions.

Various combinations of ammonium and nitrate ASI specific ion complexing agents were applied to each experimental section. The experimental sections differed in terms of which combination of ammonium and nitrate ASI specific ion complexing agents it received. (Table 6). The dosages of ASI complexing agents applied to each subsection was equivalent to the amount of ammonium nitrate fertilizer applied at the corn plant height of two feet.

TABLE 6

| Pilot Plant Section | Nitrate Complexing Agent* | Ammonium Complexing Agent* | Substrate |
|---|---|---|---|
| A | WS N-501 | WS A-101 | Biosolids |
| B | WS N-601 | WS A-101 | Biosolids |
| C | WS N-501 | WS A-201 | Biosolids |
| D | WS N-601 | WS A-201 | Procell |
| E | WS N-501 | WS A-101 | Procell |

TABLE 6-continued

| Pilot Plant Section | Nitrate Complexing Agent* | Ammonium Complexing Agent* | Substrate |
|---|---|---|---|
| F | WS N-601 | WS A-201 | Cellulose |
| Z | None | None | None |

WS A-101: 1,10-diaza-4,7,13,16,21,24-hexaoxabicyclo[8.8.8]hexacosane;
WS A-201: 4,7,13,16,21,24-hexaoxa-1,10 diazabicyclo[8.8.8]hexacosane;
WS N-501: 3,6,9,17,20,23-hexaazatricyclo[23.3.1.111,15]-triaconta-1(29),11,13,15(30), 25,27-hexaene;
WS N-601: 7-[2-Hydroxy-3-(4-phenylpiperazin-1-yl)-propyl]-1,3-dimethyl-8-(2-morpholin-4-ylethylamino)-3,7-dihydropurine-2,6-dione.

Corn Harvesting

The corn from each experimental and control subsection was harvested by hand in September 2015. In harvesting each subsection containing six rows, only the middle four rows were harvested, leaving buffer rows between each subsection of different fertilizer dosages and between each section of different combinations of ASI specific ion complexing agents. The buffer rows minimized interference in test results from different fertilizer dosages and different complexing agents in adjacent subsections.

Stalks with Multiple Healthy Ears of Corn

Almost always, corn stalks produce one healthy ear of corn. Seed suppliers purport that one healthy ear has improved yield as compared to two or three smaller sized ears. Before and during harvesting, it became evident that there was high incidence of stalks containing multiple ears of healthy corn in the experimental rows. Stalks with multiple ears were not harvested as there was concern of skewing the results of the instant research. In excluding harvesting of stalks with multiple healthy ears of corn the equivalent planting area containing same was also excluded. This prevents skewing of yield results on stalks with single healthy ears of corn from stalks with multiple healthy ears of corn.

Corn Shelling and On-Site Analyses

Of the 168 rows of field corn planted, excluding the buffer rows previously referenced, 112 rows were harvested. With an average of 80 ears per row, almost 9,000 ears of corn were handpicked and bagged separately by row. Each of the 112 rows of corn was shelled using an International Harvester one hole manual sheller that had been upgraded with an electric motor attached to a pulley.

The shelled corn, husks and cobs were collected, weighed and samples taken for lab analyses. On-site analyses of the corn included percent moisture, density and temperature using a Dickey John Mini Mac Plus combination meter. According to standard convention, all on-site weights were normalized to 15% moisture content. Normalizing the moisture content of corn allows comparison of corn weights without distortion due to differing moisture contents. Industry standard is to compare corn weight versus a 15% moisture standard, which is the convention of corn grain purchasers.

Extraordinary Rainfall

Challenging the present study was the fact that heavy spring rains occurred at the pilot plant site as shown in Table 7.

TABLE 7

| 2015 Month | Total Rain Inches | Normal Total Inches | Days Rain >1.00" | Normal Days Rain >1.00" | Extremes Inches | Date of Extremes |
|---|---|---|---|---|---|---|
| April | 3.38 | 3.63 | 1 | 0.7 | 1.09 | 4/08 |
| May | 5.02 | 4.33 | 0 | 1.2 | 1.22 | 5/07-5/08 |
| June | 11.60 | 3.53 | 3 | 0.9 | 3.14 | 6/07 |
| July | 5.84 | 3.85 | 3 | 1.12 | 2.15 | 7/10-7/11 |
| August | 2.03 | 3.24 | 1 | 0.8 | 1.28 | 8/17-8/18 |
| September | 3.25 | 3.15 | 1 | 0.8 | 2.23 | 9/18 |

National Climatic Data Center for Peoria IL Airport

While rainfall for April to July was 68% greater than normal, review of the above rainfall shows seven incidents where rainfall exceeded one inch. During this same period, normal incidents of rainfall exceeding one inch was approximately four per year. Rainfall exceeding one inch in a 24 hour period increases nutrient leaching loss from agricultural sites exponentially. May through July is the prime growth and reproductive period for corn. Low nutrient availability is very stressful to corn growth and reproduction.

Analysis and Discussion

Table 8 shows the corn yield improvement obtained with the inventive compositions comprising specific ion complexing agents. As seen from the data in Table 8, use of the compositions according to embodiments of the invention resulted in a remarkable increase in corn yield ranging from 40% to 63.7% higher yield versus the control. The corn yield improvement was remarkable.

TABLE 8

Corn Yield

| Fertilizer Dosage | Bushels/ Acre Control | Ave. Bushels/ Acre Experimental | % Difference Exp. Over Control |
|---|---|---|---|
| 120 lb N equivalent | 155.5 | 254.5 | +63.7 |
| 160 lb N equivalent | 198.0 | 278 | +40.4 |
| 200 lb N equivalent | 195.2 | 281.5 | +44.2 |
| 240 lb N equivalent | 198.0 | 291.1 | +47.0 |

Each subsection was divided according to the total amount of fertilizer applied and recorded as nitrogen equivalent. For example, ammonium (N4) with an equivalent weight of 18 has nitrogen (N) equivalent of 14; thus, 18 pounds of applied ammonium has an equivalent weight of 14 pounds of nitrogen. Conversely, nitrate (NO3) with an equivalent weight of 62 has a nitrogen (N) equivalent weight of 14; thus, 62 pounds of nitrate is recorded, according to standard convention, as 14 pounds of nitrogen (N) equivalent.

It is noted that much of the sixty pound nitrogen equivalent fertilizer addition, applied at planting of the seeds, may have been leached out of the control subsections during the extreme rains in May and June. Two hundred pound nitrogen equivalent fertilizer addition may be optimum to yield three hundred$^+$ bushels of corn/acre if uncomplexed nitrogen can be controlled.

Section C, combination of ion specific nutrient complexing agents, may not be an optimum path forward versus other ASI ion specific complexing agent combinations.

In conclusion, ASI Specific Ion nutrient complexing agents were successful in increasing corn crop yields, despite heavy rain falls. The increased experimental yields over control yield may be skewed by the heavy rainfalls during the 2015 growing season.

Example 2: Nitrogen/Nutrient Runoff Control

Computation of the usage of fertilizer in the ASI pilot plant is comprised of two factors. Factor A calculates the mass of nitrogen-based fertilizer added to the pilot plant. Each of the corn plant components, stalks, ears, roots, grain, husks, and cobs are analyzed for nitrogen assimilation. Comparison of the amount of fertilizer applied versus the amount of fertilizer taken up by the plants yields a Nitrogen Utilization Efficiency.

Factor B calculates the nitrogen inventory in the soil prior to the start of the pilot plant and compares it to the nitrogen inventory in the soil at harvest. The comparison of the beginning and ending nitrogen inventory results yields Soil Supply Efficiency.

Integration of the Nitrogen Utilization Efficiency with the Soil Supply Efficiency yields a Composite System Efficiency.

Increased composite system efficiency results in lower nutrient loss to runoff. There have been proposed a number of nutrient utilization efficiency metrics. In this study, inventor(s) developed and used a simple Composite System Efficiency calculation which includes two factors:

Factor A: determines total N ("nitrogen") supply minus total N in grain and stover (stalk, leaf, cobs, husks and roots) at harvest. A positive difference indicates excess N has been added beyond that required for corn plant growth. The excess is either in soil inventory or is lost to runoff. A negative difference indicates deficient N supply with the assumption that N Utilization Efficiency is >100%. The deficiency is obtained from soil inventory.

Factor B: determines changes in the total N inventory in the soil at the beginning versus the end of a growing season. When the ending N soil inventory is less than the beginning inventory, N has been removed from soil inventory. When the ending N soil inventory is greater than the beginning inventory, N has been added to soil inventory.

Nitrate and ammonium soil inventory is determined by soil sampling at the beginning and the end of a growing season. Both nitrate and ammonium are converted to nitrogen and combined to form total nitrogen inventory.

Methods

A. Mass of grain and stover calculation. The total mass of grain, stalks and leaves, husks, cobs and roots were individually weighed at harvest (stalks, leaves, and roots) or after shelling (grain, husks and cobs).

Since only four of the six rows in each of the control and experimental subsections were harvested, the mass results were multiplied by 1.5 to obtain a final total of mass used by the plants.

Each control and experimental subsection had laboratory analyses performed individually on each plant segment from each harvested row. The individual plant segment from each row was composited for analyses. The test results of each harvested plant segment were multiplied by 1.5 to estimate the total mass for the entire subsection including the unharvested plant segments.

B. Mass of applied nitrogen. In the fall of 2014 twenty-one pounds/acre of N equivalent (as ammonium sulfate) was uniformly applied to the entire 75 acre farm, which included the ASI pilot plant (0.42 acres), by the farmer partner. In the spring of 2015 sixty pounds of N equivalent (from a blend of 34% urea, ammonium and nitrate) was uniformly applied to the entire 75 acre farm, including the pilot plant, by the farmer partner. This application of N was concurrent with corn seed planting.

In late spring of 2015, when corn plants were two feet tall, the final dosages of 40, 80, 120 and 160 pounds of N equivalent (as 20% ammonium nitrate solution) was uniformly applied to each 0.015/acre subsection of the ASI pilot plant by hand. Each experimental and control section was divided into four subsections. All subsections designated as 1, received 0.6 pound dosages. All subsections designated as 2, received 1.2 pound dosages. All subsections designated as 3, received 1.8 pound dosages. All subsections designated as 4 received 2.4 pound dosages.

The ASI specific ion complexing agents were applied to each subsection respectively at the time the final dosage of N was applied.

C. Soil beginning analysis. Before planting of corn seeds and before the addition of the 60 pound/acre N dosage, four samples of soil from each row were collected. Each of the four samples was combined into a row composite. Each row composite was individually analyzed by SGS International. The results of these lab analyses establish the beginning soil inventory.

D. D. Soil ending analysis. After harvesting the corn at Black Layer, shown below, four samples of soil were collected from each row and composited into a single sample for laboratory analysis of each by row by SGS International.

Results and Discussion

Factor A determines Total N ("nitrogen") applied minus total N in grain and stover at harvest. The following FIGS. 7-10 compare Nitrogen Supplied by Fertilizer in pounds versus Nitrogen measured in corn plants in pounds at harvest. An excess or a positive result indicates more fertilizer was applied than used by plants. A negative result indicates more nitrogen was measured in the plants than was supplied to the plants by fertilizer additions. All usage measurements were made at harvest based on laboratory analyses of each plant component which were then totaled.

Figure 7:
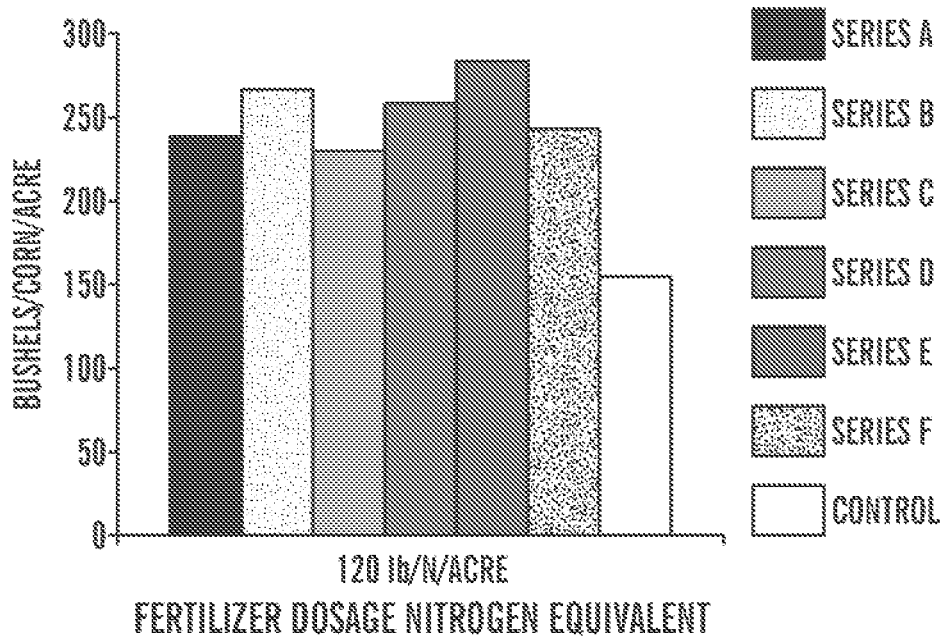
FIGS. 7-10 are bar graphs showing excess or deficiency in N used by the plants verses that applied for the 120 pound N equivalent (FIG. 7), 160 pound N equivalent (FIG. 8), 200 pound N equivalent (FIG. 9) and 240 pound N equivalent (FIG. 10).
Figure 8:
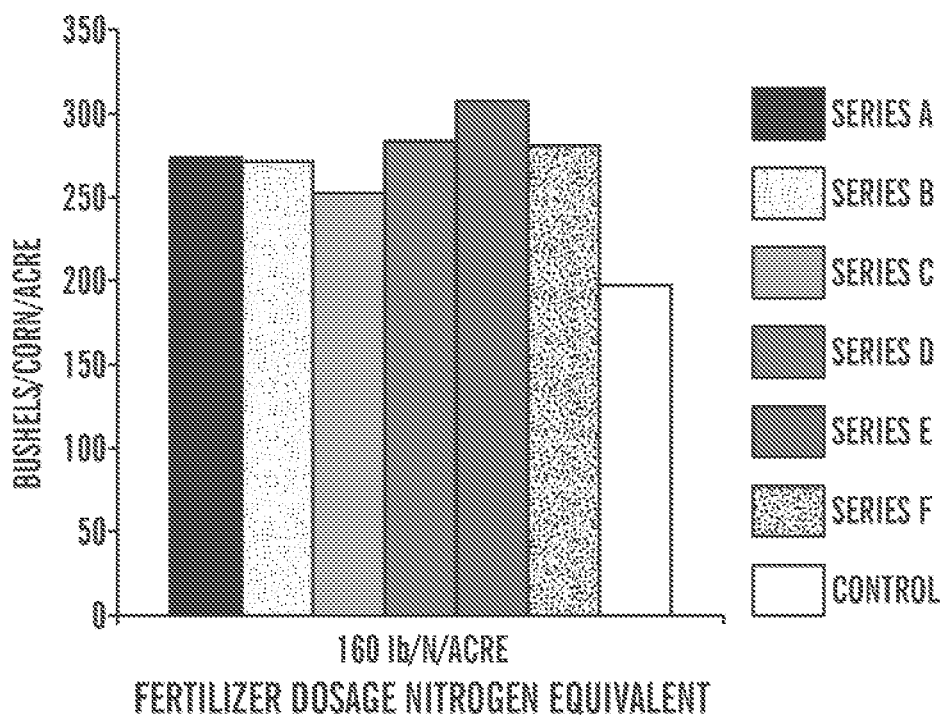
Figure 9:
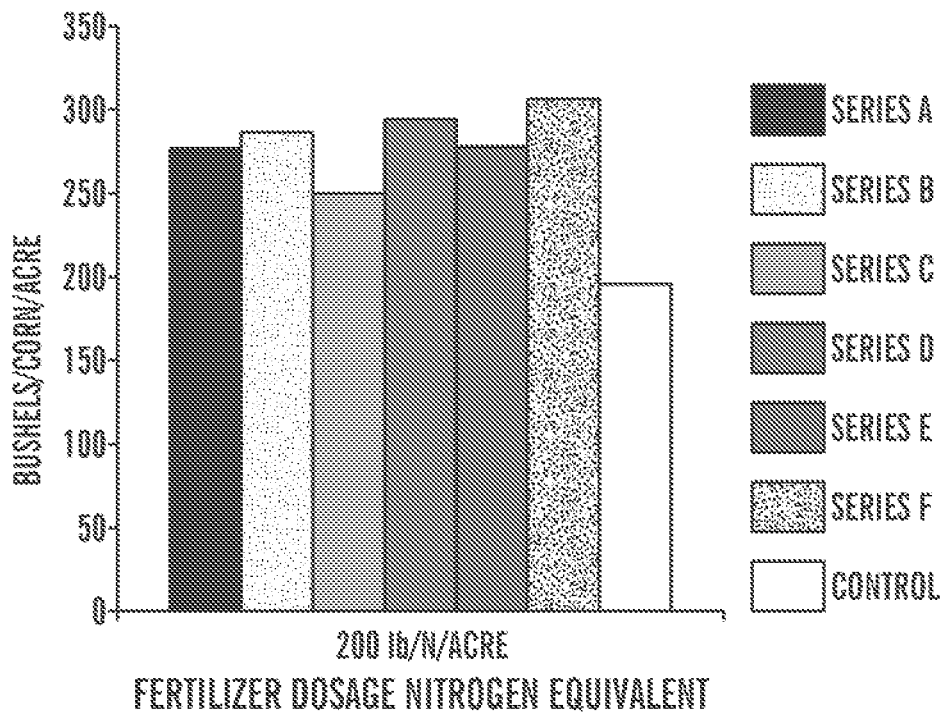
Figure 10:
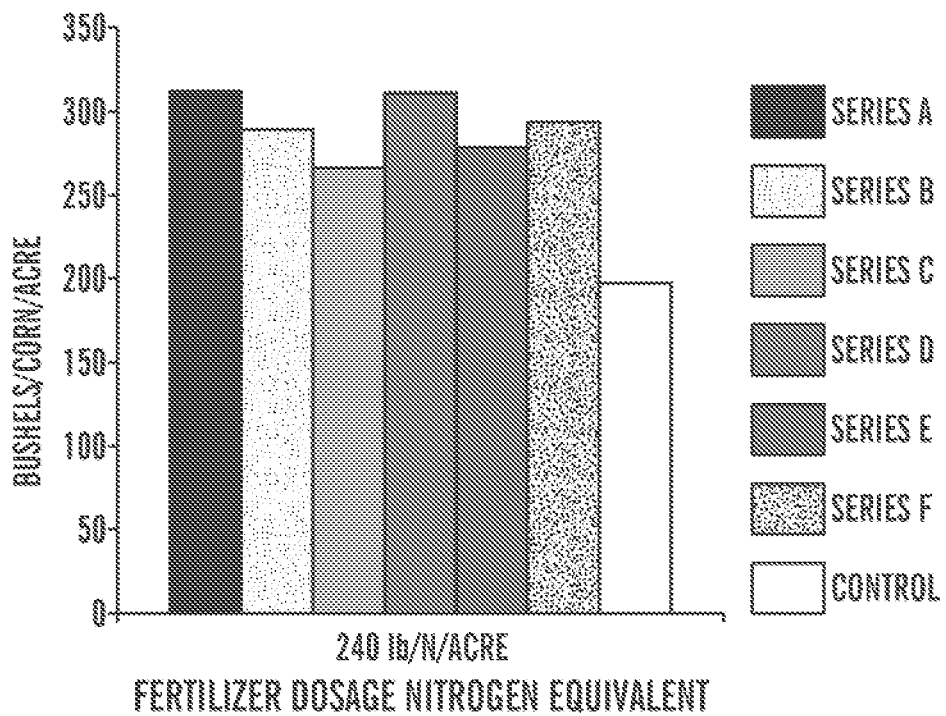

The data in FIGS. 7 and 8 show that for the 120 pound N (FIG. 7) and 160 pound N (FIG. 8) equivalent fertilizer dosage, all of the experimental subsections had a lower amount of N used by the plants versus that applied. In contrast, the control subsection had an excess of N applied versus that used by the plants. As seen from FIG. 9, for the 200 pound N equivalent, two of the experimental subsections (subsections D and F) measured a lower amount of N used by the plants versus that applied. The control subsection and experimental subsections A, B, C and E showed an excess of N applied versus that used by the plants. For the 240 pound N equivalent, all of the experimental and control subsections measured an excess of N used by the plants versus that applied (FIG. 10). However, the subsections varied widely based on the combination and type of nitrate and ammonium specific complexing agent employed.

Figure 5:
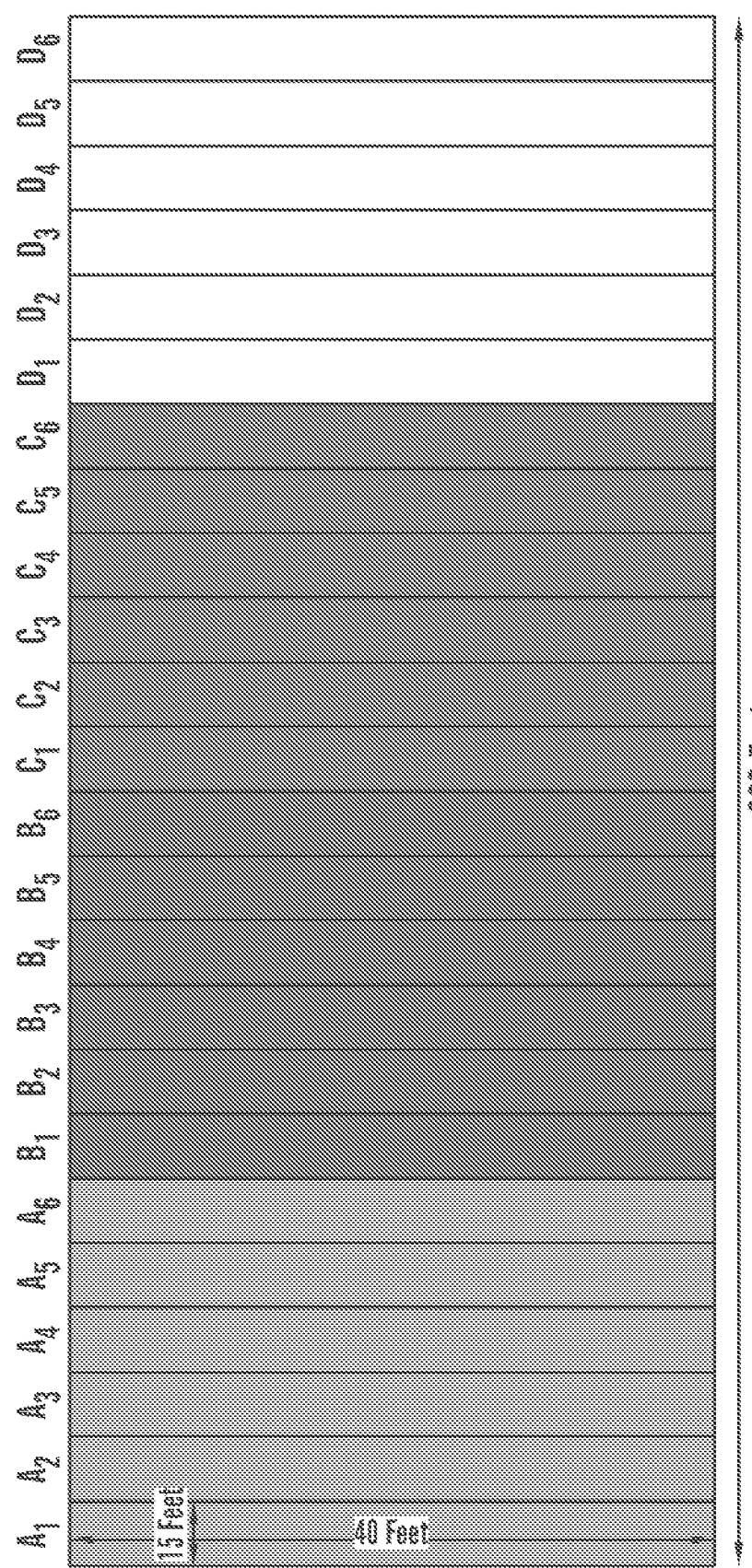
FIG. 5 is a graphic depiction of a pilot plant lay-out according to an exemplary embodiment of the invention.
Figure 6:
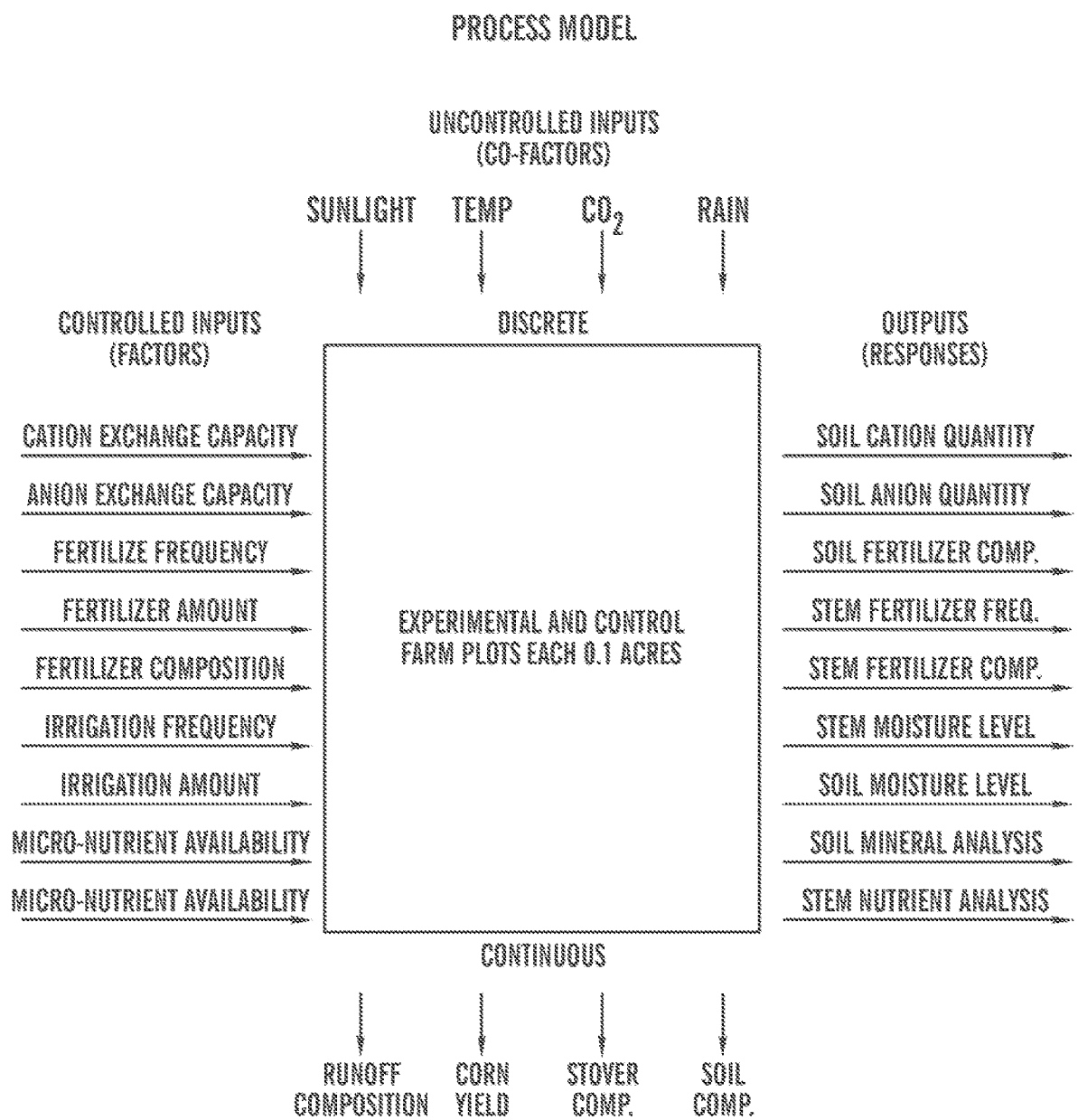
FIG. 6 is a graphical illustration of a process model according to an exemplary embodiment of the invention. The layout contains three experimental segments and one control segment. Each segment contains six sub-segments with six rows each with 30 inch spacing. Seed concentration is 32,000 per acre. Seed spacing is approximately 7 inches.

Factor B: determines changes in the total N inventory in the soil from the beginning versus the end of a growing season. Changes in soil nitrogen inventory before the pilot plant in early spring was compared to the final soil nitrogen inventory at harvest. Added to the inventory was the nitrogen contribution from mineralization of last year's stover. The changes in soil nitrogen inventory was then added or subtracted to the Nitrogen Nutrient Utilization Efficiency calculation. The results of combining the changes in the soil inventory with the N/NUE were outlined for each subsection. The final result is a Composite System Efficiency for utilization of nitrogen in the ASI pilot plant. The results are shown in FIGS. 5-7.

Figure 11:
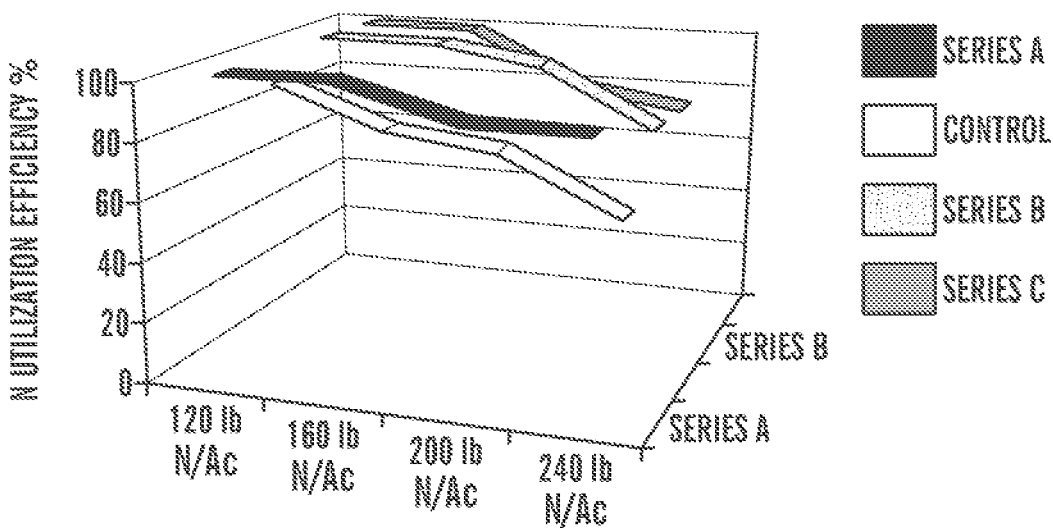
FIGS. 11 and 12 are graphs showing nitrogen/nutrient utilization efficiency by varying applied nitrogen dosages.
Figure 12:
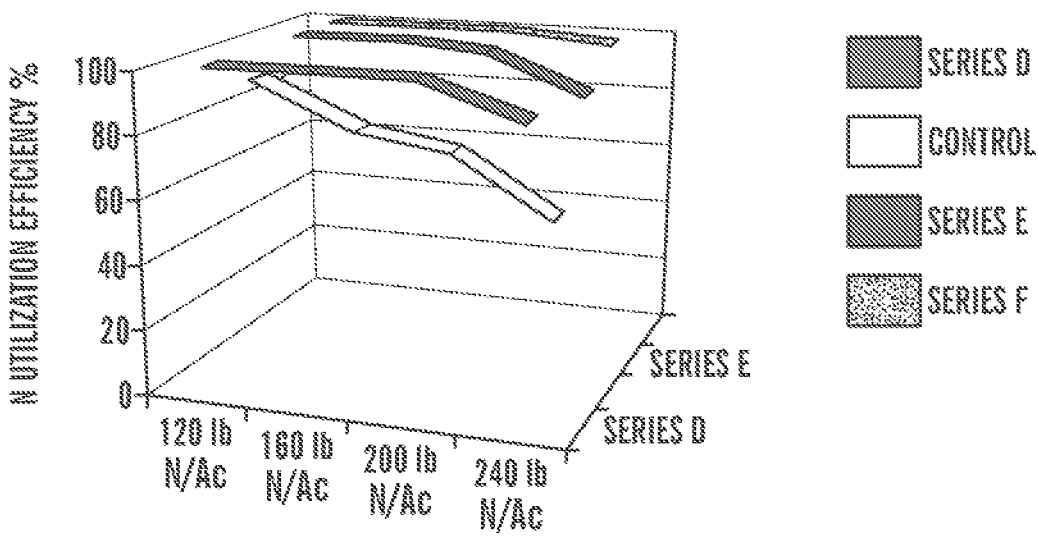
Figure 13:
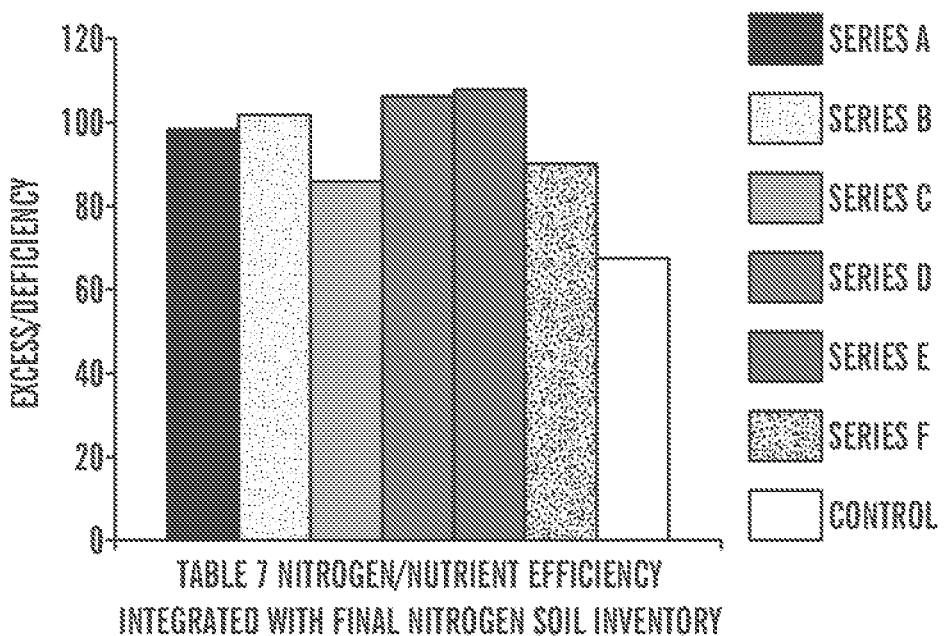
FIG. 13 is a bar graph showing nitrogen/nutrient efficiency integrated with final nitrogen soil inventory.

As seen from FIGS. 11-13, experimental subsections Series A, B and C measured N Utilization Efficiencies of 95%, 92% and 89% respectively (FIG. 11) and experimental subsections Series D, E and F measured N Utilization Efficiencies of 97%, 96% and 99% respectively (FIG. 12) versus the Control Series N Utilization efficiency of 73%.

A comparison of the Control versus the Experimental nitrogen efficiency utilization is shown in FIG. 13. As seen from FIG. 13, the Control Section had a Composite System Efficiency of 67.2% while the Experimental Sections had Composite System Efficiencies of as follows: 98.1% (subsection A); 101.3% (subsection B); 85.3% (subsection C); 106.1% (subsection D); 107.6% (subsection E) and 90.0% (subsection F). It is noted that composite system efficiency in excess of 100% is possible if the soil is capable of fixing nitrogen (nitrogen fixation) from the air and converting it to usable nitrate or ammonia. Alternatively, the calculated amount of usable nitrogen is greater than it actually is. This demonstrates that the SICA disclosed herein are capable of fixing nitrogen.

Example 9: Manufacturing Process A

Exemplary nutrient complexing compositions comprising WS A-101 (1,10-diaza-4,7,13,16,21,24-hexaoxabicyclo[8.8.8]hexacosane; $N[CH_2CH_2OCH_2CH_2OCH_2CH_2]_3N$) as the complexing agent and biosolids as the substrate can be prepared at pilot scale as follows:

A. Materials Required
   Coupling Buffer: 0.1M sodium phosphate, 0.15M NaCl, pH 7.2
   1 kg Biosolids, reduced and dissolved in Coupling Buffer
   BMPH crosslinker, equilibrated to room temperature before opening
   Crosslinker Solvent: dimethylformamide or dimethylsulfoxide.
   Oxidation Buffer: 0.1M sodium acetate, pH 5.5
   WS A-101 dissolved in Oxidation Buffer
   Sodium meta-periodate B. Biosolids Reaction with Crosslinker
   1. Prepare 10-50 mM Crosslinker in Solvent. For BMPH, 3.0 g/L equals 10 mM solution.
   2. Add a volume of Crosslinker solution to the Biosolids to achieve a 5- to 10-fold molar excess of reagent over Biosolids. To minimize Biosolids damage or precipitation, do not exceed 10% Crosslinker Solvent in the final mixture.
   3. Incubate reaction mixture for 2 hours at room temperature or
   4. 4 hours at 4° C.

C. WS A-101 Oxidation
   1. Prepare 20 mM periodate solution by dissolving 4.3 g of sodium meta-periodate per liter of Oxidation Buffer. Prepare a volume equal to the volume of WS A-101 solution. Keep solution on ice and protect it from light.
   2. Add 1 L of cold sodium meta-periodate solution to 1 L of the WS A-101 solution and mix well. Allow the oxidation reaction to proceed for 30 minutes in the dark on ice or at 4° C.

D. WS A-101 Conjugation
   1. In proportions appropriate for the intended conjugation and number of available functional groups, combine solutions of crosslinker-modified Biosolids from Section B and the oxidized WS A-101 from Section C.
   2. Incubate reaction mixture for 2 hours at room temperature Exemplary nutrient complexing compositions comprising WS A-201 (4,7,13,16,21,24-hexaoxa-1,10 diazabicyclo[8.8.8]hexacosane) as the complexing agent and biosolids as the substrate can be prepared at pilot scale as follows:

A. Materials Required
   Biosolids 2 kg
   Conjugation Buffer: 0.1M MES (2-[N-morpholino]ethane sulfonic acid), pH 4.5-5
   EDC: 10 kg
   WS A-201: 1-2 kg B. Procedure
   1. Equilibrate EDC to room temperature.
   2. Add 2 kg of lyophilized Biosolids to 200 L Conjugation Buffer.
   3. Dissolve 2 kg of the WS A-201 in 500 L of Conjugation Buffer and add it to the 200 L carrier Biosolids solution.
   4. Dissolve 10 kg of EDC in 100 L of ultrapure water and immediately add 50 L of this solution to the carrier-Biosolids solution.
   5. React for 2 hours at room temperature.
   6. If storing the conjugate for more than a few days, store in a sterile container at 4° C. or −20° C.

Exemplary nutrient complexing compositions comprising WS N-501 (3,6,9,17,20,23-hexaazatricyclo[23.3.1.111,15]-triaconta-1(29),11,13,15(30),25,27-hexaene) as the complexing agent and biosolids as the substrate can be prepared at pilot scale as follows:

A. Materials Required
   Biosolids
   WS N-501
   Oxidizing Agent: Sodium meta-Periodate
   BupH Phosphate Coupling Buffer
   Aniline B. Prepare Biosolids Sample for Coupling)
   1. Dilute or dissolve 2 kg of Biosolids in Coupling Buffer. Dilute samples at least three-fold in Coupling Buffer to a final volume of 2 L and pH<6.
   2. Weigh 4.2 g of sodium meta-periodate into a light excluded tank and add 2 L of Biosolids solution, gently mixing until the powder dissolves (results in 10 mM periodate). Protect from light and incubate the mixture at room temperature for 30 minutes; to prevent over-oxidation, do not exceed the 30 minute incubation.
   3. Slowly apply the oxidized Biosolids solution to the centrifuge.
   4. Centrifuge and collect sample in a 15 L tube. The collected solution contains the oxidized Biosolids.

C. Couple Oxidized Biosolids to WS N-501
   1. Suspend the WS N-501 by gentle mixing. Add 4 L of WS N-501 to a 5 L spin column and centrifuge at 1000×g to remove the storage buffer.
   2. Add 3 L of Coupling Buffer and centrifuge. Repeat with an additional 3 L of Coupling Buffer and cap the bottom of the tube.
   3. In a fume hood, add 18 mL of aniline to 2 L of Biosolids sample. Mix gently until aniline is completely dissolved. Save 0.1 L of the prepared sample for subsequent determination of coupling efficiency.
   4. Add 2 L of the oxidized Biosolids to the WS N-501.
   5. Mix solution by gentle mixing at room temperature for 2-4 hours.
   6. Centrifuge to collect non-bound Biosolids.
   7. Determine coupling efficiency by comparing the Biosolids concentrations of the non-bound fraction to the starting sample (Step 5).
   8. Wash the WS N-501 with 3 L of Coupling Buffer and centrifuge. Repeat this step two times.
   9. Wash the WS N-501 with 3 L of Wash Buffer and centrifuge. Repeat this step two times.
   10. Equilibrate the column for storage by adding 3 L of degassed buffer at pH 7-8 (e.g., phosphate-buffered saline, PBS with optional 0.05% sodium azide) and centrifuge. Repeat this step two times.

11. Add 2 L of degassed buffer at pH 7-8. Store the mixture at 4° C. for up to 3 weeks.

Exemplary nutrient complexing compositions comprising WS N-601 (7-[2-Hydroxy-3-(4-phenylpiperazin-1-yl)-propyl]-1,3-dimethyl-8-(2-morpholin-4-ylethylamino)-3,7-dihydropurine-2,6-dione) as the complexing agent and biosolids as the substrate can be prepared at pilot scale as follows:

A. Materials Required
  Vertical tank containing the desired slurry volume of WS N-601.
  Note: The following coupling procedure is for 2 L of WS N-601
  Coupling solution in a 5 L column.
  Coupling Buffer: 0.1M sodium phosphate, 0.15M NaCl, pH 7.2
  Cyanoborohydride Solution: 5M NaCNBH3 in 1M NaOH
  Quenching Buffer: 1M Tris·HCl, pH 7.4
  Wash Solution: 1M sodium chloride (NaCl)

B. Sample Preparation (Biosolids Solution)
  Dissolve 4 kg Biosolids to be coupled in 4 L of Coupling Buffer. For Biosolids already in solution, dilute sample 4-fold in Coupling Buffer.

C. Coupling procedure
  Biosolids Coupling
    1. Equilibrate vertical tank containing desired volume of WS N-601 to room temperature and allow the WS N-601 to settle. Open tank and drain storage solution into a collection tank. Throughout entire procedure, do not allow the WS N-601 to become dry.
    2. Equilibrate tank by adding 6 L of Coupling Buffer and allowing the contents to drain.
    3. Add 4 L of the Biosolids solution (dissolved in Coupling Buffer) to the tank. Save 0.1 L of the prepared sample for subsequent determination of coupling efficiency.
    4. In a fume hood, add 40 mL of Cyanoborohydride Solution to the reaction slurry (results in ~50 mM NaCNBH3).
    5. Place the top on the tank and mix the reaction by gentle mixing for 6 hours at room temperature or overnight at 4° C.
    6. With ventilation, carefully open the tank top. Some gas pressure may have formed during the reaction.
    7. Open the bottom valve and drain the contents of the tank into a new collection tank.
    8. Determine coupling efficiency by comparing the Biosolids concentrations of the non-coupled fraction to the starting sample (step 3).
    9. Wash WS N-601 with 4 mL of Coupling Buffer.

Block Remaining Active Sites
    1. Wash WS N-601 with 4 L of Quenching Buffer, and then replace the tank top.
    2. With ventilation, add 2 L of Quenching Buffer and 40 mL of Cyanoborohydride Solution to the column (results in ~50 mM NaCNBH3 when mixed with WS N-601). Replace the tank top and mix gently for 30 minutes.
    3. With proper ventilation, carefully remove the tank top. Some gas pressure may have formed during the reaction.
    4. Open bottom valve, place the tank contents in a new collection tank and allow it to drain.

Wash Vertical Tank
    1. Wash tank with at least 10 L (5 bed volumes) of Wash Solution.

Example 10: Manufacturing Process B

Exemplary nutrient complexing compositions comprising WS A-101 as the complexing agent and Procell as the substrate can be prepared at pilot scale as follows:

A. Materials Required
  1 kg Procell, reduced and dissolved in Coupling Buffer
  BMPH crosslinker, equilibrated to room temperature before opening
  Oxidation Buffer: 0.1M sodium acetate, pH 5.5
  WS A-101 dissolved in Oxidation Buffer
  Sodium meta-periodate B. Biosolids Reaction with Cross-linker
  1. Add a volume of Cross-linker solution to the Procell to achieve a 5- to 10-fold molar excess of reagent over Procell. To minimize Procell damage or precipitation, do not exceed 10% Crosslinker Solvent in the final mixture.
  2. Incubate reaction mixture for 2 hours at room temperature or 4 hours at 4° C.

C. WS A-101 Oxidation
  1. Prepare 20 mM periodate solution by dissolving 4.3 g of sodium meta-periodate per liter of Oxidation Buffer. Prepare a volume equal to the volume of WS A-101 solution. Keep solution on ice and protect it from light.
  2. Add 1 L of cold sodium meta-periodate solution to 1 L of the WS A-101 solution and mix well. Allow the oxidation reaction to proceed for 30 minutes in the dark on ice or at 4° C.

D. WS A-101 Coupling
  1. In proportions appropriate for the intended coupling and number of available functional groups, combine solutions of crosslinker-modified Procell from Section B and the oxidized WS A-101 from Section C.
  2. Incubate reaction mixture for 2 hours at room temperature.

Exemplary nutrient complexing compositions comprising WS A-201 as the complexing agent and Procell as the substrate can be prepared at pilot scale as follows:

A. Materials Required
  Procell 2 kg
  EDC: 10 kg
  WS A-201: 1-2 kg

B. Procedure
  1. Equilibrate EDC to room temperature.
  2. Dissolve 2 kg of the WS A-201 in 500 L of water and add it to the 200 L Procell solution.
  3. Dissolve 10 kg of EDC in 100 L of ultrapure water and immediately add 50 L of this solution to the -Procell solution.
  4. React for 2 hours at room temperature. If storing the conjugate for more than a few days, store in a sterile container at 4° C. or −20° C.

Exemplary nutrient complexing compositions comprising WS N-501 as the complexing agent and Procell as the substrate can be prepared at pilot scale as follows:

A. Materials Required
- Procell
- WS N-501
- Oxidizing Agent: Sodium meta-Periodate B. Prepare Procell Sample for Coupling
1. Dilute or dissolve 2 kg of Procell in water. Dilute samples at least three-fold in water to a final volume of 2 L and pH<6.
2. Weigh 4.2 g of sodium meta-periodate into a light excluded tank and add 2 L of Procell solution, gently mixing until the powder dissolves (results in 10 mM periodate). Protect from light and incubate mixture at room temperature for 30 minutes; to prevent over-oxidation, do not exceed the 30 minute incubation.
3. Slowly apply the oxidized Procell solution to the centrifuge.
4. Centrifuge and collect sample in a 15 L tube. The collected solution contains the oxidized Procell.

C. Couple Oxidized Biosolids to WS N-501
1. Suspend the WS N-501 by gentle mixing. Add 4 L of WS N-501 to a
2. 5 L spin column and centrifuge at 1000×g to remove the storage buffer.
3. Add 3 L of water and centrifuge. Repeat with an additional 3 L of water and close the valve on the bottom of the tank.
4. Add 2 L of the oxidized Procell to the WS N-501.
5. Mix solution by gentle mixing at room temperature for 2-4 hours.
6. Centrifuge to collect non-bound Procell.
7. Determine coupling efficiency by comparing the Procell concentrations of the non-bound fraction to the starting sample (Step 5).
8. Wash the WS N-501 with 3 L of water and centrifuge. Repeat this step two times.
9. Wash the WS N-501 with 3 L of water and centrifuge. Repeat this step two times.
10. Equilibrate the column for storage by adding 3 L of water at pH 7-8 and centrifuge. Repeat this step two times.
11. Add 2 L of water at pH 7-8. Store the mixture at 4° C. for up to 3 weeks.

Exemplary nutrient complexing compositions comprising WS N-601 as the complexing agent and Procell as the substrate can be prepared at pilot scale as follows:

A. Materials Required

Vertical tank containing the desired slurry volume of WS N-601.

Note: The following coupling procedure is for 2 L of WS N-601

Coupling solution in a 5 L column.

B. Sample Preparation (Procell Solution)

Dissolve 4 kg Procell to be coupled in 4 L of water. For Procell already in solution, dilute sample 4-fold in water.

C. Coupling Procedure

Procell Coupling

1. Equilibrate vertical tank containing desired volume of WS N-601 to room temperature and allow the WS N-601 to settle. Open tank and drain storage solution into a collection tank. Throughout entire procedure, do not allow the WS N-601 to become dry.
2. Equilibrate tank by adding 6 L of water and allowing the contents to drain.
3. Add 4 L of the Procell solution to the tank. Save 0.1 L of the prepared sample for subsequent determination of coupling efficiency.
4. Place the top on the tank and mix the reaction by gentle mixing for 6 hours at room temperature or overnight at 4° C.
5. Open the bottom valve and drain the contents of the tank into a new collection tank.
6. Determine coupling efficiency by comparing the Procell concentrations of the non-coupled fraction to the starting sample (step 3).
7. Wash WS N-601 with 4 L of water.

Block Remaining Active Sites

1. Wash WS N-601 with 4 L of water, and then replace the tank top.
2. With ventilation, add 2 L of water Replace the tank top and mix gently for 30 minutes.
3. With proper ventilation, carefully remove the tank top. Some gas pressure may have formed during the reaction.
4. Open bottom valve, place the tank contents in a new collection tank and allow it to drain.

Wash Vertical Tank

1. Wash tank with at least 10 L (5 bed volumes) of Wash Solution

Example 11: Manufacturing Process C

Exemplary nutrient complexing compositions comprising WS A-201 as the complexing agent and cellulose as the substrate can be prepared at pilot scale as follows:

A. Materials Required

Cellulose
WS A-201
Vinyl acetate monomer 99%
Cerium nitrate
Cocoamidopropyl betaine (35% solids)
Potassium persulfate
Nitrogen gas B. Vinyl Acetate Pulping with Cellulose 10 kilograms of cellulose were charged into a 1000 l glass mixing tank equipped with an agitator drive. 500 l of DI water was added and the cellulose was pulped by mixing at agitation speed of 300 rpm for 30 minutes.

After pulping was completed, 5.3 kilograms of vinyl acetate monomer (“VAM”)(99%) was added to the pulped cellulose/water mixture. The VAM was mixed with the mixture for 10 minutes at 300 rpm.

After the VAM was thoroughly mixed into the pulped cellulose, 0.2 meq of cerium nitrate was added to the VAM/pulped cellulose mixture.

The cerium nitrate/VAM/Cellulose mixture was heated with mixing for 50 minutes at 50° C.

When the VAM was grafted (86% efficiency) onto the cellulose, the mixture was allowed to cool to 25° C.

C. WS A-201/cellulose Coupling Oxidation

After cooling, 10 kilograms of a WS A-201, 2.9 kilograms of a 35% solids aqueous solution of cocoamidopropyl betaine and 318 g of potassium persulfate were added to the VAM/cellulose mixture with agitation of 300 rpm for 15 minutes.

The tank was then purged with nitrogen for 1 hours and the reaction mass heated to 70° C., and held for 6 hours until the residual monomer concentration was less than 3%. Then 338 g. of dry sodium phosphate was added and mixed for 30 minutes to a pH of 6.5-7.5. The liquid/solids mixture was centrifuged. The centrifuge cake was then transferred to a fluidized bed drier and dried at 120° F. for 2 hours to a moisture level of less than 7%. The product was screened through a 30 mesh screen, overs ground and rescreened.

On analysis, the treated cellulose had percent nitrogen of 2.1 to 2.5, and a percent monomer conversion of 84 to 88%.

Cation Exchange Capacity of the treated biosolids was found to exceed 2.0 EQ/Kg of reacted cellulose.

Exemplary nutrient complexing compositions comprising WS N-601 as the complexing agent and cellulose as the substrate can be prepared at pilot scale as follows:

A. Materials Required
   Cellulose
   WS N-601
   Vinyl acetate monomer 99%
   Cerium nitrate
   Cocoamidopropyl betaine (35% solids)
   Potassium persulfate
   Nitrogen gas B. Vinyl Acetate Pulping with Cellulose
   10 kilograms of cellulose were charged into a 1000 l glass mixing tank equipped with an agitator drive. 500 l of DI water was added and the cellulose was pulped by mixing at agitation speed of 300 rpm for 30 minutes.
   After pulping was completed, 5.3 kilograms of vinyl acetate monomer ("VAM")(99%) was added to the pulped cellulose/water mixture. The VAM was mixed with the mixture for 10 minutes at 300 rpm.
   After the VAM was thoroughly mixed into the pulped cellulose, 0.2 eq of cerium nitrate was added to the VAM/pulped cellulose mixture.
   The cerium nitrate/VAM/Cellulose mixture was heated with mixing for 50 minutes at 50° C.
   When the VAM was grafted (86% efficiency) onto the cellulose, the mixture was allowed to cool to 25° C.

C. WS A-601/cellulose Coupling Oxidation
   After cooling, 10 kilograms of WS N-601, 2.9 grams of a 35% solids aqueous solution of cocoamidopropyl betaine and 318 g of potassium persulfate were added to the VAM/cellulose mixture with agitation of 300 rpm for 15 minutes.
   The tank was then purged with nitrogen for 1 hours and the reaction mass heated to 70° C., and held for 6 hours until the residual monomer concentration was less than 3%. Then 338 g. of dry sodium phosphate was added and mixed for 30 minutes to a pH of 6.5-7.5. The liquid/solids mixture was centrifuged. The centrifuge cake was then transferred to a fluidized bed drier and dried at 120° F. for 2 hours to a moisture level of less than 7%. The product was screened through a 30 mesh screen, overs ground and rescreened.
   On analysis, the treated cellulose had percent nitrogen of 5.1 to 5.5, and a percent monomer conversion of 85 to 89%.
   Anion Exchange Capacity of the treated cellulose was found to exceed 5.0 EQ/Kg of reacted cellulose.

Example 12: Evaluation of Exchange Capacity

An exemplary method for evaluating the exchange capacity of a SICA is the "total loading-total elution" technique. A general outline of this technique is as follows:
1. The SICA is fully loaded to the desired ionic form.
2. The SICA is rinsed free of the loading ions and the feed solution is passed through the SICA until the effluent composition is the same as the feed composition. At this point, the SICA has taken up as much of the ion being complexed as is possible.
3. A suitable eluent is passed through the column until the ion under consideration is completely removed from the SICA.

Let us consider a specific example in which it was desired to determine the exchange capacity of an ammonium SICA. Initially it is desired to completely load the SICA to the hydrogen form. In this scenario, the sulfuric acid reagent ($H_2SO_4$-0.0302M) is passed through the SICA at a flow rate equivalent to 1 gpm/square feet of cross-sectional bed area until none of the original ion present on the SICA is detectable in the effluent. Using a 100 ml burette with a 9 mm diameter ID column, relates to a reagent flow of 1.5 ml/min.

Figure 14:
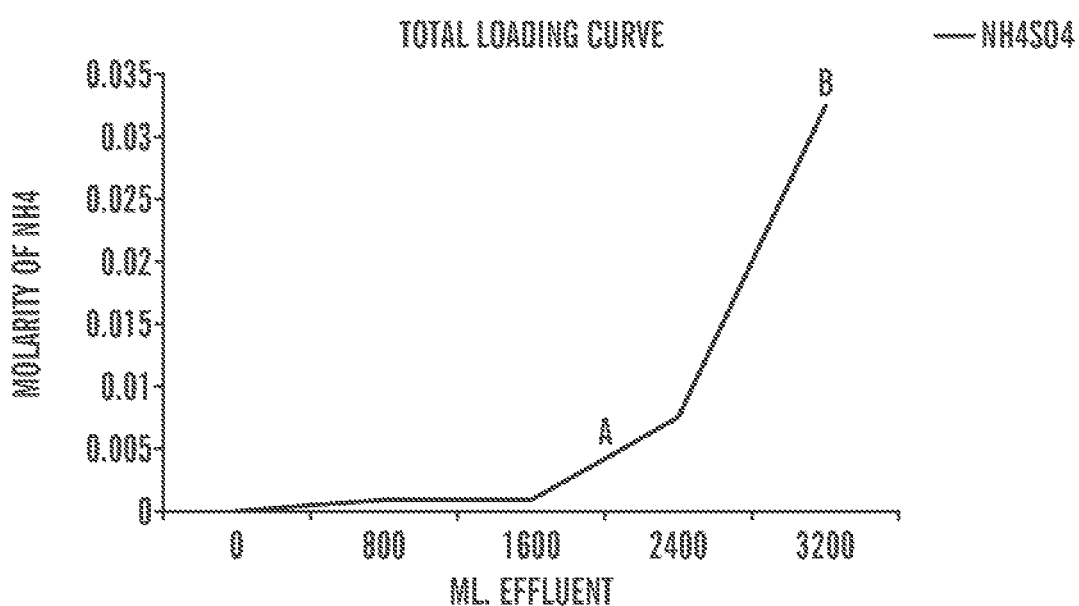
FIG. 14 shows total loading curve for determining exchange capacity of an exemplary SICA embodiment of the invention.

A column using a 100 ml burette contains approximately 89 ml of SICA. The feed solution is passed through the column at a flow rate of 1 gpm/sq. ft. at ambient temperature. The effluent is analyzed every 5 minutes until concentration in the effluent from the column is equal to that in the feed solution ($NH_4SO_4$-0302M). The total loading curve for a typical run is shown in FIG. 14. When the ammonium begins to break through, its concentration in the effluent increases rapidly following a typical "S" curve. At Point B, the zinc concentration in the effluent is equal to its concentration in the feed solution and thus the SICA is as fully loaded with ammonium as is possible under the conditions of operation.

Operating capacity may be expressed in grams of ammonium or other cations complexed per liter of SICA. The capacity determined from the total loading curve is a maximum since the SICA was fully loaded before operation. In this particular case, we can readily determine the maximum number of pounds of ammonium which can be removed per cubic foot of SICA per cycle. The calculation of maximum operating capacity using Point (A) as the end point is as follows:

$$\text{Molecular weight } NH_4SO_4 = 132$$

Weight of $NH_4SO_4$ removed (grams) =

$$2 \text{ liters } X 0.0302\, MX 132 = 8.0 \text{ g } NH_4SO_4$$

$$\frac{8.0 \text{ g}}{89 \text{ ml}} = \frac{X}{1,000 \text{ (ml/liter)}}$$

$X = 3080$ g $NH_4SO_4$ per cubic foot =

$$90 \text{ g } NH_4SO_4 \text{ per liter (or 60 meq/liter)}$$

Example 12: Evaluation of Exchange Capacity

A method for conducting a laboratory evaluation of the selectivity of a SICA is to the Exchange Capacity outlined above. A general outline of the technique is as follows:
1. The SICA is fully loaded to the desired ionic form.
2. The SICA is rinsed free of the loading ions and the feed solution is passed through the SICA until the effluent composition is the same as the feed composition. At this point, the SICA has taken up as much of the ion being complexed as is possible.
3. A suitable eluent is passed through the column until the ion under consideration is completely removed from the SICA.

Let us consider a specific example in which it was desired to determine the selectivity of a cation exchange SICA. Initially it is desired to completely load the SICA to the hydrogen form. In this scenario, the sulfuric acid reagent ($H_2SO_4$-0.0302M) is passed through the SICA at a flow rate equivalent to 1 gpm/square feet of cross-sectional bed area until none of the original ion present on the SICA is detectable in the effluent. Using a 100 ml. burette with a 9 mm diameter ID column, relates to a reagent flow of 1.5 ml/min A column using a 100 ml. burette contains approximately 89 ml of SICA. A feed solution consisting of 0.0302M solutions of K₂SO₄, Na₂SO₄, (NH₄)₂SO₄, CaSO₄, MgSO₄ is passed through the column at a flow rate of 1 gpm/sq. ft. at ambient temperature. The effluent is analyzed every 5 minutes until concentration in the effluent from the column is equal to that in the feed solution (i.e. K₂SO₄, Na₂SO₄, (NH₄)₂SO₄, CaSO₄, MgSO₄-0.302M each). The total loading curve for a typical run can be prepared as shown in FIG. 14. When the cations begin to break through, its concentration in the effluent increases rapidly following a typical "S" curve. At a specific point, the cations concentration in the effluent is equal to its concentration in the feed solution and thus the SICA is as fully loaded with cations as is possible under the conditions of operation.

Operating capacity may be expressed in grams of ammonium or other cations complexed per liter of SICA. The capacity determined from the total loading curve is a maximum since the SICA was fully loaded before operation. In this particular case, we can readily determine the maximum number of pounds of ammonium which can be removed per cubic foot of SICA per cycle. The calculation of maximum operating capacity using Point (A) as the end point is as follows:

Molecular weight NH₄SO₄ = 132

Weight of NH₄SO₄ removed (grams) =

$$2 \text{ liters} \times 0.0302 \, M \times 132 = 8.0 \text{ g NH}_4\text{SO}_4$$

$$\frac{8.0 \text{ g}}{89 \text{ ml}} = \frac{X}{1{,}000 \text{ (ml/liter)}}$$

X = 3080 g NH₄SO₄ per cubic foot =

90 g NH₄SO₄ per liter (or 60 meq/liter)

Figure 15:
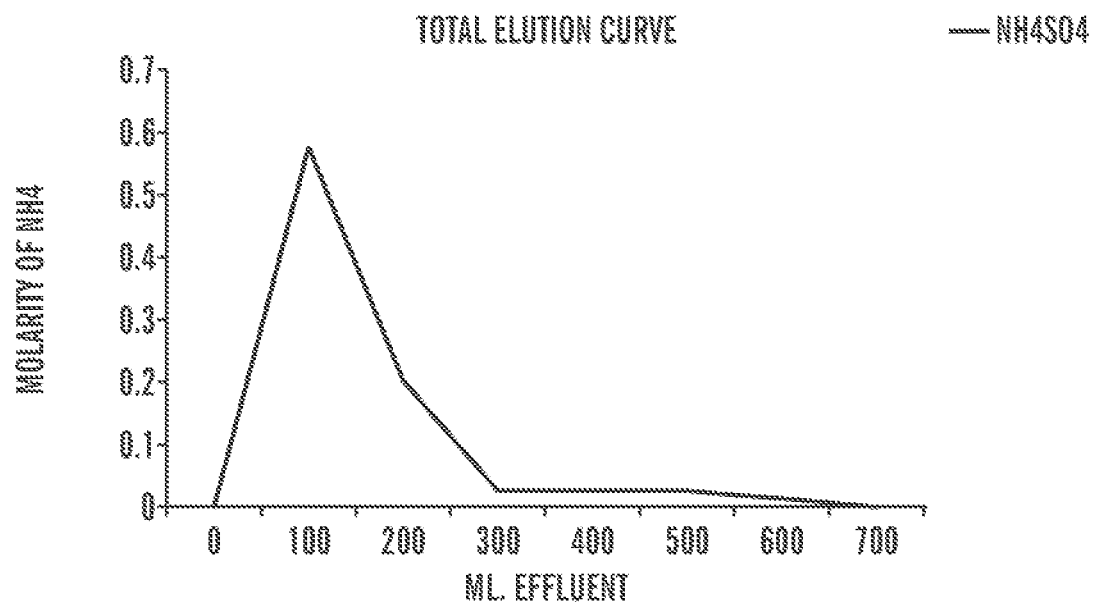
FIG. 15 shows the total elution curve for determining selectivity of an exemplary SICA of the invention.
Figure 16:
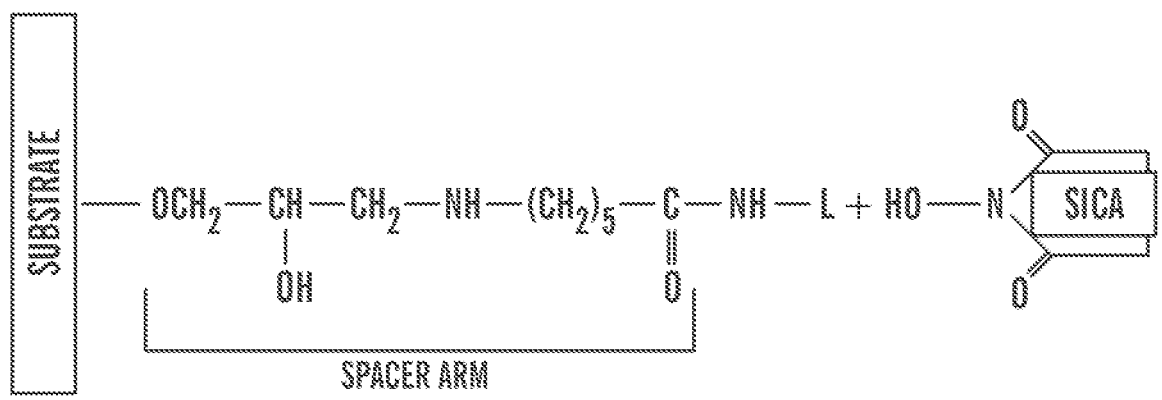
FIG. 16 shows linking of a SICA to a substrate via a linker/spacer. L is a linker.
Figure 17:
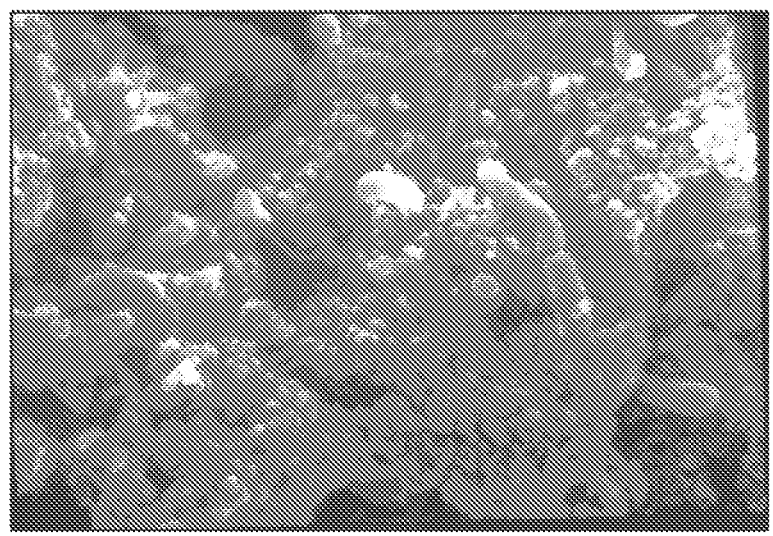
FIG. 17 is a photograph showing nutrient-SICA complex according to an embodiment of the invention.
Figure 18:
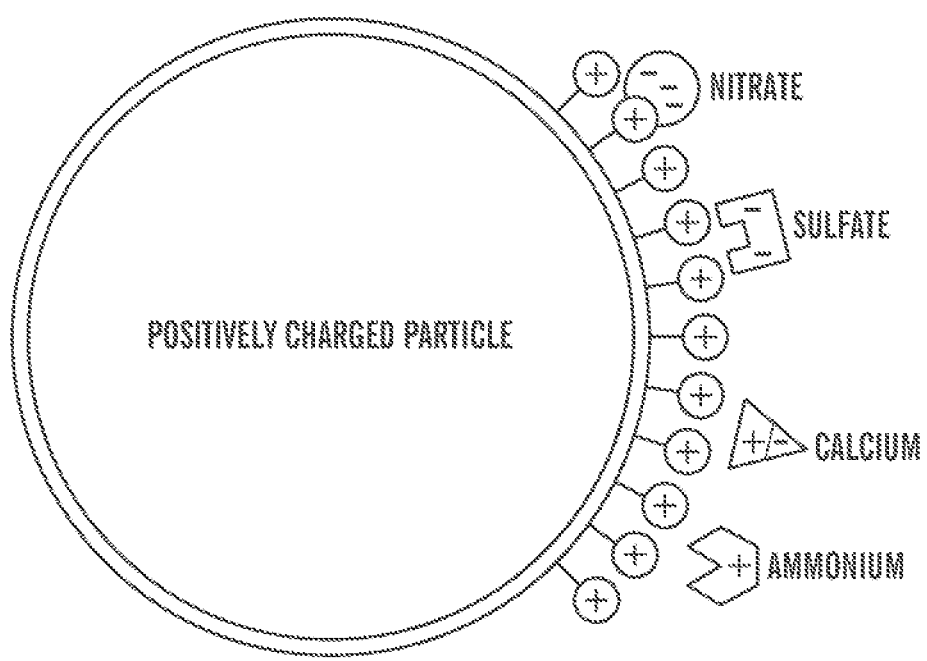
FIG. 18 is schematic representation of specific ion complexing affinity of a nitrate SICA.

The regenerant chosen for the total elution step is 2.33 molar H2SO4. The acid was passed through the resin at one gpm/square foot at 25° C. until no ammonium or other cation was detectable in the effluent. The total elution curve is shown in FIG. 15.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A composition for use at a crop planting site, the composition comprising:
   a specific ion complexing agent (SICA) coupled to a substrate via a linker molecule,
   wherein said SICA forms a coordination complex with, and reversibly retains, a desired compound,
   wherein the SICA is selected from the group consisting of 1,5-diazabicyclo[4.3.0]non-5-ene, 3,6,9,17,20,23-hexaazatricyclo[23.3.1.111,15]-triaconta-1 (29), 11,13, 15 (30),25,27-hexaene, and 7-[2-Hydroxy-3-(4-phenylpiperazin-1-yl)-propyl]-1, 3-dimethyl-8-(2-morpholin-4-ylethylamino)-3, 7-dihydropurine-2,6-dione, and
   wherein said desired compound is selected from the group consisting of a nitrate, nitrite, ammonium, phosphate, sulfate, and combinations thereof.

2. The composition of claim 1, wherein said nitrate, nitrite, ammonium, phosphate, sulfate, or combination thereof is a nutrient, mineral, pesticide, herbicide, growth stimulator, and combinations thereof.

3. The composition of claim 1, wherein the substrate is selected from the group consisting of clay, silica, aluminum silicates, metal oxides, carbohydrates, cellulose, starches, bio-solids, proteins, a single cell protein, amino acids, fats, oils, greases, plant biomass, fibrous waste from pulp and paper mills, and combinations thereof.

4. The composition of claim 1, wherein the SICA has an ion exchange capacity of at least 100 meq/100 grams.

5. The composition of claim 1, wherein the SICA further comprises a selectivity coefficient that ranges from about 1.5 to about 25.

6. The composition of claim 1, wherein the linker molecule is selected from the group consisting of NR¹, C(O), C(O)O, C(O)NR¹, SO, SO₂, SO₂NH, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, and combinations thereof, and wherein R¹ is hydrogen, acyl, aliphatic, or substituted aliphatic.

7. The composition of claim 1, wherein the desired compound further comprises a functional group selected from the group consisting of sulfonic, carboxylic, carboxylate, hydroxyl, halogen, carbonyl, haloformyl, carbonate, alkoxy, acetal, hemiacetal, ketal, hemiketal, amide, primary amine, secondary amine, tertiary amine, quaternary amine, primary ketamine, secondary ketamine, primary aldimine, secondary aldimine, imine, azide, azo, nitrate, nitrile, isonitrile, cyanate, isocyanate, nitro, nitroso, sulfhydryl, sulfide, disulfide, sulfinyl, sulfonyl, sulfino, sulfo, isothiocyanate, carbonothioyl, phosphino, phosphono, phosphate, borono, boronate, borino, borinate, acetamidine, benzamidine, ethylamine, diethylamine, tri-butylamine, triethylamine, sulfonic, carboxylic, alkanes, alkenes, alkynes, arenes, alkyl halides, aryl halides, alcohols, phenols, ethers, aldehydes, ketones, carboxylic acids, esters, amides, amines, nitriles, nitros, and combinations thereof.

8. A composition that reduces the loss of a desired compound from a planting site due to runoff, ground water leaching, evaporation, or windage, the composition comprising:
a substrate coupled to a specific ion complexing agent (SICA), wherein said SICA is coupled to said substrate with a functional group of the substrate, and wherein the substrate is modified to comprise the functional group;
wherein said SICA forms a coordination complex with a desired compound,
wherein the SICA is selected from the group consisting of 1,5-diazabicyclo[4.3.0]non-5-ene, 3,6,9,17,20,23-hexaazatricyclo[23.3.1.111,15]-triaconta-1 (29), 11,13, 15 (30),25,27-hexaene, and 7-[2-Hydroxy-3-(4-phenylpiperazin-1-yl)-propyl]-1, 3-dimethyl-8-(2-morpholin-4-ylethylamino)-3, 7-dihydropurine-2,6-dione, and
wherein said desired compound is selected from the group consisting of a nitrate, nitrite, ammonium, phosphate, sulfate, and combinations thereof.

9. The composition of claim 8, wherein said nitrate, nitrite, ammonium, phosphate, sulfate, or combination thereof is a nutrient, mineral, pesticide, herbicide, growth stimulator, and combinations thereof.

10. The composition of claim 8, wherein the substrate is selected from the group consisting of clay, silica, aluminum silicates, metal oxides, carbohydrates, cellulose, starches, bio-solids, proteins, a single cell protein, amino acids, fats, oils, greases, plant biomass, fibrous waste from pulp and paper mills, and combinations thereof.

11. The composition of claim 8, wherein the SICA has an ion exchange capacity of at least 100 meq/100 grams.

12. The composition of claim 8, wherein the SICA further comprises a selectivity coefficient that ranges from about 1.5 to about 25.

13. The composition of claim 8, wherein the desired compound further comprises a functional group selected from the group consisting of sulfonic, carboxylic, carboxylate, hydroxyl, halogen, carbonyl, haloformyl, carbonate, alkoxy, acetal, hemiacetal, ketal, hemiketal, amide, primary amine, secondary amine, tertiary amine, quaternary amine, primary ketamine, secondary ketamine, primary aldimine, secondary aldimine, imide, azide, azo, nitrate, nitrile, isonitrile, cyanate, isocyanate, nitro, nitroso, sulfhydryl, sulfide, disulfide, sulfinyl, sulfonyl, sulfino, sulfo, isothiocyanate, carbonothioyl, phosphino, phosphono, phosphate, borono, boronate, borino, borinate, acetamidine, benzamidine, ethylamine, diethylamine, tri-butylamine, triethylamine, sulfonic, carboxylic, alkanes, alkenes, alkynes, arenes, alkyl halides, aryl halides, alcohols, phenols, ethers, aldehydes, ketones, carboxylic acids, esters, amides, amines, nitriles, nitros, and combinations thereof.

* * * * *